United States Patent
Sanyal et al.

(10) Patent No.: US 9,994,515 B2
(45) Date of Patent: Jun. 12, 2018

(54) ARYL NAPHTHYL METHANONE OXIME(S) AND PROCESS FOR PREPARATION THEREOF

(71) Applicant: Council of Scientific & Industrial Research, New Delhi (IN)

(72) Inventors: Sabyasachi Sanyal, Lucknow (IN); Atul Kumar, Lucknow (IN); Naibedya Chattopadhyay, Lucknow (IN); Jawahar Lal, Lucknow (IN); Arun Kumar Trivedi, Lucknow (IN); Dipak Datta, Lucknow (IN); Srikanta Kumar Rath, Lucknow (IN); Tahseen Akhtar, Lucknow (IN); Shailendra Kumar Dhar Dwivedi, Lucknow (IN); Manisha Yadav, Lucknow (IN); Bandana Chakravarti, Lucknow (IN); Abhishek Kumar Singh, Lucknow (IN); Jay Sharan Mishra, Lucknow (IN); Nidhi Singh, Lucknow (IN); Anil Kumar Tripathi, Lucknow (IN)

(73) Assignee: Council of Scientific & Industrial Research, New Delhi (IN)

( * ) Notice: Subject to any disclaimer, the term of this patent is extended or adjusted under 35 U.S.C. 154(b) by 7 days.

(21) Appl. No.: 14/915,194

(22) PCT Filed: Aug. 29, 2014

(86) PCT No.: PCT/IN2014/000556
§ 371 (c)(1),
(2) Date: Feb. 26, 2016

(87) PCT Pub. No.: WO2015/029068
PCT Pub. Date: Mar. 5, 2015

(65) Prior Publication Data
US 2016/0304442 A1    Oct. 20, 2016

(30) Foreign Application Priority Data
Aug. 30, 2013    (IN) ............................ 2567/DEL/2013

(51) Int. Cl.
| | | |
|---|---|---|
| *C07C 251/48* | (2006.01) |
| *C07C 251/58* | (2006.01) |
| *C07C 251/60* | (2006.01) |
| *C07C 55/07* | (2006.01) |
| *C07C 57/15* | (2006.01) |
| *C07C 59/255* | (2006.01) |
| *C07C 59/265* | (2006.01) |
| *C07C 249/08* | (2006.01) |
| *C07C 319/02* | (2006.01) |
| *C07C 321/26* | (2006.01) |
| *C07D 295/088* | (2006.01) |

(52) U.S. Cl.
CPC ............ *C07C 251/48* (2013.01); *C07C 55/07* (2013.01); *C07C 57/15* (2013.01); *C07C 59/255* (2013.01); *C07C 59/265* (2013.01); *C07C 249/08* (2013.01); *C07C 251/58* (2013.01); *C07C 251/60* (2013.01); *C07C 319/02* (2013.01); *C07C 321/26* (2013.01); *C07D 295/088* (2013.01)

(58) Field of Classification Search
None
See application file for complete search history.

(56) References Cited

U.S. PATENT DOCUMENTS

| | | | |
|---|---|---|---|
| 4,673,746 A | * | 6/1987 | Shutske |
| 7,485,742 B2 | | 2/2009 | Dannhardt et al. |
| 2007/0276036 A1 | | 11/2007 | Dannhardt et al. |

OTHER PUBLICATIONS

Kumar et al., European Journal of Medicinal Chemistry, 2009, vol. 44(1), pp. 109-116.*

* cited by examiner

*Primary Examiner* — Savitha M Rao
*Assistant Examiner* — Gregg Polansky
(74) *Attorney, Agent, or Firm* — DLA Piper LLP (US)

(57) ABSTRACT

The present invention relates to substituted aryl naphthyl methanone oximes of general formula (I), their process for preparation and their derivatives, salts, pharmaceutical composition thereof and their use in treatment of chronic myelogenous leukemia, acute myelogenous leukemia, lymphoma, multiple myeloma, solid tumor forming cell-lines including such as breast cancer, endometrial cancer colon cancer, prostate cancer and killing of drug resistant cancer stem cells, as subject in need thereof.

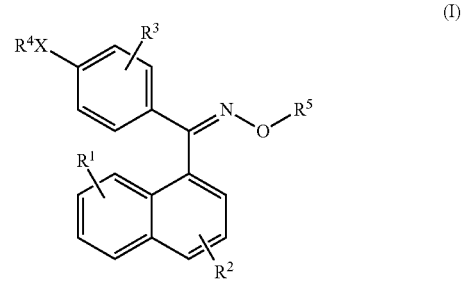

(I)

6 Claims, 9 Drawing Sheets

ARYL NAPHTHYL METHANONE OXIME(S) AND PROCESS FOR PREPARATION THEREOF

CROSS-REFERENCE TO RELATED APPLICATIONS

This application is a 35 USC § 371 National Stage application of International Application No. PCT/IN2014/000556 filed Aug. 29, 2014, now pending; which claims the benefit under 35 USC § 119(a) to India Patent Application No. 2567/DEL/2013 filed Aug. 30, 2013. The disclosure of each of the prior applications is considered part of and is incorporated by reference in the disclosure of this application.

FIELD OF THE INVENTION

The present invention relates to substituted aryl naphthyl methanone oxime (s) of formula I, useful for treatment of cancer, more particularly for treatment of chronic myelogenous leukemia, acute myelogenous leukemia, lymphoma, multiple myeloma, solid tumor forming cell-lines including breast cancer, endometrial cancer, colon cancer, prostate cancer and also for killing of drug resistant cancer stem cells. The present invention also relates to a process for preparation of substituted aryl naphthyl methanone oxime (s).

BACKGROUND OF THE INVENTION

Cancer or malignant neoplasia is a broad group of various diseases characterized by uncontrolled and abnormal growth of cells. It can arise in any organ of the body such as lungs, breast, ovary, intestine etc. The cancerous cells can invade nearby tissues and can spread through the blood stream and lymphatic system to other parts of the body and this process is termed as metastasis. The unchecked growth of cancer results in the death of the host, as a rule, in a few months to few years from the first appearance of symptoms depending to a certain extent upon the site of origin.

The cancer of blood or bone marrow is called leukemia which is characterized by abnormal increase of immature white blood cells. Mainly three classes of agents have been most extensively studied in the search of chemical inducers of differentiation of leukemic cells viz. histone deacetylase (HDAC) inhibitors [Zini, R.; Norfo, R.; Ferrari, F.; Bianchi, E.; Salati, S.; Pennucci, V.; Sacchi, G.; Carboni, C.; Ceccherelli, G. B.; Tagliafico, E.; Ferrari, S.; Manfredini, R. Exp Hematol (2012) 40, (12), 1043-1054 e6], Deoxyribose nucleic acid methyl transferase (DNMT) inhibitors [Savickiene, J.; Treigyte, G.; Borutinskaite, V. V.; Navakauskiene, R. Cell Mol Biol Lett (2012) 17, (4), 501-25] and retinoic acid receptor agonists [Brown, G.; Hughes,

A) DNMT INHIBITORS

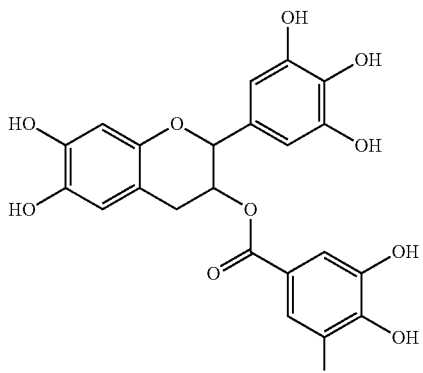

(-) epigallocatechin-O-gallate (EGCG)

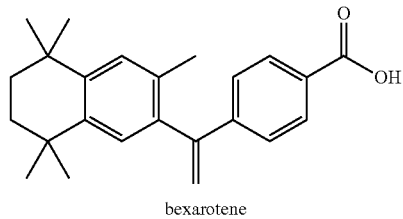

bexarotene

B) BH3 MIMETICS

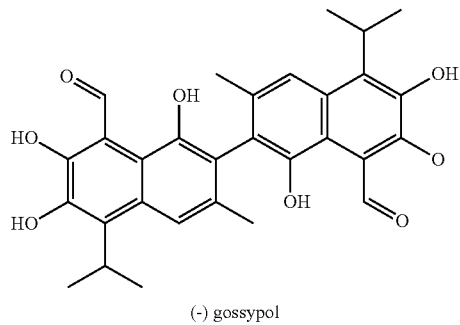

(-) gossypol

C) Bcr-Abl TYROSINE KINASE INHIBITOR

1st Generation inhibitors

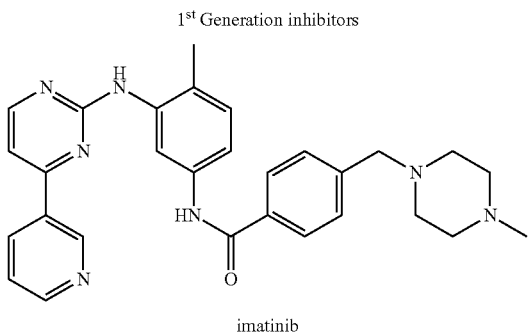

imatinib

2nd Generation inhibitors
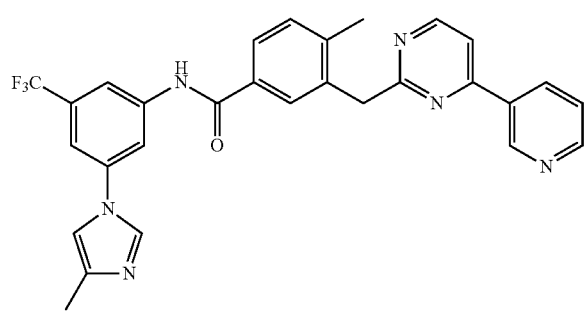
nilotinib
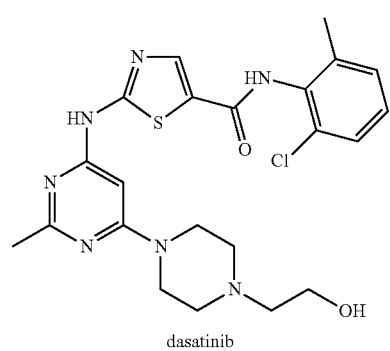
dasatinib
D) UNDER CLINICAL TRIAL
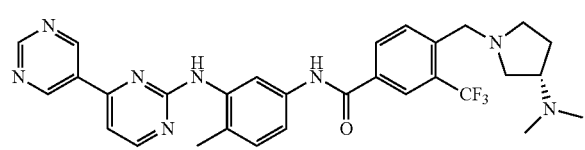
bafetinib
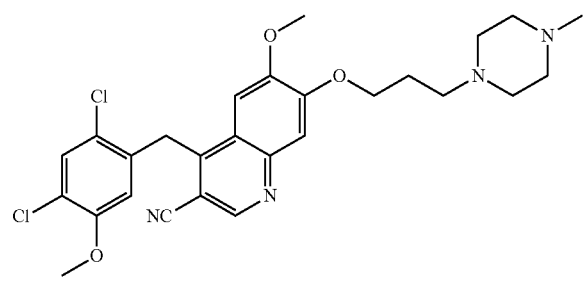
bosutinib
E) FLT3 INHIBITORS
piperazenil quinazoline
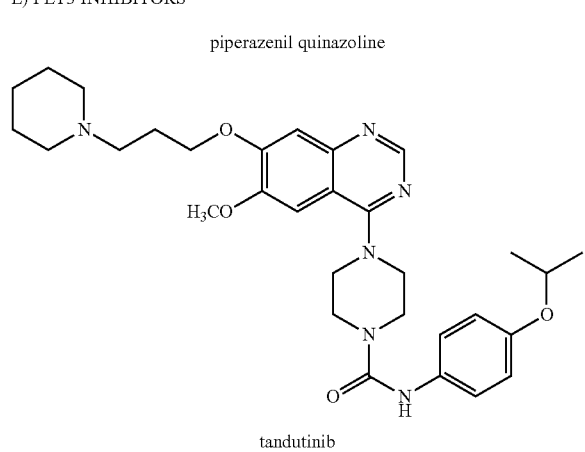
tandutinib
bis aryl ureas
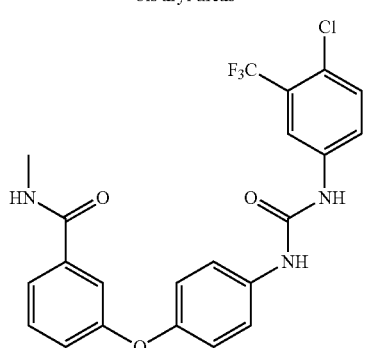
sorafenib
benzimidazole quinolones
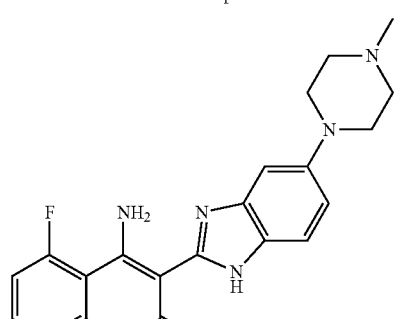
dovitinib
F) CYCLIN DEPENDENT KINASE INHIBITORS
1st Generation inhibitors
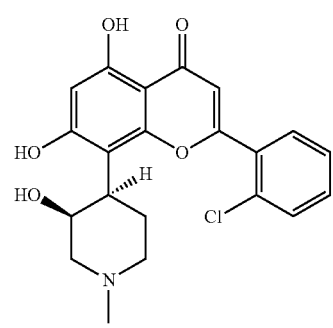
flavopiridol
2nd Generation inhibitors
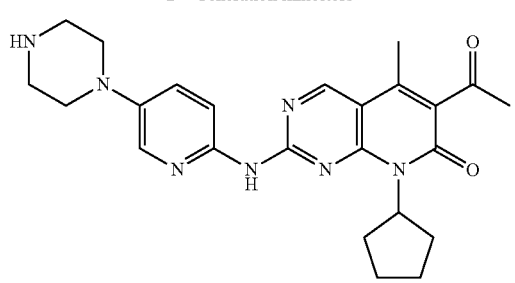
PD0332991

-continued

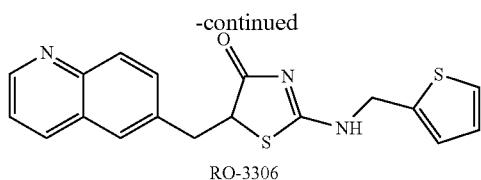
RO-3306

P. *Leuk Res Treatment* (2012), 939021]. (−)-Epigallocatechin 3-gallate (EGCG) is the most intriguing accepted product that exhibit DNMT inhibitory activity though their beneficial anticancer activity may fade due to intercede of its multiple biological effects [Lambert, J. D.; Sang, S.; Yang, C. S. *Chem Res Toxicol* (2007), 20, (4), 583-5.]. Bexarotene is retinoic acid mimetic DNMT inhibitor and is in preclinical stages for the treatment of cutaneous T-cell lymphoma [Qu, L.; Tang, X. *Cancer Chemother Pharmacol* (2010) 65, (2), 201-5.]. In addition, tyrosine kinase inhibitors have proved successful in treatment of various kinds of cancers including chronic myelogenous leukemia (CML) and acute myelogenous leukemia (AML) as well as solid tumors. Imatinib, an inhibitor of BCR-ABL, a constitutively active tyrosine kinase found in CML patients with Philadelphia chromosome (an abnormal translocation of chromosome 9 and 22 creating a fusion between break-point cluster gene (BCR) and ABL kinase) has been the first choice drug for BCR-ABL-positive CML since 2001. However, occurrence of frequent imatinib resistance in patients has necessitated the search for new chemical entities. Nilotinib has relatively favorable safety profile over imatinib as first line tyrosine kinase inhibitor for the treatment of leukemia [Goldman, J. M.; Marin, D. *Oncology (Williston Park)*. (2012) October; 26(10):901-7]. Dual SRC/BCR-ABL tyrosine kinase inhibitor dasatinib has been approved for use in patients with chronic myelogenous leukemia (CML), especially in imatinib resistant cases [Santos, F. P.; Kantarjian, H.; Quintas-Cardama, A.; Cortes, J. *Cancer J* (2011) 17, (6), 465-76.]. However, dasatinib also exhibits limited success rate in imatinib resistant patients and there is occurrence of dasatinib-resistance [Soverini, S.; et al. *Haematologica*. (2007) March; 92(3):401-4]. Dual BCR-ABL/Lyn tyrosine kinase inhibitors like bafetinib or bosutinib have shown strong efficacy in leukemia and solid tumors [Santos, F. P.; Kantarjian, H.; Quintas-Cardama, A.; Cortes, J. *Cancer J* (2011) 17, (6), 465-76., Amsberg, K. G.; Brummendorf, T. H. *Expert Rev anticancer ther* (2012) 12, (9), 1121-1127., Daud, A. I.; Krishnamurthi, S. S.; Saleh, M. N.; Gitlitz, B. J.; Borad, M. J.; Gold, P. J.; Chiorean, E. G.; Springett, G. M.; Abbas, R.; Agarwal, S.; Bardy-Bouxin, N.; Hsyu, P. H.; Leip, E.; Turnbull, K.; Zacharchuk, C.; Messersmith, W. A. *Clin Cancer Res* (2011) 18, (4), 1092-1100]. Inhibitors of type III receptor tyrosine kinase family members including platelet derived growth factor receptors and FMS like tyrosine kinase 3, like tandutinib, sorafenib have been found effective in both leukemia and a number of solid tumors [DeAngelo, D. J.; Stone, R. M.; Heaney, M. L.; Nimer, S. D.; Paquette, R. L.; Klisovic, R. B.; Caligiuri, M. A.; Cooper, M. R.; Lecerf, J. M.; Karol, M. D.; Sheng, S.; Holford, N.; Curtin, P. T.; Druker, B. J.; Heinrich, M. C. *Blood* (2006), 108, (12), 3674-81]. Dovitinib, a multiple tyrosine kinase inhibitor that also inhibits topoisomerases I and II have been shown to be effective in multiple cancer types [Hasinoff, B. B.; Wu, X.; Nitiss, J. L.; Kanagasabai, R.; Yalowich, J. C. *Biochem Pharmacol* (2012) 84, (12), 1617-26]. Efficacy of Cyclin dependent kinase (CDK) inhibitors alone or in combination are also being actively pursued for treatment of both leukemia and solid tumors; Flavopiridol, a synthetic flavonoid inhibitor of CDKs, arrests cell division and causes apoptosis in non-small lung cancer cells and is currently under phase I clinical trial for combination treatment of CML patients with imatinib [Bose, P.; Perkins, E. B.; Honeycut, C.; Wellons, M. D.; Stefan, T.; Jacobberger, J. W.; Kontopodis, E.; Beumer, J. H.; Egorin, M. J.; Imamura, C. K.; Douglas Figg, W., Sr.; Karp, J. E.; Koc, O. N.; Cooper, B. W.; Luger, S. M.; Colevas, A. D.; Roberts, J. D.; Grant, S. *Cancer Chemother Pharmacol* (2012) 69, (6), 1657-67], PD 0332991 is an orally available pyridopyrimidine-derived cyclin-dependent kinase (CDK) inhibitor with potential antineoplastic activity [Leonard, J. P.; LaCasce, A. S.; Smith, M. R.; Noy, A.; Chirieac, L. R.; Rodig, S. J.; Yu, J. Q.; Vallabhajosula, S.; Schoder, H.; English, P.; Neuberg, D. S.; Martin, P.; Millenson, M. M.; Ely, S. A.; Courtney, R.; Shaik, N.; Wilner, K. D.; Randolph, S.; Van den Abbeele, A. D.; Chen-Kiang, S. Y.; Yap, J. T.; Shapiro, G. I. *Blood* (2012):119(20):4597-607] and RO-3306 reversibly arrests human cells at the G2/M border of the cell cycle [Aarts, M.; Sharpe, R.; Garcia-Murillas, I.; Gevensleben, H.; Hurd, M. S.; Shumway, S. D.; Toniatti, C.; Ashworth, A.; Turner, N. C. *Cancer Discov* 2, (6), 524-39.].

Imatinib resistance in BCR-ABL-dependent CML can be divided into two types: a. BCR-ABL dependent. b. BCR-ABL independent. BCR-ABL-dependent resistance can occur due to mutations in the BCR-ABL protein which prevents its binding to imatinib, therefore rendering this protein insensitive to the drug (Pricl, S.; Fermeglia, M.; Ferrone, M.; Tamborini, E. Mol Cancer Ther. (2005) 4(8): 1167-74). Among the reported mutations, T315I point mutation which occurs at the $315^{th}$ amino acid of the ABL kinase, where a threonine moiety is substituted by an isoleucine moiety eliminates an essential oxygen molecule that is critical for hydrogen bonding between BCR-ABL. BCR-ABL has been shown to be insensitive to not only imatinib but also to a number of BCR-ABL inhibitors such as dasatinib and bosutinib [(Pricl, S.; Fermeglia, M.; Ferrone, M.; Tamborini, E. Mol Cancer Ther. (2005) 4(8):1167-74). Weisberg, E.; Manley, P. W.; Cowan-Jacob, S. W.; Hochhaus, A.; Griffin, J. D. Nat Rev Cancer. (2007) 7(5):345-56.] Only ponatinib has been shown to be effective against this mutation (O'Hare, T.; Deininger, M. W.; Eide, C. A.; Clackson, T.; Druker, B. J. Clin Cancer Res. (2011) 17(2):212-21). BCR-ABL-independent imatinib resistance can occur due a number of mechanisms including drug efflux by P-glycoprotein or multi drug resistance group of transporter proteins, defects in drug import in the intracellular milieu or activation of alternate signaling pathway such as activation of src family of kinases which have been implicated in imatinib signaling as well as locking imatinib in an active conformation which is incapable of binding to imatinib (Nestal de Moraes, G.; Souza, P. S.; Costas, F. C.; Vasconcelos, F. C.; Reis, F. R.; Maia, R. C. Leuk Res Treatment. (2012); 2012:671702.). In addition, it has been shown that even in imatinib sensitive cells where BCR-ABL activity is downregulated by imatinib an undifferentiated subpopulation of cells expressing the cluster of differentiation (CD) 34 (CD34; a member of the sialomucin group of transmembrane proteins) but are CD38 negantive (CD34+CD38−) are not killed by imatinib and these cells ultimately are responsible for relapse of leukemia (Corbin, A. S.; Agarwal, A.; Loriaux, M.; Cortes, J.; Deininger, M. W.; Druker, B. J. J Clin Invest. (2011); 121(1):396-409). These cells are termed as "cancer stem cells" (CSC) and they typically harbour some stem cell markers on the cell surface and are refractory to drug treatments. Such CSCs are also evident in all cancer types including solid tumors and are responsible for relapse. In colon cancer cells these CSCs harbour CD133 in the cell surface (O'Brien, C. A.; Pollett, A.; Gallinger, S.; Dick, J. E. Nature. (2007) 445(7123):106-10.). Till date therapeutics for CSCs are not available and only salinomycin has been shown to be effective in killing these cells in vitro (Gupta, P. B.; Onder, T. T.; Jiang, G.; Tao, K.; Kuperwasser, C.; Weinberg, R. A.; Lander, E. S. Cell. (2009) 138(4):645-59).

Treatment of cancer by the use of natural, synthetic, or biologic chemical agents to reverse, suppress, or prevent the process of carcinogenesis is termed as chemotherapy. Essentially, effective implementation of this strategy requires cytotoxicity in not only the malignant cells but also in the cancer stem cells to prevent relapse of cancer following chemotherapy.

OBJECTIVE OF THE INVENTION

The main object of the present invention is to provide a substituted aryl naphthyl methanone oxime(s) or a pharmaceutically acceptable salt thereof.

Another object of the present invention is to provide a pharmaceutical composition containing substituted aryl naphthyl methanone oxime(s) and a pharmaceutically acceptable carrier or a diluent thereof.

Yet another object of the present invention is to provide a process for preparation of substituted aryl naphthyl methanone oxime (s).

Still another object of the present invention is to provide a substituted aryl naphthyl methanone oxime (s) for treatment of hematological malignancy, particularly their use in treatment of leukemia, acute leukemia, lymphoma, multiple myeloma, solid tumors and cancer stem cells.

Yet another object of the present invention is to provide a compound which obviates the drawback of currently available drugs.

Still another object of the present invention is to provide a compound which causes robust apoptosis in existing drug resistant cancer samples.

Yet another object of the present invention is to provide a compound that induces differentiation in blast cells which is indicative of restoring normal blood cell functions.

Still another object of the present invention is to provide a compound which is also efficacious in solid tumor forming cell-lines including, breast, prostate, colon and endometrial cancers.

Yet another object of the present invention is to provide a compound which is efficacious in killing drug resistant cancer stem cells.

SUMMARY OF THE INVENTION

Accordingly, the present invention provides substituted aryl naphthyl methanone oxime(s) of formula (I) and their pharmaceutically acceptable salts thereof.

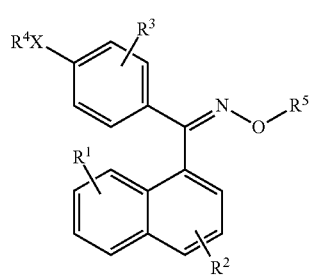

Formula I $R^1$=H, halogen, alkyl, alkoxy, nitro
$R^2$=H, halogen, alkyl, alkoxy, hydroxy, nitro
$R^3$=H, alkyl, alkoxy, nitro, halogen
X=O, S
$R^4$=hydrogen, alkyl group ($c_1$-$c_6$), alkylamino group ($c_1$-$c_6$), cyclic or open chain amines
$R^5$=hydrogen, alkyl group ($c_1$-$c_6$), alkylepoxy, alkylhydroxyamino group ($c_1$-$c_6$), alkylamino group ($c_1$-$c_6$), cyclic or open chain amines, ester and amides derivatives selected from the group consisting of

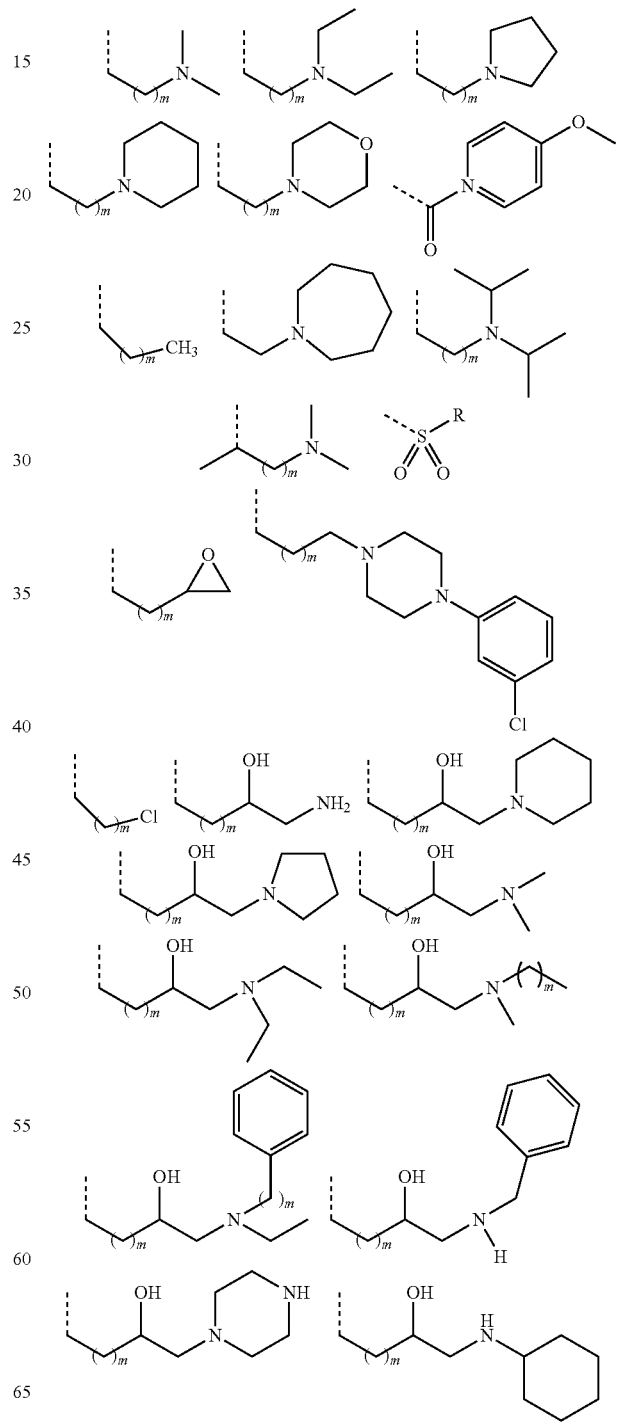

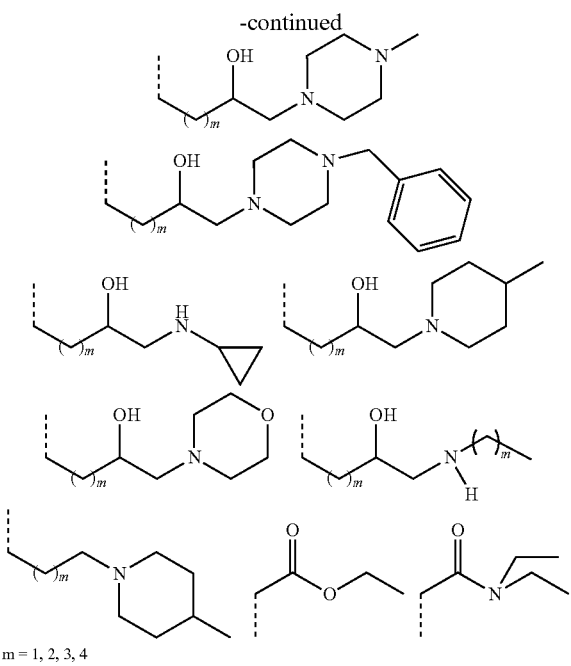

m = 1, 2, 3, 4

In another embodiment of the invention, the compounds are selected from the group consisting of:
1. (4-(methylthio)phenyl)(naphthalen-1-yl)methanone oxime (4a),
2. (4-methoxyphenyl)(naphthalen-1-yl)methanone oxime (4b),
3. (4-hydroxyphenyl)(naphthalen-1-yl)methanone oxime (4c),
4. (4-(methylthio)phenyl)(naphthalen-1-yl)methanone O-2-(piperidin-1-yl)ethyl oxime oxalate (5a),
5. (4-(methylthio)phenyl)(naphthalen-1-yl)methanone O-2-(pyrrolidin-1-yl)ethyl oxime oxalate (5b),
6. (4-(methylthio)phenyl)(naphthalen-1-yl)methanone O-2-(dimethylamino)ethyl oxime oxalate (5c),
7. (4-(methylthio)phenyl)(naphthalen-1-yl)methanone O-2-(diethylamino)ethyl oxime oxalate (5d),
8. (4-(methylthio)phenyl)(naphthalen-1-yl)methanone O-2-(diisopropylamino)ethyl oxime (5e),
9. (4-(methylthio)phenyl)(naphthalen-1-yl)methanone O-2-morpholinoethyl oxime (5f),
10. (4-(methylthio)phenyl)(naphthalen-1-yl)methanone O-1-(dimethylamino)propan-2-yl oxime oxalate (5g),
11. (4-(methylthio)phenyl)(naphthalen-1-yl)methanone O-2-(azepan-1-yl)ethyl oxime oxalate (5h),
12. (4-(methylthio)phenyl)(naphthalen-1-yl)methanone O-2-(diethylamino)ethyl oxime citrate (5i),
13. (4-(methylthio)phenyl)(naphthalen-1-yl)methanone O-2-(diethylamino)ethyl oxime fumarate (5j),
14. (4-(methylthio)phenyl)(naphthalen-1-yl)methanone O-2-(diethylamino)ethyl oxime tartrate (5k),
15. (4-(methylthio)phenyl)(naphthalen-1-yl)methanone O-2-(diethylamino)ethyl oxime (5l),
16. (4-(methylthio)phenyl)(naphthalen-1-yl)methanone O-3-(dimethylamino)propyl oxime oxalate (5m),
17. (4-(methylthio)phenyl)(naphthalen-1-yl)methanone O-3-chloropropyl oxime (5n),
18. (4-(methylthio)phenyl)(naphthalen-1-yl)methanone O-4-chlorobutyl oxime (5o),
19. Ethyl 2-((4-(methylthio)phenyl)(naphthalen-1-yl)methyleneaminooxy)acetate (5p),
20. N,N-diethyl-2-((4-(methylthio)phenyl)(naphthalen-1-yl)methyleneaminooxy) acetamide (5q),
21. (4-methoxyphenyl)(naphthalen-1-yl)methanone O-2-(piperidin-1-yl)ethyl oxime oxalate (6a),
22. (4-methoxyphenyl)(naphthalen-1-yl)methanone O-2-(pyrrolidin-1-yl)ethyl oxime oxalate (6b),
23. (4-methoxyphenyl)(naphthalen-1-yl)methanone O-2-(dimethylamino)ethyl oxime oxalate (6c),
24. (4-methoxyphenyl)(naphthalen-1-yl)methanone O-2-(diethylamino)ethyl oxime oxalate (6d),
25. (4-methoxyphenyl)(naphthalen-1-yl)methanone O-2-(diisopropylamino)ethyl oxime oxalate (6e),
26. (4-methoxyphenyl)(naphthalen-1-yl)methanone O-1-(dimethylamino)propan-2-yl oxime oxalate (6f),
27. (4-methoxyphenyl)(naphthalen-1-yl)methanone O-2-(azepan-1-yl)ethyl oxime oxalate (6g),
28. (4-methoxyphenyl)(naphthalen-1-yl)methanone O-2-morpholinoethyl oxime (6h),
29. (4-methoxyphenyl)(naphthalen-1-yl)methanone O-3-(dimethylamino)propyl oxime oxalate (6i),
30. (4-methoxyphenyl)(naphthalen-1-yl)methanone O-3-chloropropyl oxime (6j),
31. (4-methoxyphenyl)(naphthalen-1-yl)methanone O-3-(piperidin-1-yl)propyl oxime (6k),
32. (4-(methylthio)phenyl)(naphthalen-1-yl)methanone O-3-(piperidin-1-yl)propyl oxime oxalate (7a),
33. (4-(methylthio)phenyl)(naphthalen-1-yl)methanone O-3-morpholinopropyl oxime (7b),
34. (4-(methylthio)phenyl)(naphthalen-1-yl)methanone O-3-(4-methylpiperidin-1-yl)propyl oxime oxalate (7c),
35. (4-(methylthio)phenyl) (naphthalen-1-yl)methanone O-3-(butyl(methyl)amino) propyl oxime (7d),
36. (4-methoxyphenyl)(naphthalen-1-yl)methanone O-3-(2-ethylhexylamino)propyl oxime (7e),
37. (4-(methylthio)phenyl)(naphthalen-1-yl)methanone O-4-(piperidin-1-yl)butyl oxime (8a),
38. (4-(methylthio)phenyl)(naphthalen-1-yl)methanone O-4-(pyrrolidin-1-yl)butyl oxime (8b),
39. (4-(methylthio)phenyl)(naphthalen-1-yl)methanone O-4-(phenethylamino)butyl oxime (8c),
40. (4-(methylthio)phenyl)(naphthalen-1-yl)methanoneO-4-(benzyl(ethyl) amino) butyl oxime (8d), In another embodiment of the invention, the compound is for use in the treatment of cancer and killing of drug resistant cancer stem cells.

In yet another embodiment of the invention, the cancer is selected from the group consisting of blood cancer, leukemia, lymphoma and multiple myeloma.

In another embodiment of the present invention the starting compound 3 used for the preparation of compound of general formula I have been synthesized by our previously reported procedure. (Srivastava, N.; Sangita; Ray, S.; Singh, M. M.; Dwivedi, A.; Kumar, A., *Bioorg Med Chem* (2004), 12, (5), 1011-21).

In another embodiment of the present invention the process for the preparation of compound of general formula I, the said process comprising of:

Reacting substituted phenylnaphthalen-1-yl-methanone (3) of formula II with hydroxylamine hydrochloride and dry pyridine in absolute ethanol to form substituted phenylnaphthalen-1-yl-methanone oxime (4) of formula I. (scheme 1).

Scheme-1

Formula II
(Compound 3)

→ NH$_2$OH•HCl, Base / dry ethanol →

Formula I
(Compound 4)

R$^1$ = H, halogen, alkyl, alkoxy, nitro
R$^2$ = H, halogen, alkyl, alkoxy, hydroxy, nitro
R$^3$ = H, alkyl, alkoxy, nitro, halogen
X = O, S
R$^4$ = hydrogen, alkyl group (c$_1$-c$_6$), alkylamino group (c$_1$-c$_6$), cyclic or open chain amines Scheme 2

Scheme-2

Formula I (compound 5n, o) ← Y–(CH)$_n$–Z / K$_2$CO$_3$/CsCO$_3$ / Acetone/DMF ← Formula I (compound 4) → Cl–R$^5$ / K$_2$CO$_3$/CsCO$_3$ / Acetone/DMF → Formula I (compound 5, 6)

↓ CH$_3$OH/DMF cyclic/open chain amine NR$^6$R$^7$

Formula I (compound 7, 8)

R$^1$ = H, halogen, alkyl, alkoxy, nitro
R$^2$ = H, halogen, alkyl, alkoxy, hydroxy, nitro
R$^3$ = H, alkyl, alkoxy, nitro, halogen
X = O, S, Y, Z = halogen, n = 1,2,3,4,5,6.
R$^4$ = hydrogen, alkyl group (C$_1$-C$_6$), alkylamino group (C$_1$-C$_6$), cyclic or open chain amines
R$^5$ = alkyl group (C$_1$-C$_6$), alkylepoxy, alkylhydroxyamino group (C$_1$-C$_6$), alkylamino group (C$_1$-C$_6$), cyclic or open chain amines, alkyl ester and amides derivatives
R$^6$ = hydrogen, alkyl group (C$_1$-C$_6$), alkylamino group (C$_1$-C$_6$), cyclic or open chain amines
R$^7$ = alkyl group (C$_1$-C$_6$), alkylamino group (C$_1$-C$_6$), cyclic or open chain amines
R$^5$/R$^6$/R$^7$ =

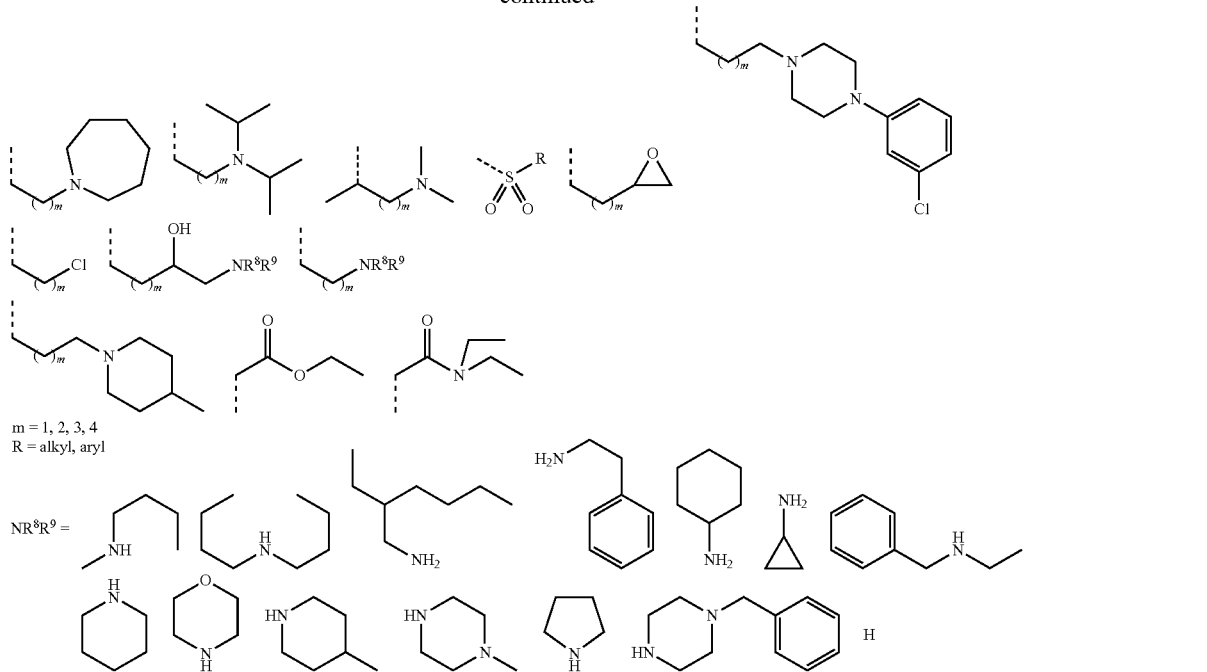

m = 1, 2, 3, 4
R = alkyl, aryl

NR⁸R⁹ =

In another embodiment of the present invention the process for the preparation of compound of general formula I, the said process comprising of reacting a substituted phenylnaphthalen-1-yl-methanone oxime derivative (4) of formula I (scheme 2) with an aminoalkyl chloride, alkyl chloride, alkylepoxychloride, cyclic or open chain amino chloride, alkylhydroxyaminochloride, alkylacetachloride or dihaloalkane (scheme 2) in the presence of a suitable base (defined in scheme 2) at reflux to furnish the compound 5, 6, 7 & 8 of formula I (scheme 2).

In another embodiment of the present invention the base is selected from the group consisting of $K_2CO_3$, $CsCO_3$, KOH and NaH.

In yet another embodiment the solvent is selected from the group consisting of dry DMF, acetone and THF.

In another embodiment of the present invention the pharmaceutically acceptable salts of the compound of general formula I is selected from the group consisting of hydrochlorides, citrates, oxalates, fumarates, malates and tartrates.

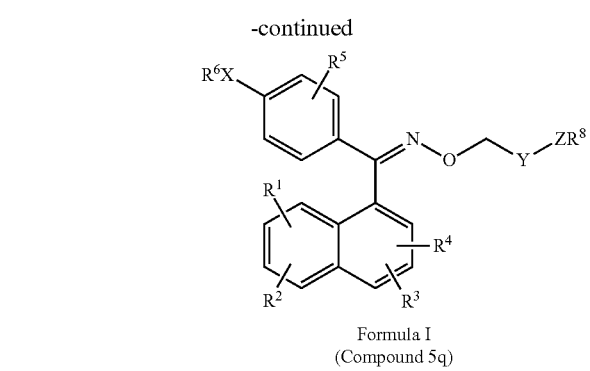

Formula I
(Compound 5q)

$R^1$, $R^2$ = H, halogen, alkyl, alkoxy, nitro
$R^3$, $R^4$ = H, halogen, alkyl, alkoxy, hydroxy, nitro
$R^5$ = H, alkyl, alkoxy, nitro, halogen
X = O, S
Y = carbonyl
Z = N, O
$R^6$ = hydrogen, alkyl group ($C_1$-$C_6$), alkylamino group ($C_1$-$C_6$), cyclic or open chain amines

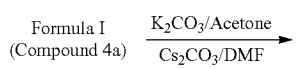

Scheme-3

Scheme-3

Formula I (Compound 4a) →[$K_2CO_3$/Acetone][$Cs_2CO_3$/DMF]

Formula I (Compound 5p) →[$CH_2OH$/DMF, NaH][cyclic/open chain amine, t-ButOK]

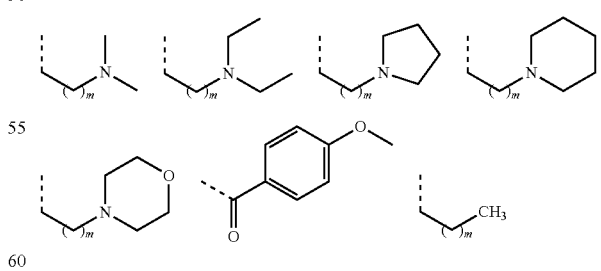

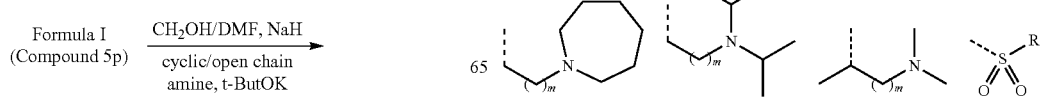

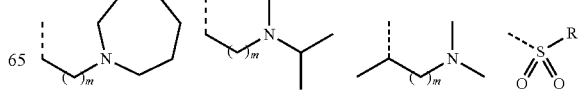

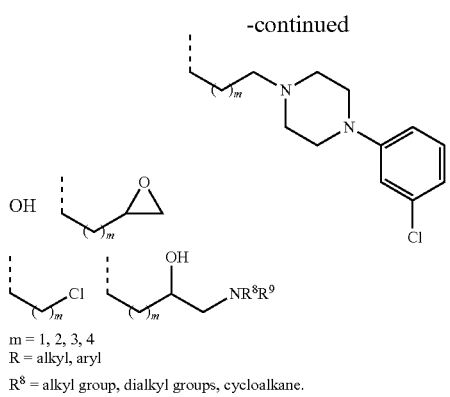

m = 1, 2, 3, 4
R = alkyl, aryl
R⁸ = alkyl group, dialkyl groups, cycloalkane.

In another embodiment of the present invention the process for the preparation of compound of general formula I, the said process comprising of reacting 4a with alkylbromoacetate and the base used is Sodium hydride giving the product 5p of formula I In another embodiment of the present invention the process for the preparation of compound of general formula I, the said process comprising of reacting 5p of formula I with potassium tertiary butoxide and cyclic or open chain amine to produce 5q of formula I. (Scheme 3).

In another embodiment of the present invention the process for the preparation of compound of general formula I, the said process comprising of reacting 4a with alkylbromoacetate and the base used is Sodium hydride giving the product 5p of formula I In another embodiment of the present invention the process for the preparation of compound of general formula I, the said process comprising of reacting 5p of formula I with potassium tertiary butoxide and cyclic or open chain amine to produce 5q of formula I. (Scheme 3).

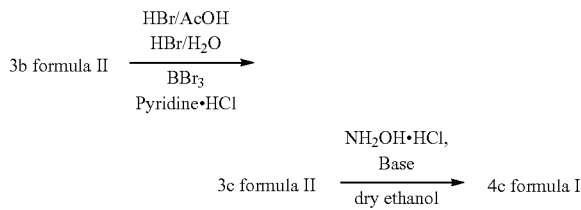

Scheme 4

In another embodiment of the present invention the process for the preparation of compound of general formula II, the said process comprising of:

Reacting substituted Methoxy-phenyl)-naphthalen-1-yl-methanone (3b) formula II with HBr/acetic acid, HBr/H$_2$O, BBr$_3$ or pyridine hydrochloride at 130° C. to furnish the compound (3c) of formula II In another embodiment of the present invention the process for the preparation of compound of general formula I, the said process comprising of Reacting compound 3c (formula II) with hydroxylamine hydrochloride in the presence of a base like sodium acetate or pyridine and solvent used is absolute ethanol/methanol to furnish the compound 4c of formula I. (Scheme 4).

In another embodiment of the present invention, the reactions to furnish the compound of formula I are carried out without any catalyst.

In yet another embodiment of the invention a method for treatment of cancer in a subject comprising, administering to a subject in need thereof an effective amount of a compound of formula 1.

In a more preferred embodiment of the invention, the compound is for use in the treatment of leukemia.

In even preferred embodiment of the invention, the compound is for use in suppression of BCR-ABL activity in CML thereof.

In even more preferred embodiment of the invention, the compound is for use in suppression of c-SRC activity in imatinib-resistance in CML thereof.

In a more preferred embodiment of the invention, the compound is for use in inducing apoptosis in imatinib-resistant CML cells.

In a preferred embodiment of the invention, the compound is for use in inducing of apoptosis and differentiation in AML cells.

In another embodiment of the invention, the compound is for use in inducing megakaryocytic differentiation in K562 cells and inducing differentiation in blast cells of erythro-leukemia or increasing platelet amount.

In a more preferred embodiment of the invention, the compound is for use in exhibiting cancer-specific cytotoxicity in ER-positive or ER-negative breast cancer cells, prostate cancer cells, uterine adenocarcinoma and colon cancer cells.

In an even preferred embodiment of the invention, the compound is for use in selective cytotoxicity towards cancer stem cells such as but not limited to CD133+ colon cancer stem cells.

In another embodiment of the invention, the representative compounds of formula I and its salts thereof are used for the treatment of solid tumors and hematological malignancy, more particularly their use in treatment of leukemia, acute leukemia, lymphoma and multiple myeloma.

In another embodiment of the present invention, the pharmaceutical composition is provided comprising an effective amount of a compound of formula I optionally along with a pharmaceutically acceptable carrier or diluents.

In another embodiment of the present invention, the compound is for use as anti-cancer agent and for treatment of hematological malignancy such as their use in treatment of leukemia, acute leukemia, lymphoma and multiple myeloma and as well as in solid tumors.

ABBREVIATIONS

Figure 1:
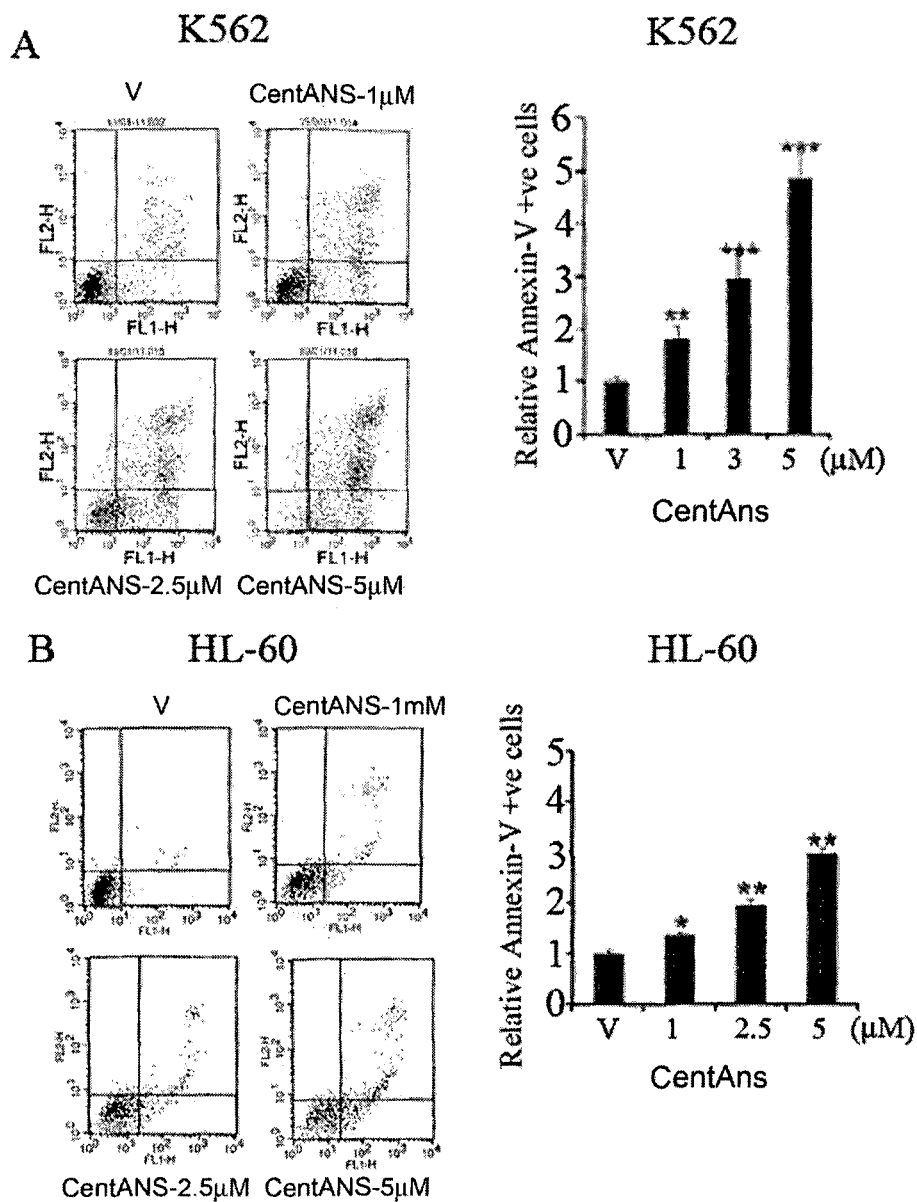
FIG. 1: CentANS induces apoptotic cell death in K562 and HL-60 cells

Centans: Abbreviation used for compounds based on the IUPAC name of the compound, prefixed with Cent; a Central Drug Research Institute signature.
CML: Chronic myelogenous leukemia
AML: Acute myelogenous leukemia
PBMC: Peripheral blood mononuclear cells
BCR: "Break point cluster region" gene
ABL: Abelson murine leukemia viral oncogene homolog 1
BCR-ABL: a fusion protein of BCR and ABL
APOP: Apoptosis
Stat5: Signal transducer and activator of transcription 5
Crkl: v-CRK avian sarcoma virus CT10-homolog-like
eIF4E: Eukaryotic translation initiation factor 4E
GATA-2: GATA binding protein 2
ER: Estrogen Receptor
MTT: 3-(4,5-dimethythiazol-. 2-yl)-2,5-diphenyl tetrazolium bromide
PI: Propidium Iodide

DETAILED DESCRIPTION OF THE INVENTION

Accordingly, the present invention provides the process for preparation of substituted aryl naphthyl methanone oximes of general formula (I) and their derivatives, salts, pharmaceutical composition thereof and their use in treatment of chronic myelogenous leukemia, acute myelogenous leukemia, lymphoma, multiple myeloma, breast cancer, endometrial cancer prostate cancer and colon cancer as subject in need thereof.

The present invention provides substituted aryl naphthyl methanone oxime (s) of formula (I), for use in the treatment of hematological malignancy, particularly for use in treatment of leukemia, acute leukemia, lymphoma and multiple myeloma and solid tumors such as breast cancer, endometrial cancer, prostate cancer and colon cancer.

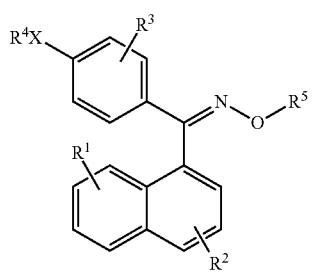

Formula I $R^1$=H, halogen, alkyl, alkoxy, nitro
$R^2$=H, halogen, alkyl, alkoxy, hydroxy, nitro
$R^3$=H, alkyl, alkoxy, nitro, halogen
X=O, S
$R^4$=hydrogen, alkyl group ($c_1$-$c_6$), alkylamino group ($c_1$-$c_6$), cyclic or open chain amines
$R^5$=hydrogen, alkyl group ($c_1$-$c_6$) alkylepoxy, alkylhydroxyamino group ($c_1$-$c_6$), alkylamino group ($c_1$-$c_6$), cyclic or open chain amines, alkyl ester and amides derivatives selected from the group consisting of

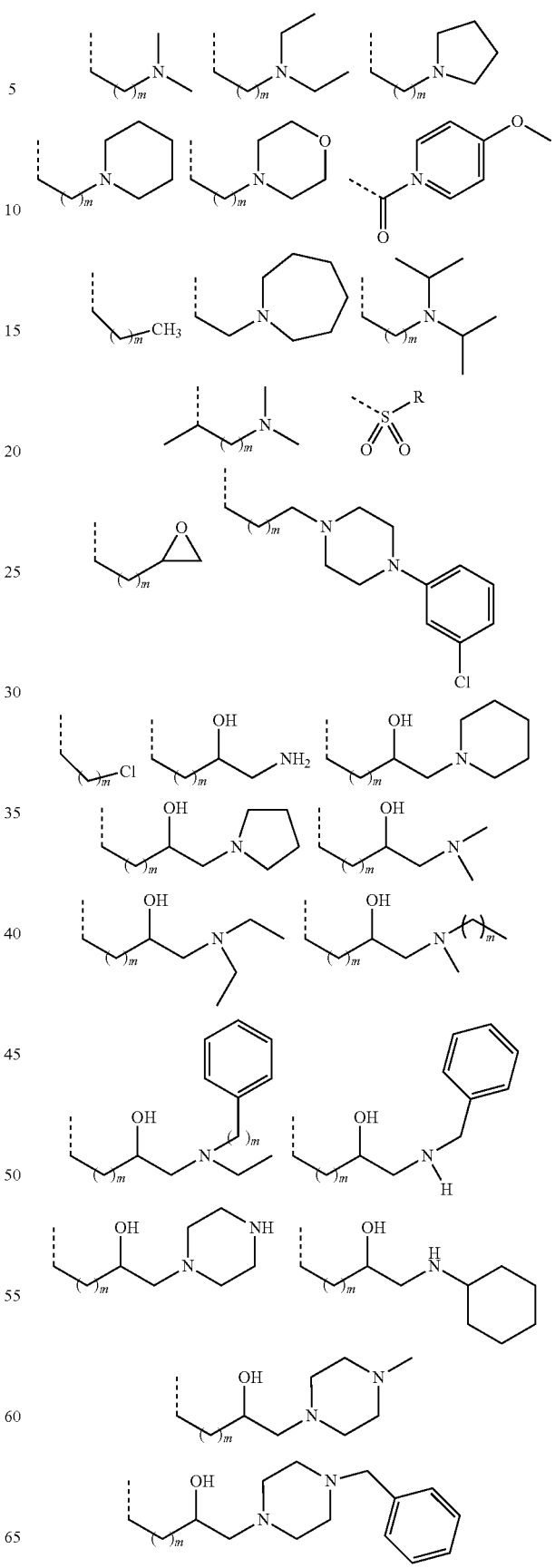

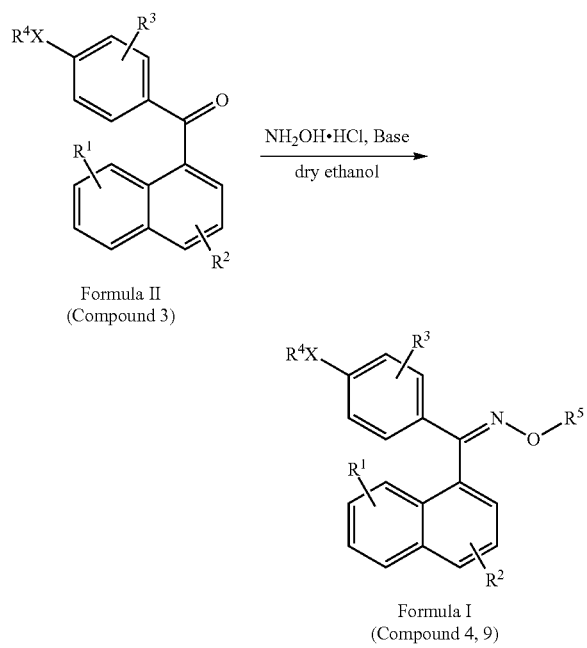

m = 1, 2, 3, 4

This invention also relates to a process for the preparation of Substituted Aryl naphthyl methanone oxime (s). Reacting the substituted Naphthalene-1-carboxylic acid (1) and suitably substituted phenol or thiophenol (2) in the presence of PPA at 90° C. to yield compound 3b. (Formula II) [Atul Kumar, S. R. Pathak, Pervez Ahmad, S. Ray, P. Tewari, A. K. Srivastava *Bioorganic & Medicinal Chemistry Letters* 16 (2006) 2719-2723].

Scheme-1

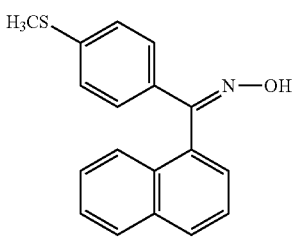

Formula II
(Compound 3)

Formula I
(Compound 4, 9)

$R^1$ = H, halogen, alkyl, alkoxy, nitro
$R^2$ = H, halogen, alkyl, alkoxy, hydroxy, nitro
$R^3$ = H, alkyl, alkoxy, nitro, halogen
X = O, S
$R^4$ = hydrogen, alkyl group ($c_1$-$c_6$), alkylamino group ($c_1$-$c_6$), cyclic or open chain amines
$R^5$ = H The compound 3 on treatment with a hydroxylamine hydrochloride in the presence of base like pyridine, sodium acetate in dry ethanol yields compound 4. (Formula I)

Compound 4 on treatment with a number of alkyl halides in the presence of base, like $K_2CO_3$, $CsCO_3$, KOH, NaH etc. in dry DMF or acetone, yields compound 5, 6 of formula I.

Compound 4 on treatment with various dihaloalkanes in the presence of base, like $K_2CO_3$, $CsCO_3$ etc. in dry DMF/acetone also yields compound 5n, o (formula I), which on reaction with a number of amines in dry DMF/Methanol yields compound 7 & 8 of formula I (Scheme 2).

Compound 4b on treatment with HBr/acetic acid, HBr/$H_2O$, $BBr_3$ or pyridine hydrochloride yields compound 4c (formula I).

Following examples are given by way of illustrations and therefore, should not be construed to limit the scope of the present invention:

EXAMPLES

Synthesis of Compounds

The following examples are given by way of illustrating the present invention and should not be construed to limit the scope of the invention:

Example 1

Synthesis of (4-(methylthio)phenyl)(naphthalen-1-yl)methanone oxime (Compound 4a)

Into a 50 ml round bottom flask, (4-Methylsulfanyl-phenyl)-naphthalen-1-yl-methanone (1 mmole, 278 mg), hydroxylamine hydrochloride (2 mmole, 140 mg), dry pyridine (0.5 ml) and absolute ethanol (7.0 ml) were taken to obtain a reaction mixture. The reaction mixture was refluxed at 80° C. under anhydrous conditions for 8 hours. The reaction was followed by TLC (thin layer chromatography) monitoring. After completion of the reaction, ethanol was evaporated under reduced pressure. The resulting mixture was poured onto crushed ice and extracted with ethyl acetate (3×50 ml), washed with water until pH=7, dried over anhydrous $Na_2SO_4$ (8-9g) and concentrated. The crude product was purified by silica gel column chromatography using ethyl acetate and distilled Hexane as an eluent (8%) to yield the pure product It was then recrystellize from ethyl acetate and Hexane. Yield: 215 mg, 73.4%.

M.P.=135° C., ESI MS (m/z)=294 (M+H); IR (KBr, $Cm^{-1}$): 3235.8, 2921.5, 1899.5, 1591.0, 1491.1, 1434.8, 1390.9, 1352.4, 1313.1, 1093.0, 1074.0, 969.6, 922.0, 770.1, 695.6; $^1$H NMR($CDCl_3$, 300MHz): δ=7.99 (t, J=8.7 Hz, 2H, ArH), 7.73(d, J=8.1 Hz, 1H, ArH), 7.64-7.33(m, 6H, ArH), 7.16(d, J=7.2 Hz, 2H, ArH), 2.46(s, 3H, $SCH_3$); $^{13}$C NMR (CDCl3, 50 MHz): δ=157.43, 141.26, 133.89, 132.75, 131.73, 130.80, 129.61, 128.89, 127.84(2), 127.14, 126.74, 126.54 (2), 126.23, 126.09, 125.73, 15.67; Analysis calculated for $C_{18}H_{15}NOS$: C, 73.69; H, 5.15; N, 4.77. found: C, 73.71; H, 5.16; N, 4.80.

Example 2

Synthesis of (4-methoxyphenyl)(naphthalen-1-yl)methanone oxime (Compound 4b)

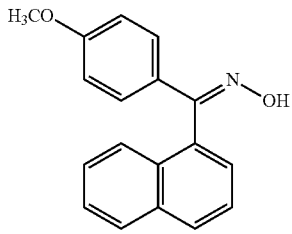 [SMILES: COc1ccc(/C(=N/O)c2cccc3ccccc23)cc1]

Into a 50 ml round bottom flask, (4-Methoxy phenyl)-naphthalen-1-yl-methanone (1 mmole, 262 mg), hydroxylamine hydrochloride (2 mmole, 140 mg), dry pyridine (0.5 ml) and absolute ethanol (7.0 ml) were taken. The reaction mixture was refluxed under anhydrous conditions for 8 hours. The reaction was followed by TLC monitoring. After completion of the reaction, ethanol was evaporated under reduced pressure. The resulting mixture was poured onto crushed ice and extracted with ethyl acetate (3×50 ml), washed with water until pH=7, dried over anhydrous $Na_2SO_4$ and concentrated. The crude product was purified by silica gel column chromatography using ethyl acetate and distilled Hexane as an eluent (6%) to yield the pure product. It was then recrystallized from ethyl acetate and Hexane. Yield: 209 mg, 75.45%.

M.P.=132° C.; ESI MS(m/z)=278(M+H); IR (KBr, $Cm^{-1}$): 3254.2, 3056.7, 2924.9, 1603.6, 1510.5, 1460.0, 1252.1, 1176.3, 1025.4, 970.4, 928.8, 835.0, 771.8; $^1$H NMR($CDCl_3$, 300MHz): δ=7.95(t, J=6.6 Hz, 2H, ArH), 7.76(d, J=8.1 Hz, 1H, ArH), 7.63-7.39(m, 6H, ArH), 6.83(d, J=8.9 Hz, 2H, ArH), 3.79(s, 3H, $OCH_3$); $^{13}$C NMR ($CDCl_3$, 75MHz): 160.82, 156.91, 133.51, 132.14, 131.87, 130.47, 129.11, 128.65, 128.48, 128.39, 126.72, 126.32, 126.13, 125.87, 125.38, 125.20, 113.91, 55.32; Analysis calculated for $C_{18}H_{15}NO_2$: C, 77.96; H, 5.45; N, 5.05, found: C, 77.97; H, 5.43; N, 5.07.

Example 3

Synthesis of (4-hydroxyphenyl)(naphthalen-1-yl)methanone oxime (Compound 4c)

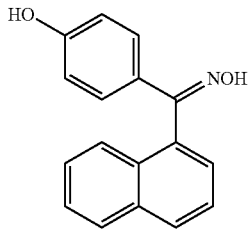

Into a 50 ml round bottom flask, (4-Hydroxy-phenyl)-naphthalen-1-yl-methanone (1 mmole, 248 mg), hydroxylamine hydrochloride (2 mmole, 140 mg), dry pyridine (0.5 ml) and absolute ethanol (7.0 ml) were taken. The reaction mixture was refluxed under anhydrous conditions for 7 hours. The reaction was followed by TLC monitoring. After completion of the reaction, ethanol was evaporated under reduced pressure. The resulting mixture was poured onto crushed ice and extracted with ethyl acetate (3×50 ml), washed with water until pH=7, dried over anhydrous $Na_2SO_4$ and concentrated. The crude product was purified by silica gel column chromatography using chloroform as eluent to yield the pure product. It was then recrystellized with ethyl acetate and hexane. Yield: 221 mg, 84.03%. ESI MS (m/z)=264 (M+H); $^1$H NMR (200 MHz, $CDCl_3$): δ=7.91(t, J=8.0 Hz, 2H, ArH), 7.71(d, J=8.0 Hz, 1H, ArH), 7.55-7.31(m, 5H, ArH), 7.26(m, 1H, ArH), 6.52-6.47(m, 2H, ArH); $^{13}$C NMR($CDCl_3$+$CD_3OD$, 75MHz): 159.61, 157.99, 134.92, 134.07, 131.88, 129.84, 129.78(2), 129.51, 129.37, 127.50, 127.27, 127.11, 126.94, 126.48, 116.41; Analysis calculated for $C_{17}H_{13}NO_2$: C, 77.55; H, 4.98; N, 5.32, found: C, 77.50; H, 5.06; N, 5.26.

Example 4

Synthesis of (4-(methylthio)phenyl)(naphthalen-1-yl)methanone O-2-(piperidin-1-yl)ethyl oxime oxalate (Compound 5a)

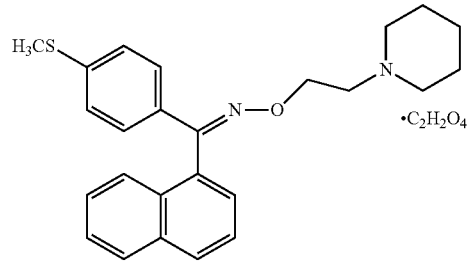

Into a 50 ml round bottom flask, 4-(methylthiophenyl)(naphthalen-1-yl)methanone oxime (1 mmole, 293 mg), 1-(2-chloroethyl)piperidine hydrochloride (1.2 mmole, 220.8 mg), baked $K_2CO_3$ (5 mmole, 690 mg) and dry acetone (10.0 ml) were taken. The reaction mixture was refluxed under anhydrous conditions for 6 hours. The reaction was followed by TLC monitoring. After completion of the reaction, $K_2CO_3$ was filtered off and washed with acetone (2×10 ml). Filtrate was concentrated and the crude product was purified by basic alumina column chromatography using distilled Hexane to yield the pure product (349 mg, 86.6%). The product obtained was oily, so a salt of the compound was prepared.

Procedure for oxalate salt formation: Oxalic acid, 1 mmole/1 mmole of compound, (109.1 mg) and oily product (349 mg) were dissolved in dry methanol separately into two round bottom flasks. The acid and the compound were mixed and shaken thoroughly. The salt was precipitated using dry diethyl ether, filtered, washed with the same and collected. Yield: 390 mg, 85.2%.

M.P. (Oxalate Salt of compound)=155° C., ESI MS (m/z)=404; IR (KBr, $Cm^{-1}$)=3020.4, 2970.1, 2360.8, 1758.4, 1630.1, 1522.3, 1216.4, 761.8, 670.3; $^1$H NMR ($CDCl_3$, 200MHz): δ=7.94 (d, J=8.0 Hz, 2H, ArH), 7.63-7.41(m, 5H, ArH), 7.29-7.27(m, 2H, ArH), 7.18 (d, J=8.2 Hz, 2H, ArH), 4.46(m, 2H, $OCH_2$), 3.21(m, 4H, $NCH_2$)2.47-2.46(m, 5H, $SCH_3$ & $NCH_2$), 1.51(m, 5H, $CH_2$). Analysis calculated for $C_{25}H_{28}N_2OS$: C, 74.22; H, 6.98; N, 6.92; found: C, 74.25; H, 6.95; N, 6.96.

Example 5

Synthesis of (4-(methylthio)phenyl)(naphthalen-1-yl)methanone O-2-(pyrrolidin-1-yl)ethyl oxime oxalate (Compound 5b)

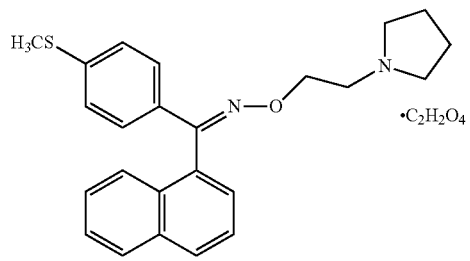

Into a 50 ml round bottom flask, 4-(methylthiophenyl)(naphthalen-1-yl)methanone oxime (1 mmole, 293 mg), 1-(2-chloroethyl)pyrrolidine hydrochloride (1.2 mmole, 204 mg), baked $K_2CO_3$ (5 mmole, 690 mg) and dry acetone (10.0 ml) were taken. The reaction mixture was refluxed under anhydrous conditions for 6 hours. The reaction was followed by TLC monitoring. After completion of the reaction, $K_2CO_3$ was filtered off and washed with acetone (2×10 ml). Filtrate was concentrated and the crude product was purified by basic alumina column chromatography using distilled Hexane to yield the pure product (250 mg, 64.26%). The product obtained was oily, so a salt of the compound was prepared.

Procedure for oxalate salt formation: Oxalic acid, 1 mmole/1 mmole of compound, (108.9 mg) and oily product (250 mg) were dissolved in dry methanol separately into two round bottom flasks. The acid and the compound were mixed and shaken thoroughly. The salt was precipitated using dry diethyl ether, filtered, washed with the same and collected. Yield: 390 mg, 85.2%.

M.P. (Oxalate Salt of compound)=153° C., ESI MS (m/z)=390 (M+H); IR (KBr, $Cm^{-1}$)=3021.01, 2359.2, 1757.5, 1629.5, 1216.6, 761.0, 671.4; $^1$H NMR (CDCl$_3$, 200MHz): δ=7.93 (d, J=7.6 Hz, 2H, ArH), 7.62-7.41(m, 5H, ArH), 7.29-7.27(m, 2H, ArH), 7.17 (d, J=8.4 Hz, 2H, ArH), 4.61-4.45(m, 2H, OCH$_2$), 3.29(m, 2H, NCH$_2$), 2.82-2.80(m, 4H, NCH$_2$), 2.47(s, 3H, SCH$_3$), 1.70(m, 4H, CH$_2$). Analysis calculated for $C_{24}H_{26}N_2OS$ (free base): C, 73.81; H, 6.71; N, 7.17, found: C, 73.79; H, 6.68; N, 7.15.

Example 6

Synthesis of (4-(methylthio)phenyl)(naphthalen-1-yl)methanone O-2-(dimethylamino)ethyl oxime oxalate (Compound 5c)

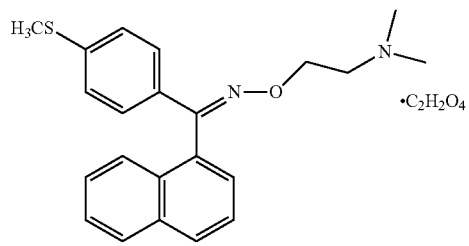

Into a 50 ml round bottom flask, 4-(methylthiophenyl)(naphthalen-1-yl)methanone oxime (1 mmole, 293 mg), (2-Chloro-ethyl)-dimethyl-amine hydrochloride (1.2 mmole, 172.8 mg), baked $K_2CO_3$ (5 mmole, 690 mg) and dry acetone (10.0 ml) were taken. The reaction mixture was refluxed under anhydrous conditions for 6 hours. The reaction was followed by TLC monitoring. After completion of the reaction, $K_2CO_3$ was filtered off and washed with acetone (2×10 ml). Filtrate was concentrated and the crude product was purified by basic alumina column chromatography using distilled Hexane to yield the pure product (280 mg, 76.9%). The product obtained was oily, so a salt of the compound was prepared.

Procedure for oxalate salt formation: Oxalic acid, 1 mmole/1 mmole of compound, (96.9 mg) and oily product (280 mg) were dissolved in dry methanol separately into two round bottom flasks. The acid and the compound were mixed and shaken thoroughly. The salt was precipitated using dry diethyl ether, filtered, washed with the same and collected. Yield: 310 mg, 63.27%.

M. P. (Oxalate Salt of compound)=105° C.; ESI MS (m/z)=365 (M+H), IR (KBr, $Cm^{-1}$): 3020.5, 2970.8, 2362.1, 1757.3, 1629.1, 1216.4, 1044.6, 760.9, 670.2; $^1$H NMR (CDCl3, 200MHz): δ=7.93 (d, J=7.7 Hz, 2H, ArH), 7.61-7.41(m, 5H, ArH), 7.28-7.25(m, 2H, ArH), 7.17(d, J=8.4 Hz, 2H, ArH), 4.65-4.49(m, 2H, OCH$_2$), 3.47(s, 6H, NCH$_3$), 2.45(s, 3H, SCH$_3$), 2.40(m, 2H, NCH$_2$). Analysis calculated for $C_{22}H_{24}N_2OS$ (free base): C, 72.49; H, 6.64; N, 7.69; Found: C, 72.46; H, 6.63; N, 7.67.

Example 7

Synthesis of (4-(methylthio)phenyl)(naphthalen-1-yl)methanone O-2-(diethylamino)ethyl oxime oxalate (Compound 5d)

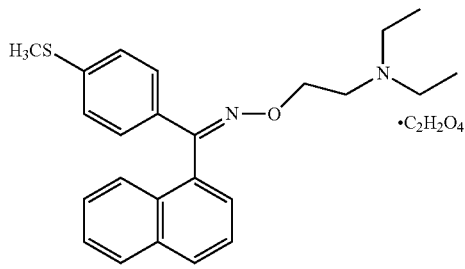

Method A: Into a 50 ml round bottom flask, 4-(methylthiophenyl)(naphthalen-1-yl)methanone oxime (1 mmole, 293 mg), 2-chloro-N,N-diethylethanamine hydrochloride (1.2 mmole, 205 mg), baked $K_2CO_3$ (5 mmole, 690 mg) and dry acetone (10.0 ml) were taken. The reaction mixture was refluxed under anhydrous conditions for 6 hours. The reaction was followed by TLC monitoring. After completion of the reaction, $K_2CO_3$ was filtered off and washed with acetone (2×10 ml). Filtrate was concentrated and the crude product was purified by basic alumina column chromatography using distilled Hexane to yield the pure product (250 mg, 63.6%). The product obtained was oily so a salt of the compound was prepared.

Procedure for oxalate salt formation: Oxalic acid, 1 mmole/1 mmole of compound, (80.15 mg) and the oily product (250 mg) were dissolved in dry methanol separately into two round bottom flasks. The acid and the compound were mixed and shaken thoroughly. The salt was precipitated using dry diethyl ether, filtered, washed with the same and collected. Yield: 259 mg, 48.3%.

M.P. (Oxalate Salt of compound)=115° C.; ESI MS (m/z) =393 (M+H); $^1$H NMR(CDCl$_3$, 200MHz): δ=7.93(d, J=8.0 Hz, 2H, ArH), 7.63-7.41(m, 5H, ArH), 7.27-7.25(m, 2H, ArH), 7.17-7.13(d, J=8.0 Hz, 2H, ArH), 4.48(m, 2H, OCH$_2$), 3.26(m, 2H, NCH$_2$), 2.72(m, 4H, NCH$_2$), 2.46(s, 3H, SCH$_3$), 0.81(m, 6H, CH$_3$); Analysis calculated for C$_{26}$H$_{30}$N$_2$O$_5$S: C, 64.71; H, 6.27; N, 5.80 found: C, 64.76; H, 6.26; N, 5.85.

Method B: Into a 50 ml round bottom flask, 4-(methylthiophenyl)(naphthalen-1-yl)methanone oxime (1 mmole, 293 mg), 2-chloro-N,N-diethylethanamine hydrochloride (1.2 mmole, 205 mg), Cs$_2$CO$_3$ (5 mmole) and dry DMF (10.0 ml) were taken. The reaction mixture was refluxed under anhydrous conditions for 5 hours. The reaction was followed by TLC monitoring. After completion of the reaction, filtrate was concentrated and the crude product was purified by basic alumina column chromatography using distilled Hexane to yield the pure product (62.6%).

Example 8

Synthesis of (4-(methylthio)phenyl)(naphthalen-1-yl)methanone O-2-(diisopropylamino)ethyl oxime (Compound 5e)

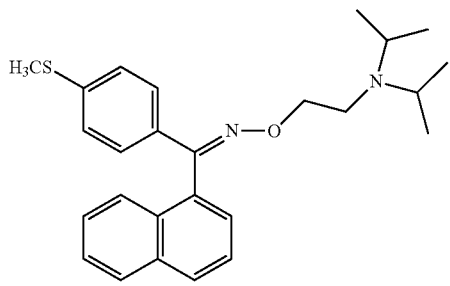

Into a 50 ml round bottom flask, 4-(methylthiophenyl)(naphthalen-1-yl)methanone oxime (1 mmole, 293 mg), (2-Chloro-ethyl)-diisopropyl-amine hydrochloride (1.2 mmole, 240 mg), baked K$_2$CO$_3$ (5 mmole, 690 mg) and dry acetone (10.0 ml) were taken. The reaction mixture was refluxed under anhydrous conditions for 6 hours. The reaction was followed by TLC monitoring. After completion of the reaction, K$_2$CO$_3$ was filtered off and washed with acetone (2×10 ml). Filtrate was concentrated and the crude product was purified by basic alumina column chromatography using distilled Hexane to yield the pure product (325 mg, 77.38%). Oily Compound; ESI MS (m/z)=421(M+H); $^1$H NMR(CDCl$_3$, 200MHz): 7.92(d, J=7.6 Hz, 2H, ArH), 7.57-7.39(m, 5H, ArH), 7.32-7.26(m, 2H, ArH), 7.15 (d, J=8.5 Hz, 2H, ArH), 4.09 (t, J=7.2 Hz, 2H, OCH$_2$), 2.94-2.88(m, 2H, NCH), 2.68(m, 2H, NCH$_2$), 2.45(s, 3H, SCH$_3$), 0.93-0.89(d, J=6.5 Hz, 12H, CH$_3$). Analysis calculated for C$_{26}$H$_{32}$N$_2$OS: C, 74.24; H, 7.67; N, 6.66, found: C, 74.20; H, 7.65; N, 6.65.

Example 9

Synthesis of (4-(methylthio)phenyl)(naphthalen-1-yl)methanone O-2-morpholinoethyl oxime (Compound 5f)

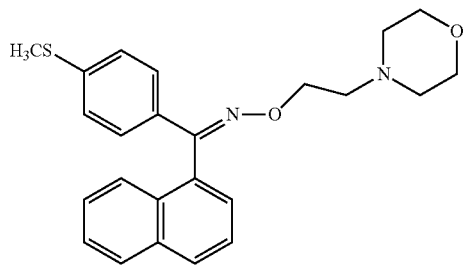

Into a 50 ml round bottom flask, 4-(methylthiophenyl)(naphthalen-1-yl)methanone oxime (1 mmole, 293 mg), 4-(2-Chloro-ethyl)-morpholine hydrochloride (1.2 mmole, 223.2 mg), baked K$_2$CO$_3$ (5 mmole, 690 mg) and dry acetone (10.0 ml) were taken. The reaction mixture was refluxed under anhydrous conditions for 6 hours. The reaction was followed by TLC monitoring. After completion of the reaction, K$_2$CO$_3$ was filtered off and washed with acetone (2×10 ml). Filtrate was concentrated and the crude product was purified by basic alumina column chromatography using distilled Hexane to yield the pure product (298 mg, 73.22%). Oily compound, ESI MS (m/z)=407 (M+H); IR(Neat, Cm$^{-1}$): 4300.2, 3020.6, 1757.4, 1593.6, 1216.5, 1042.5, 762.0, 671.3; $^1$H (300MHz, CDCl$_3$): δ=7.93 (d, J=8.3 Hz, 2H, ArH), 7.68 (d, J=8.2 Hz, 1H, ArH), 7.58-7.40 (m, 5H, ArH), 7.32-7.28(m, 1H, ArH), 7.18(d, J=8.4 Hz, 2H, ArH), 4.33(t, J=5.6 Hz, 2H, OCH$_2$), 3.77-3.51(m, 4H, OCH$_2$), 2.63(t, J=5.6 Hz, 2H, NCH$_2$), 2.47(s, 311, SCH$_3$), 2.27(t, J=4.3 Hz, 4H, NCH$_2$); Analysis calculated for C$_{24}$H$_{26}$N$_2$O$_2$S: C, 70.90; H, 6.45; N, 6.89, found: C, 70.89; H, 6.40; N, 6.86.

Example 10

Synthesis of (4-(methylthio)phenyl)(naphthalen-1-yl)methanone O-1-(dimethylamino)propan-2-yl oxime oxalate (Compound 5g)

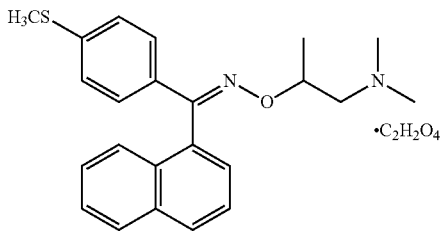

Method A: Into a 50 ml round bottom flask, 4-(methylthio)phenyl (naphthalen-1-yl)methanone oxime (1 mmole, 293 mg), (2-Chloro-propyl)-dimethyl-amine hydrochloride (1.2 mmole, 189.6 mg), baked K$_2$CO$_3$ (5 mmole, 690 mg) and dry DMF (10.0 ml) were taken. The reaction mixture was refluxed under anhydrous conditions for 5 hours. The reaction was followed by TLC monitoring. After completion of the reaction, the mixture was quenched into water (100 ml), extracted with ethyl acetate (3×75 ml) and dried over anhydrous Na$_2$SO$_4$. The filtrate was concentrated and the crude product was purified by basic alumina column chromatography using distilled Hexane to yield the pure product (67.13%). The product obtained was oily so a salt of the compound was prepared.

Procedure for oxalate salt formation: Oxalic acid, 1 mmole/1 mmole of compound, (83.3 mg) and oily product (250 mg) were dissolved in dry methanol separately into two round bottom flasks. The acid and the compound were mixed and shaken thoroughly. The salt was precipitated using dry diethyl ether, filtered, washed with the same and collected. Yield: 260 mg, 64.35%.

M.P. (Oxalate Salt of compound)=101° C., ESI MS (m/z)=379 (M+H); IR (KBr, Cm$^{-1}$)=3020.7, 2361.4, 1761.8, 1631.9, 1525.6, 1426.5, 1216.1, 761.0, 670.3; $^1$H NMR(300MHz, CDCl$_3$): δ=7.9240(d, J=7.8 Hz, 2H, ArH) 7.6788(d, J=8.2 Hz, 1H, ArH), 7.5763-7.3997(m, 5H, ArH), 7.3223-7.2806(m, 1H, ArH), 7.1766(d, J=8.4Hz, 2H, ArH), 4.0737-4.0187(m, 1H, OCH), 3.0861-2.8784(m, 2H, NCH$_2$), 2.4656(s, 3H, SCH$_3$), 2.1236(s, 6H, NCH$_3$), 0.9154 (d, J=6.0 Hz, 3H, CH—CH$_3$); Analysis calculated for C$_{23}$H$_{26}$N$_2$OS(free base): C, 72.98; H, 6.92; N, 7.40, found: C, 72.93; H, 6.88; N, 7.37.

Method B: Into a 50 ml round bottom flask, 4-(methylthio)phenyl (naphthalen-1-yl)methanone oxime (1 mmole, 293 mg), (2-Chloro-propyl)-dimethyl-amine hydrochloride (1.2 mmole, 189.6 mg), baked K$_2$CO$_3$ (5 mmole, 690 mg) and dry acetone (10.0 ml) were taken. The reaction mixture was refluxed under anhydrous conditions for 6 hours. The reaction was followed by TLC monitoring. After completion of the reaction, K$_2$CO$_3$ was filtered off and washed with acetone (2×10 ml). Filtrate was concentrated and the crude product was purified by basic alumina column chromatography using distilled Hexane to yield the pure product (250 mg, 66.13%).

Example 11

Synthesis of (4-(methylthio)phenyl)(naphthalen-1-yl)methanone O-2-(azepan-1-yl)ethyl oxime oxalate (Compound 5h)

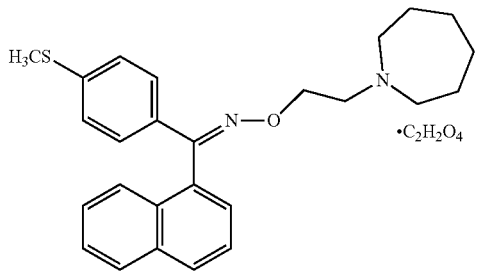

Into a 50 ml round bottom flask, 4-(methylthio)phenyl (naphthalen-1-yl)methanone oxime (1 mmole, 293 mg), 1-(2-Chloro-ethyl)-azepane hydrochloride (1.2 mmole, 237.6 mg), baked K$_2$CO$_3$ (5 mmole, 690 mg) and dry acetone (10.0 ml) were taken. The reaction mixture was refluxed under anhydrous conditions for 6 hours. The reaction was followed by TLC monitoring. After completion of the reaction, K$_2$CO$_3$ was filtered off and washed with acetone (2×10 ml). Filtrate was concentrated and the crude product was purified by basic alumina column chromatography using distilled Hexane to yield the pure product (350 mg, 83.7%). The product obtained was oily so a salt of the compound was prepared.

Procedure for oxalate salt formation: Oxalic acid, 1 mmole/1 mmole of compound, (105.5 mg) and oily product (350 mg) were dissolved in dry methanol separately into two round bottom flasks. The acid and the compound were mixed and shaken thoroughly. The salt was precipitated using dry diethyl ether, filtered, washed with the same and collected. Yield: 427 mg, 78.49%.

M.P. (Oxalate Salt of compound)=145° C.; ESI MS(m/z)=419 (M+H);); IR (KBr, Cm$^{-1}$): 3444.7, 2931.2, 2604.7, 1921.2, 1741.9, 1430.3, 1246.1, 1095.6, 1066.0, 961.0, 777.3; $^1$H NMR(300MHz, CDCl$_3$): δ=7.93 (d, J=8.2 Hz, 2H, ArH), 7.68(d, J=8.2 Hz, 1H, ArH), 7.58-7.39(m, 5H, ArH), 7.33-7.28(m, 1H, ArH), 7.18(d, J=8.6 Hz, 2H, ArH), 4.28(t, J=6.1 Hz, 2H, OCH$_2$), 2.78(t, J=0.5 Hz, 2H, NCH$_2$), 2.51(m, 4H, NCH$_2$), 2.47(s, 3H, SCH$_3$), 1.49(m, 8H, CH$_2$); Analysis Calculated for C$_{26}$H$_{30}$N$_2$OS (free base): C, 74.60; H, 7.22; N, 6.69, found: C, 74.62; H, 7.20; N, 6.68.

Example 12

Synthesis of (4-(methylthio)phenyl)(naphthalen-1-yl)methanone O-2-(diethylamino)ethyl oxime citrate (Compound 5i)

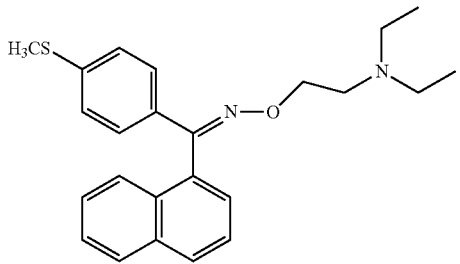

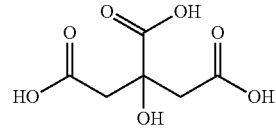

Procedure for citrate salt formation: citric acid, 1 mmole/1 mmole of compound, (122.45 mg) and (4-(methylthio)phenyl)(naphthalen-1-yl)methanone O-2-(diethylamino)ethyl oxime (250 mg) were dissolved in dry methanol separately into two round bottom flasks. The acid and the compound were mixed and shaken thoroughly and kept in refrigerator for overnight after adding dry diethyl ether. The salt was filtered, washed with dry diethyl ether and collected. Yield: 49%. Analysis calculated for C$_{30}$H$_{36}$N$_2$O$_8$SC, 61.63; H, 6.21; N, 4.79; found: C, 61.62; H, 6.17; N, 4.75.

Example 13

Synthesis of (4-(methylthio)phenyl)(naphthalen-1-yl)methanone O-2-(diethylamino)ethyl oxime fumarate (Compound 5j)

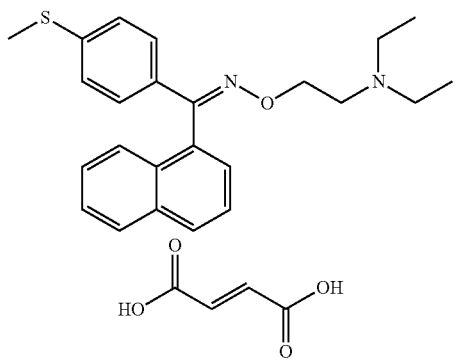

Procedure for fumarate salt formation: fumaric acid, 1 mmole/1 mmole of compound, (73.98 mg) and (4-(methylthio)phenyl)(naphthalen-1-yl)methanone O-2-(diethylamino)ethyl oxime (250 mg) were dissolved in dry methanol separately into two round bottom flasks. The acid and the compound were mixed and shaken thoroughly and kept in refrigerator for overnight after adding dry diethyl ether. The salt was filtered, washed with dry diethyl ether and collected. Yield: 48.3%. Analysis calculated for $C_{28}H_{32}N_2O_5S$, C, 66.12; H, 6.34; N, 5.51; found: C, 66.13; H, 6.37; N, 5.55.

Example 14

Synthesis of (4-(methylthio)phenyl)(naphthalen-1-yl)methanone O-2-(diethylamino)ethyl oxime tartrate (Compound 5k)

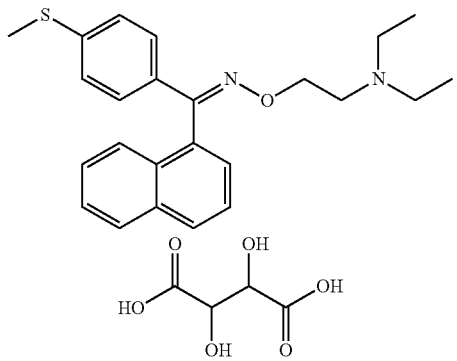

Procedure for tartrate salt formation: tartric acid, 1 mmole/1 mmole of compound, (95.66 mg) and (4-(methylthio)phenyl)(naphthalen-1-yl)methanone O-2-(diethylamino)ethyl oxime (250 mg) were dissolved in dry methanol separately into two round bottom flasks. The acid and the compound were mixed and shaken thoroughly and kept in refrigerator for overnight after adding dry diethyl ether. The salt was filtered, washed with dry diethyl ether and collected. Yield: 51%. Analysis calculated for $C_{28}H_{34}N_2O_7S$, C, 61.97; H, 6.32; N, 5.16; found: C, 61.93; H, 6.30; N, 5.11.

Example 15

Synthesis of (4-(methylthio)phenyl)(naphthalen-1-yl)methanone O-2-(diethylamino)ethyl oxime (Compound 5l)

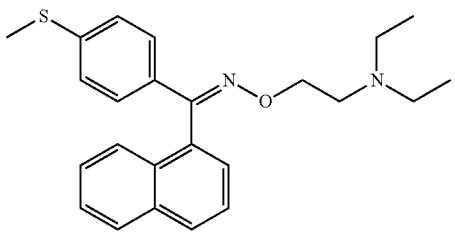 [SMILES: CCN(CC)CCO/N=C(/c1ccc(SC)cc1)c1cccc2ccccc12]

Into a 50 ml round bottom flask, 4-(methylthiophenyl)(naphthalen-1-yl)methanone oxime (1 mmole, 293 mg), 2-chloro-N,N-diethylethanamine hydrochloride (1.2 mmole, 205 mg), baked $K_2CO_3$ (5 mmole, 690 mg) and dry acetone (10.0 ml) were taken. The reaction mixture was refluxed under anhydrous conditions for 6 hours. The reaction was followed by TLC monitoring. After completion of the reaction, $K_2CO_3$ was filtered off and washed with acetone (2×10 ml). Filtrate was concentrated and the crude product was purified by basic alumina column chromatography using distilled Hexane to yield the pure product (250 mg, 63.6%). The product obtained was oily so a salt of the compound was prepared. ESI MS (m/z)=393 (M+H); IR (KBr, $Cm^{-1}$): 3445.9, 2939.4, 2362.7, 1742.4, 1645.1, 1400.5, 1235.1, 964.2, 718.3; NMR($CDCl_3$, 200MHz): δ=7.93(d, J=8.0 Hz, 2H, ArH), 7.63-7.41(m, 5H, ArH), 7.27-7.25(m, 2H, ArH), 7.17-7.13(d, J=8.0 Hz, 2H, ArH), 4.48(m, 2H, $OCH_2$), 3.26(m, 2H, $NCH_2$), 2.72(m, 4H, $NCH_2$), 2.46(s, 3H, $SCH_3$), 0.81(m, 6H, $CH_3$); Analysis calculated for $C_{24}H_{28}N_2OS$: C, 73.43; H, 7.19; N, 7.14, found: C, 73.41; H, 7.15; N, 7.10.

Example 16

Synthesis of (4-(methylthio)phenyl)(naphthalen-1-yl)methanone O-3-(dimethylamino)propyl oxime oxalate (Compound 5m)

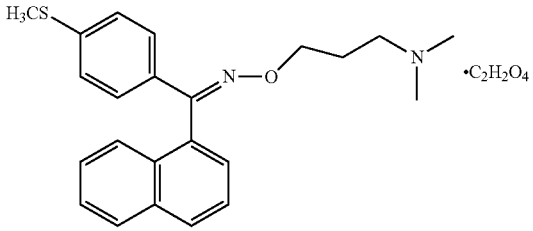

Into a 50 ml round bottom flask, 4-(methylthiophenyl)(naphthalen-1-yl)methanone oxime (1 mmole, 293 mg), 3-chloro-N,N-dimethylpropan-1-amine hydrochloride (1.2 mmole, 190 mg), baked $K_2CO_3$ (5 mmole, 690 mg) and dry acetone (10.0 ml) were taken. The reaction mixture was refluxed under anhydrous conditions for 6 hours. The reaction was followed by TLC monitoring. After completion of the reaction, $K_2CO_3$ was filtered off and washed with acetone (2×10 ml). Filtrate was concentrated and the crude product was purified by basic alumina column chromatography using distilled Hexane to yield the pure product (240 mg, 63.5%). The product obtained was oily so a salt of the compound was prepared.

Procedure for oxalate salt formation: Oxalic acid, 1 mmole/1 mmole of compound, (80 mg) and oily product (240 mg) were dissolved in dry methanol separately into two round bottom flasks. The acid and the compound were mixed and shaken thoroughly. The salt was precipitated using dry diethyl ether, filtered, washed with the same and collected. Yield: 251 mg, 49.8%.

M.P. (Oxalate Salt of compound)=110° C.; ESI MS (m/z)=379 (M+H); IR (KBr, Cm$^{-1}$): 3448.1, 2938.1, 2682.5, 1621.9, 1471.4, 1240.3, 1048.1, 719.1; $^1$H NMR (CD$_3$OD, 200MHz): δ=7.97 (d, J=8.2 Hz, 2H, ArH), 7.60-7.44(m, 5H, ArH), 7.39-7.26(m, 2H, ArH), 7.16 (d, J=8.0 Hz, 2H, ArH), 4.21-4.16(t, J=5.6 Hz 2H, OCH$_2$), 2.90-2.85 (m, 2H, NCH$_2$), 2.63(s, 6H, NCH$_3$), 2.43(s, 3H, SCH$_3$), 2.02-1.96(m, 2H, CH$_2$); Analysis calculated for C$_{23}$H$_{26}$N$_2$OS(Free base): C, 72.98; H, 6.92; N, 7.40, found: C, 72.95; H, 6.89; N, 7.38.

Example 17

Synthesis of (4-(methylthio)phenyl)(naphthalen-1-yl)methanone O-3-chloropropyl oxime (Compound 5n)

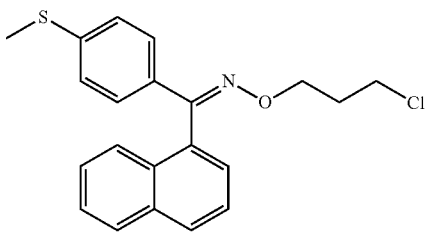 [SMILES: CSc1ccc(/C(=N/OCCCCl)c2cccc3ccccc23)cc1]

Into a 50 ml round bottom flask, 4-(methylthiophenyl) (naphthalen-1-yl)methanone oxime (2 mmole, 586 mg), 1-bromo-3-chloropropane (4 mmole, 0.39 ml), baked K$_2$CO$_3$ (10 mmole, 1380 mg) and dry acetone (15.0 ml) were taken. The reaction mixture was refluxed under anhydrous conditions for 8 hours. The reaction was followed by TLC monitoring. After completion of the reaction, K$_2$CO$_3$ was filtered off and washed with acetone (2×10 nil). Filtrate was concentrated and the crude product was purified by silica gel column chromatography using distilled Hexane to yield the pure product (510 mg, 69.11%).

Oily compound, ESI MS(m/z)=370 (M+H); IR(Neat, Cm$^{-1}$): 3464.5, 3055.8, 1594.0, 1493.4, 1437.8, 1314.6, 1217.4, 1095.5, 1042.5, 964.0, 758.3; (200 MHz, CDCl$_3$): δ=7.92 (d, J=6 Hz, 2H, ArH), 7.66-7.41(m, 6H, ArH), 7.32-7.26(m, 1H, ArH), 7.17 (d, J=8 Hz, 2H, ArH), 4.28(t, J=4.9 Hz, 2H, OCH$_2$), 3.42(t, J=6.7 Hz, 2H, CH$_2$Cl), 2.46(s, 3H, SCH$_3$), 2.10-2.04(m, 2H, CH$_2$); Analysis calculated for C$_{21}$H$_{20}$ClNOS: C, 68.19; H, 5.45; N, 3.79, found: C, 68.21; H, 5.44; N, 3.80.

Example 18

Synthesis of (4-(methylthio)phenyl)(naphthalen-1-yl)methanone O-4-chlorobutyl oxime (Compound 5o)

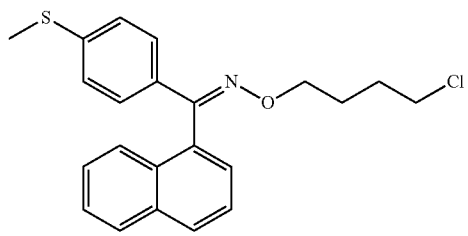 [SMILES: CSc1ccc(/C(=N/OCCCCCl)c2cccc3ccccc23)cc1]

Into a 50 ml round bottom flask 4-(methylthiophenyl) (naphthalen-1-yl)methanone oxime (2 mmole, 586 mg), 1-bromo-4-chlorobutane (4 mmole, 0.46 ml), baked K$_2$CO$_3$ (10 mmole, 1380 mg) and dry acetone (15.0 ml) were taken. The reaction mixture was refluxed under anhydrous conditions for 8 hours. The reaction was followed by TLC monitoring. After completion of the reaction, K$_2$CO$_3$ was filtered off and washed with acetone (2×10 nil). Filtrate was concentrated and the crude product was purified by silica gel column chromatography using distilled Hexane to yield the pure product (547 mg, 71.22%).

Oily compound, ESI MS (m/z)=385 (M+H); $^1$H (200MHz, CDCl$_3$): δ=7.92 (d, J=7.6 Hz, 2H, ArH), 7.55-7.39(m, 6H, ArH), 7.32-7.20(m, 1H, ArH), 7.17(d, J=8.5 Hz, 2H, ArH), 4.19(t, J=5.7 Hz, 2H, OCH$_2$), 3.42(t, J=6.5 Hz, 2H, CH$_2$Cl), 2.46(s, 3H, SCH$_3$), 1.79-1.61(m, 4H, CH$_2$); Analysis calculated for C$_{22}$H$_{22}$ClNOS: C, 68.82; H, 5.78; N, 3.65; found: C, 68.80; H, 5.76; N, 3.64.

Example 19

Synthesis of Ethyl 2-((4-(methylthio)phenyl) (naphthalen-1-yl) methyleneaminooxy) acetate (Compound 5p)

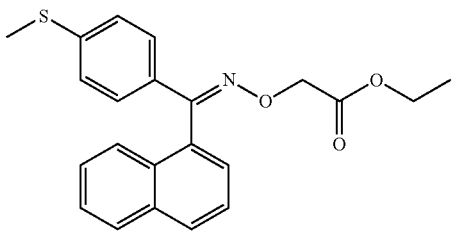 [SMILES: CCOC(=O)CO/N=C(/c1ccc(SC)cc1)c1cccc2ccccc12]

Into a 50 ml round bottom flask, 4-(methylthiophenyl) (naphthalen-1-yl)methanone oxime (1 mmole, 293 mg), ethyl-2-bromoacetate (1.2 mmole), baked K$_2$CO$_3$ (5 mmole) and dry acetone (10.0 ml) were taken. The reaction mixture was refluxed under anhydrous conditions for 6 hours. The reaction was followed by TLC monitoring. After completion of the reaction, K$_2$CO$_3$ was filtered off and washed with acetone (2×10 ml). Filtrate was concentrated and the crude product was purified by basic alumina column chromatography using distilled Hexane to yield the pure product (65.0%).

ESI MS (m/z)=393 (M+H); $^1$H NMR(CDCl$_3$, 300MHz): δ=7.93(d, J=6.0 Hz, 2H, ArH), 7.64-7.43(m, 7H, ArH), 7.16(d, J=6.0 Hz, 2H, ArH), 4.62(s, 1H, OCH$_2$), 4.16(q, J=12.0 Hz, 2H, OCH$_2$), 2.45(s, 3H, SCH$_3$), 1.34 (t, J=12.0 Hz, 3H, CH$_3$); Analysis calculated for C$_{22}$H$_{21}$NO$_3$S: C, 69.63; H, 5.58; N, 3.69; found: C, 69.60; H, 5.53; N, 3.66.

Example 20

Synthesis of N,N-diethyl-2-((4-(methylthio)phenyl) (naphthalen-1-yl)methyleneaminooxy)acetamide (Compound 5q)

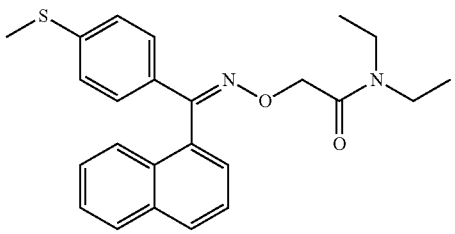 [SMILES: CCN(CC)C(=O)CO/N=C(/c1ccc(SC)cc1)c1cccc2ccccc12]

Into a microwave vial (2-5 cm), ethyl 2-((4-(methylthio) phenyl)(naphthalen-1-yl)methyleneaminooxy)acetate (379 mg, 1 mmole) and potassium tertiary butoxide (1 mmole) and diethylamine (1 mmole) was taken. The reaction mixture was then irradiated to microwave for 3 min. On completion of the reaction, the mixture was diluted with 15 ml of dichloromethane and extracted. It was then washed with brine, then with water and dried over anhydrous Na$_2$SO$_4$. The crude product was purified by silica gel column chromatography using 1% MeOH/CHCl$_3$ as eluent to yield the pure product. Yield: 54.3%. $^1$H NMR (CDCl$_3$, 300 MHz): δ=7.92(d, J=8.0 Hz, 2H, ArH), 7.70(d, J=9.0 Hz, 1H, ArH), 7.62-7.46(m, 6H, ArH), 7.36-7.31(m, 1H, ArH), 7.20(d, J=9.0 Hz, 2H, ArH), 4.71(s, 2H, OCH$_2$), 4.02(q, J=6.0 Hz, 4H, NCH$_2$), 2.50(s, 3H, SCH$_3$), 1.86(t, 6H, CH$_3$); Analysis calculated for C$_{24}$H$_{26}$N$_2$O$_2$S: C, 70.90; H, 6.45; N, 6.89; found: C, 70.95; H, 6.43; N, 6.84.

Example 21

Synthesis of (4-methoxyphenyl)(naphthalen-1-yl) methanone O-2-(piperidin-1-yl)ethyl oxime oxalate (Compound 6a)

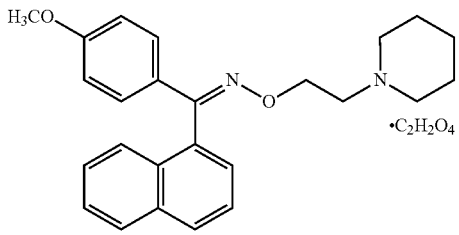

Into a 50 ml round bottom flask, (4-(methoxy phenyl) (naphthalen-1-yl)methanone oxime (1 mmole, 277 mg), 1-(2-chloroethyl)piperidine hydrochloride (1.2 mmole, 220.8 mg), baked K$_2$CO$_3$ (5 mmole, 690 mg) and dry acetone (10.0 ml) were taken. The reaction mixture was refluxed under anhydrous conditions for 6 hours. The reaction was followed by TLC monitoring. After completion of the reaction, K$_2$CO$_3$ was filtered off and washed with acetone (2×10 ml). The filtrate was concentrated and the crude product was purified by basic alumina column chromatography using distilled Hexane to yield the pure product (312 mg, 80.41%). The product obtained was oily so a salt of the compound was prepared.

Procedure for oxalate salt formation: Oxalic acid, 1 mmole/1 mmole of compound, (101.3 mg) and oily product (312 mg) were dissolved in dry methanol separately into two round bottom flasks. The acid and the compound were mixed and shaken thoroughly. The salt was precipitated using dry diethyl ether, filtered, washed with the same and collected. Yield: 364 mg, 70.82%.

M. P. (Oxalate Salt of compound)=171° C.; ESI MS (m/z): 389 (M+H), IR (KBr, Cm$^{-1}$): 3409.7, 3020.1, 2959.6, 2361.4, 1771.7, 1609.9, 1513.2, 1216.1, 1030.0, 761.0, 670.1. $^1$H NMR(CDCl$_3$, 300MHz): δ=7.92(d, J=8.0 Hz, 2H, ArH), 7.71(d, J=8.2 Hz, 1H, ArH), 7.58-7.42(m, 5H, ArH), 7.33-7.28(m, 1H, ArH), 6.84(d, J=8.8 Hz, 2H, ArH), 4.30(t, J=6.0 Hz, 2H, OCH$_2$), 3.80(s, 3H, OCH$_3$), 2.62(t, J=5.4 Hz, 2H, NCH$_2$), 2.25-2.23(m, 4H, NCH$_2$), 1.48-1.43(m, 4H, CH$_2$), 1.34-1.28(m, 2H, CH$_2$); Analysis calculated for C$_{25}$H$_{28}$N$_2$O$_2$ (free base): C, 77.29; H, 7.26; N, 7.21, found: C, 77.31; H, 7.30; N, 7.20.

Example 22

Synthesis of (4-methoxyphenyl)(naphthalen-1-yl) methanone O-2-(pyrrolidin-1-yl)ethyl oxime oxalate (Compound 6b)

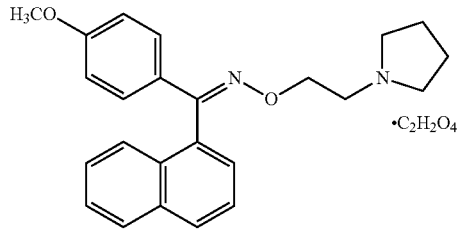

Into a 50 ml round bottom flask, (4-(methoxy phenyl) (naphthalen-1-yl)methanone oxime (1 mmole, 277 mg), 1-(2-chloroethyl)pyrrolidine hydrochloride (1.2 mmole, 204 mg), baked K$_2$CO$_3$ (5 mmole, 690 mg) and dry acetone (10.0 ml) were taken. The reaction mixture was refluxed under anhydrous conditions for 6 hours. The reaction was followed by TLC monitoring. After completion of the reaction, K$_2$CO$_3$ was filtered off and washed with acetone (2×10 ml). The filtrate was concentrated and the crude product was purified by basic alumina column chromatography using distilled Hexane to yield the pure product (262 mg, 69.87%). The product obtained was oily so a salt of the compound was prepared.

Procedure for oxalate salt formation: Oxalic acid, 1 mmole/1 mmole of compound, (88.02 mg) and oily product (262 mg) were dissolved in dry methanol separately into two round bottom flasks. The acid and the compound were mixed and shaken thoroughly. The salt was precipitated using dry diethyl ether, filtered, washed with the same and collected. Yield: 325 mg, 64.87%.

M. P. (Oxalate Salt of compound)=158° C.; ESI MS(m/z)=375 (M+H); IR (KBr, Cm$^{-1}$): 3450.2, 3020.0, 1758.1, 1629.6, 1216.0, 1045.5, 761.6, 669.7; $^1$H NMR(CDCl$_3$, 300MHz): δ=7.93(d, J=8.0 Hz, 2H, ArH), 7.73(d, J=9.8 Hz, 1H, ArH), 7.58-7.42(m, 5H, ArH), 6.84(d, J=8.7 Hz, 2H, ArH), 4.32(t, J=6.1 Hz, 2H, OCH$_2$), 3.75(s, 3H, OCH$_3$), 2.75-2.68(m, 2H, NCH$_2$), 2.47-2.44 (m, 4H, NCH$_2$), 1.66-1.57. (m, 4H, CH$_2$); Analysis calculated for C$_{24}$H$_{26}$N$_2$O$_2$ (free base): C, 76.98; H, 7.00; N, 7.48, found: C, 76.95; H, 7.03; N, 7.45.

Example 23

Synthesis of (4-methoxyphenyl)(naphthalen-1-yl)methanone O-2-(dimethylamino)ethyl oxime oxalate (Compound 6c)

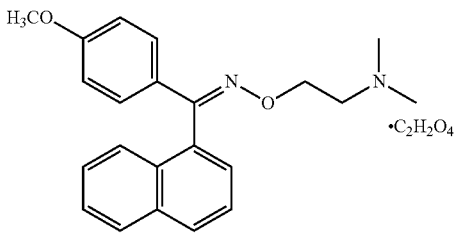

Into a 50 ml round bottom flask, 4-(methylthio)phenyl (naphthalen-1-yl)methanone oxime (1 mmole, 277 mg), (2-Chloro-ethyl)-dimethyl-amine hydrochloride (1.2 mmole, 172.8 mg), baked K$_2$CO$_3$ (5 mmole, 690 mg) and dry acetone (10.0 ml) were taken. The reaction mixture was refluxed under anhydrous conditions for 6 hours. The reaction was followed by TLC monitoring. After completion of the reaction, K$_2$CO$_3$ was filtered off and washed with acetone (2×10 ml). The filtrate was concentrated and the crude product was purified by basic alumina column chromatography using distilled Hexane to yield the pure product (281 mg, 80.8%). The product obtained was oily so a salt of the compound was prepared.

Procedure for oxalate salt formation: Oxalic acid, 1 mmole/1 mmole of compound, (101.8 mg) and oily product (281 mg) were dissolved in dry methanol separately into two round bottom flasks. The acid and the compound were mixed and shaken thoroughly. The salt was precipitated using dry diethyl ether, filtered, washed with the same and collected. Yield: 329 mg, 69.4%.

M. P. (Oxalate Salt of compound)=141° C.; ESI MS (m/z)=349 (M+H), IR (KBr, Cm$^{-1}$): 3443.3, 3019.8, 2962.4, 2361.6, 1756.8, 1627.5, 1510.3, 1466.8, 1216.5, 1032.0, 761.1, 670.0; $^1$H NMR(CDCl$_3$, 200 MHz): δ=7.92(m, 2H, ArH), 7.61-7.37(m, 6H, ArH), 7.31-7.26(m, 1H, ArH), 6.84 (d, J=6.8 Hz, 2H, ArH), 4.49(t, J=4.6 Hz, 2H, OCH$_2$), 3.78(s, 3H, OCH$_3$), 3.29-3.27(m, 2H, NCH$_2$), 2.46(s, 6H, NCH$_3$). Analysis calculated for C$_{22}$H$_{24}$N$_2$O$_2$ (free base): C, 75.83; H, 6.94; N, 8.04, Found: C, 75.80; H, 6.90; N, 8.00.

Example 24

Synthesis of (4-methoxyphenyl)(naphthalen-1-yl)methanone O-2-(diethylamino)ethyl oxime oxalate (Compound 6d)

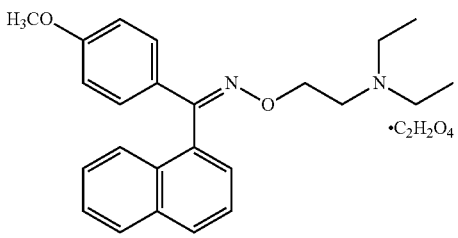

Into a 50 ml round bottom flask, (4-(methoxy phenyl)(naphthalen-1-yl)methanone oxime (1 mmole, 277 mg), 2-chloro-N,N-diethylethanamine hydrochloride (1.2 mmole, 205 mg), baked K$_2$CO$_3$ (5 mmole, 690 mg) and dry acetone (10.0 ml) were taken. The reaction mixture was refluxed under anhydrous conditions for 6 hours. The reaction was followed by TLC monitoring. After completion of the reaction, K$_2$CO$_3$ was filtered off and washed with acetone (2×10 ml). The filtrate was concentrated and the crude product was purified by basic alumina column chromatography using distilled Hexane to yield the pure product (289 mg, 76.86%). The product obtained was oily so a salt of the compound was prepared.

Procedure for oxalate salt formation: Oxalic acid, 1 mmole/1 mmole of compound, (96.85 mg) and oily product (289 mg) were dissolved in dry methanol separately into two round bottom flasks. The acid and the compound were mixed and shaken thoroughly. The salt was precipitated using dry diethyl ether, filtered, washed with the same and collected. Yield: 295 mg, 58.78%.

M.P. (Oxalate Salt of compound)=137° C.; ESI MS(m/z)=377 (M+H), IR (KBr, Cm$^{-1}$): 3445.4, 2940.8, 2645.9, 1900.0, 1607.6, 1510.1, 1313.4, 1249.4, 1177.5, 1030.3, 963.3, 717.1; NMR(CDCl$_3$, 200MHz): δ=7.91(d, J=8.1 Hz, 2H, ArH), 7.69(d, J=8.2 Hz, 1H, ArH), 7.57-7.39 (m, 5H, ArH), 7.32-7.26(m, 1H, ArH), 6.83(d, J=7.1 Hz, 2H, ArH), 4.25(t, J=6.3 Hz, 2H, OCH$_2$), 3.78(s, 3H, OCH$_3$), 2.74(t, J=5.9 Hz, 2H, NCH$_2$), 2.45-2.34(q, J=7.2 Hz, 4H, CH$_2$), 0.88(t, J=7.2 Hz, 6H, CH$_3$); Analysis calculated for C$_{24}$H$_{28}$N$_2$O$_2$: C, 76.56; H, 7.50; N, 7.44, found: C, 76.53; H, 7.52; N, 7.42.

Example 25

Synthesis of (4-methoxyphenyl)(naphthalen-1-yl)methanone O-2-(diisopropylamino)ethyl oxime oxalate (Compound 6e)

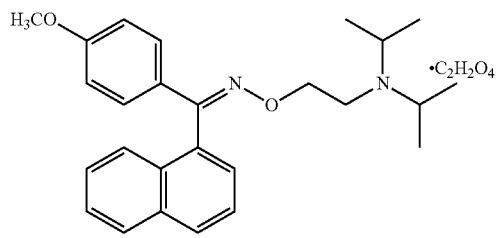

Into a 50 ml round bottom flask, 4-(methoxy phenyl)(naphthalen-1-yl)methanone oxime (1 mmole, 277 mg), (2-Chloro-ethyl)-diisopropyl-amine hydrochloride (1.2 mmole, 240 mg), baked K$_2$CO$_3$ (5 mmole, 690 mg) and dry acetone (10.0 ml) were taken. The reaction mixture was refluxed under anhydrous conditions for 6 hours. The reaction was followed by TLC monitoring. After completion of the reaction, K$_2$CO$_3$ was filtered off and washed with acetone (2×10 ml). The filtrate was concentrated and the crude product was purified by basic alumina column chromatography using distilled Hexane to yield the pure product (318 mg, 78.71%). The product obtained was oily so a salt of the compound was prepared.

Procedure for oxalate salt formation: Oxalic acid, 1 mmole/1 mmole of compound, (99.18 mg) and oily product (318 mg) were dissolved in dry methanol separately into two round bottom flasks. The acid and the compound were mixed and shaken thoroughly. The salt was precipitated using dry diethyl ether, filtered, washed with the same and collected. Yield: 331 mg, 62.45%.

M.P. (Oxalate Salt of compound)=130° C.; ESI MS(m/z)=405 (M+H), IR (KBr, Cm$^{-1}$): 3445.3, 2977.4, 2691.6, 1748.4, 1638.8, 1508.0, 1394.7, 1252.6, 1178.0, 966.1, 777.6; $^1$H NMR(CDCl$_3$, 200MHz): δ=7.92(d, J=8.1 Hz, 2H, ArH), 7.69 (d, J=8.0 Hz, 1H, ArH), 7.58-7.40(m, 5H, ArH), 7.33-7.29(m, 1H, ArH), 6.83(d, J=6.9 Hz, 2H, ArH) 4.09(t, J=7.3 Hz, 2H, OCH$_2$), 3.79(s, 3H, OCH$_3$), 2.98-2.85(m, 2H, NCH), 2.69-2.60(m, 2H, NCH$_2$), 0.94(d, J=6.5 Hz, 12H, OHCH$_3$); Analysis calculated for C$_{26}$H$_{32}$N$_2$O$_2$: C, 77.19; H, 7.97; N, 6.92, found: C, 77.24; H, 7.99; N, 6.90.

Example 26

Synthesis of (4-methoxyphenyl)(naphthalen-1-yl) methanone O-1-(dimethylamino)propan-2-yl oxime oxalate (Compound 6f)

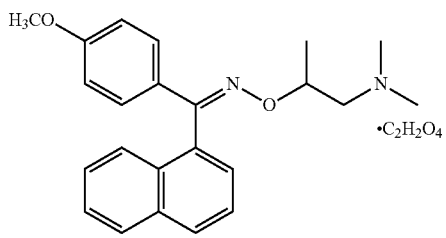

Into a 50 ml round bottom flask, 4-(methoxy phenyl (naphthalen-1-yl)methanone oxime (1 mmole, 277 mg), (2-Chloro-propyl)-dimethyl-amine hydrochloride (1.2 mmole, 189.6 mg), baked K$_2$CO$_3$ (5 mmole, 690 mg) and dry acetone (10.0 ml) were taken. The reaction mixture was refluxed under anhydrous conditions for 6 hours. The reaction was followed by TLC monitoring. After completion of the reaction, K$_2$CO$_3$ was filtered off and washed with acetone (2×10 ml). Filtrate was concentrated and the crude product was purified by basic alumina column chromatography using distilled Hexane to yield the pure product (270 mg, 74.59%). The product obtained was oily so a salt of the compound was prepared.

Procedure for oxalate salt formation: Oxalic acid, 1 mmole/1 mmole of compound, (93.98 mg) and oily product (270 mg) were dissolved in dry methanol separately into two round bottom flasks. The acid and the compound were mixed and shaken thoroughly. The salt was precipitated using dry diethyl ether, filtered, washed with the same and collected. Yield: 250 mg, 51.23%.

M.P. (Oxalate Salt of compound)=105° C.; ESI MS(m/z)=363 (M+H), IR (KBr, Cm$^{-1}$): 3746.4, 2931.5, 1754.4, 1694.1, 1629.4, 1559.5, 1511.4, 1462.6, 1252.0, 1176.7, 962.8, 739.5; $^1$H NMR (200MHz, CDCl$_3$): δ=7.91 (d, J=8.8 Hz, 2H, ArH), 7.69(d, J=8.1 Hz, 1H, ArH), 7.54-7.39(m, 5H, ArH), 7.32-7.26(m, 2H, ArH & CHCl$_3$), 6.83(m, 2H, ArH), 4.00-3.97(m, 1H, OCH), 3.80(s, 3H, OCH$_3$), 2.09(s, 6H, NCH$_3$), 0.85(d, J=6.6 Hz, 3H, CH—CH$_3$); Analysis calculated for C$_{23}$H$_{26}$N$_2$O$_2$: C, 76.21; H, 7.23; N, 7.73, found: C, 76.21; H, 7.23; N, 7.73.

Example 27

Synthesis of (4-methoxyphenyl)(naphthalen-1-yl) methanone O-2-(azepan-1-yl)ethyl oxime oxalate (Compound 6g)

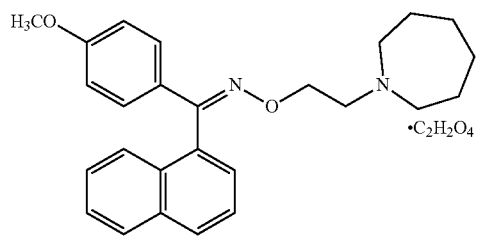

Into a 50 ml round bottom flask, 4-(methoxy phenyl (naphthalen-1-yl)methanone oxime (1 mmole, 277 mg), 1-(2-Chloro-ethyl)-azepane hydrochloride (1.2 mmole, 237.6 mg), baked K$_2$CO$_3$ (5 mmole, 690 mg) and dry acetone (10.0 ml) were taken. The reaction mixture was refluxed under anhydrous conditions for 6 hours. The reaction was followed by TLC monitoring. After completion of the reaction, K$_2$CO$_3$ was filtered off and washed with acetone (2×10 ml). Filtrate was concentrated and the crude product was purified by basic alumina column chromatography using distilled Hexane to yield the pure product (312 mg, 77.61%). The product obtained was oily so a salt of the compound was prepared.

Procedure for oxalate salt formation: Oxalic acid, 1 mmole/1 mmole of compound, (97.79 mg) and oily product (312 mg) were dissolved in dry methanol separately into two round bottom flasks. The acid and the compound were mixed and shaken thoroughly. The salt was precipitated using dry diethyl ether, filtered, washed with the same and collected. Yield: 331 mg, 62.69%.

M.P. (Oxalate Salt of compound)=122° C.; ESI MS(m/z)=403 (M+H), IR (KBr, Cm$^{-1}$): 3446.5, 2933.9, 2599.9, 1721.6, 1607.9, 1510.2, 1459.5, 1251.3, 1177.9, 1026.7, 960.1, 719.2; $^1$H NMR (300MHz, CDCl$_3$): δ=7.92 (d, J=8.0 Hz, 2H, ArH), 7.69(d, J=8.2 Hz, 1H, ArH), 7.58-7.39(m, 5H, ArH), 7.33-7.28(m, 1H, ArH), 6.84(d, 3=8.5 Hz, 2H, ArH), 4.27(t, J=6.1 Hz, 2H, OCH$_2$), 3.80(s, 3H, OCH$_3$), 2.78-2.67(m, 2H NCH$_2$), 2.51(m, 4H NCH$_2$), 1.49(m, 8H, CH$_2$); Analysis calculated for C$_{26}$H$_{30}$N$_2$O$_2$: C, 77.58; H, 7.51; N, 6.96; found: C, 77.55; H, 7.53; N, 6.95.

Example 28

Synthesis of (4-methoxyphenyl)(naphthalen-1-yl) methanone O-2-morpholinoethyl oxime (Compound 6h)

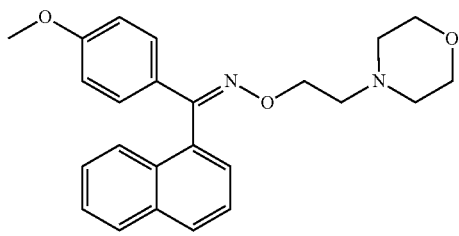 [SMILES: COc1ccc(/C(=N/OCCN2CCOCC2)c2cccc3ccccc23)cc1]

Into a 50 ml round bottom flask, 4-(methoxy phenyl)(naphthalen-1-yl)methanone oxime (1 mmole), 1-(2-Chloroethyl)-morpholine hydrochloride (1.2 mmole), baked $K_2CO_3$ (5 mmole) and dry acetone (10.0 ml) were taken. The reaction mixture was refluxed under anhydrous conditions for 4 hours. The reaction was followed by TLC monitoring. After completion of the reaction, $K_2CO_3$ was filtered off and washed with acetone (2×10 ml). Filtrate was concentrated and the crude product was purified by basic alumina column chromatography using distilled Hexane to yield the pure product (78.5%).

ESI MS(m/z)=391 (M+H), NMR (300MHz, $CDCl_3$): δ=7.94 (d, J=8.22Hz, 2H, ArH), 7.66-7.43 (m, 6H, ArH), 7.31(m, 1H, ArH), 6.86(d, J=8.9 Hz, 2H, ArH), 4.47(br, s, 2H, $OCH_3$), 3.81(s, 3H, $OCH_3$), 3.60-3.53(m, 4H, $OCH_2$), 3.25-3.24(m, 2H, $OCH_2$), 2.71(broad, 6H $NCH_2$); Analysis calculated for: $C_{24}H_{26}N_2O_3$: C, 73.85; H, 6.73; N, 7.20; found: C, 73.82; H, 6.71; N, 7.17.

Example 29

Synthesis of (4-methoxyphenyl)(naphthalen-1-yl) methanone O-3-(dimethylamino)propyl oxime oxalate (Compound 6i)

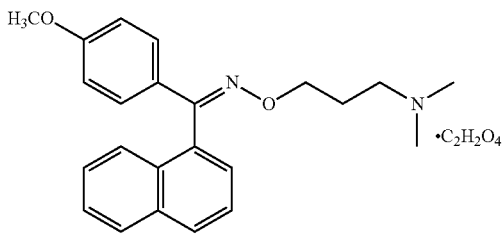

Into a 50 ml round bottom flask (4-(methoxy phenyl)(naphthalen-1-yl)methanone oxime (1 mmole, 277 mg), 3-chloro-N,N-dimethylpropan-1-amine hydrochloride (1.2 mmole, 190 mg), baked $K_2CO_3$ (5 mmole, 690 mg) and dry acetone (10.0 ml) were taken. The reaction mixture was refluxed under anhydrous conditions for 6 hours. The reaction was followed by TLC monitoring. After completion of the reaction, $K_2CO_3$ was filtered off and washed with acetone (2×10 ml). Filtrate was concentrated and the crude product was purified by basic alumina column chromatography using distilled Hexane to yield the pure product (253 mg, 69.89%). The product obtained was oily so the salt of the compound was prepared.

Procedure for oxalate salt formation: Oxalic acid, 1 mmole/1 mmole of compound, (88.06 mg) and oily product (253 mg) were dissolved in dry methanol separately into two round bottom flasks. The acid and the compound were mixed and shaken thoroughly. The salt was precipitated using dry diethyl ether, filtered, washed with the same and collected. Yield: 250 mg, 65.96%.

M.P. (Oxalate Salt of compound)=155° C.; ESI MS(m/z)=363 (M+H), IR (KBr, $Cm^{-1}$): 3446.3, 3045.6, 2957.4, 2680.0, 2470.8, 1741.9, 1602.8, 1510.0, 1251.9, 1177.4, 1043.6, 719.1; $^1$H NMR (200MHz, $CDCl_3$): δ=7.92 (d, J=7.7 Hz, 2H, ArH), 7.69(d, J=8.0 Hz, 1H, ArH), 7.63-7.44(m, 5H, ArH), 7.32-7.28(m, 2H, ArH), 6.83(d, J=8.4 Hz, 2H, ArH), 4.17(t, J=6.0 Hz, 2H, $OCH_2$), 3.80(s, 3H, $OCH_3$), 2.65(m, 2H, $NCH_2$), 2.12(s, 2H, $NCH_3$), 1.78 (m, 2H, $CH_2$). Analysis calculated for $C_{23}H_{26}N_2O_2$: C, 76.21; H, 7.23; N, 7.73; Found: C, 76.20; H, 7.25; N, 7.70.

Example 30

Synthesis of (4-methoxyphenyl)(naphthalen-1-yl) methanone O-3-chloropropyl oxime (Compound 6j)

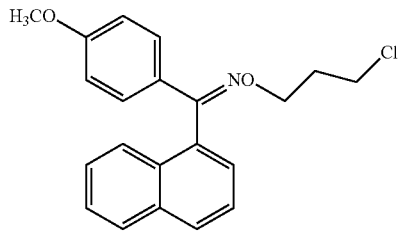

Into a 50 ml round bottom flask, (4-Methoxy-phenyl)-naphthalen-1-yl-methanone oxime (2 mmole, 526.58 mg), 1-bromo-3-chloropropane (4 mmole, 0.39 ml), baked $K_2CO_3$ (10 mmole, 1380 mg) and dry acetone (15.0 ml) were taken. The reaction mixture was refluxed under anhydrous conditions for 8 hours. The reaction was followed by TLC monitoring. After completion of the reaction, $K_2CO_3$ was filtered off and washed with acetone (2×10 ml). Filtrate was concentrated and the crude product was purified by silica gel column chromatography using 30% chloroform/Hexane to yield the pure product (614 mg, 86.7%).

Oily compound, ESI MS(m/z)=354 (M+H); $^1$H NMR (200MHz, $CDCl_3$): δ=7.93(d, J=8.0 Hz, 2H, ArH), 7.70(m, 1H, ArH), 7.64-7.45(m, 5H, ArH), 7.33-7.29(m, 2H, ArH), 6.84(d, J=4.0 Hz, 2H, ArH), 4.29(t, J=5.7 Hz, 2H, $OCH_2$), 3.42-3.35(m, 2H, $CH_2Cl$), 3.79(s, 3H, $OCH_3$), 2.14-2.01(m, 2H,$CH_2$); Analysis calculated for $C_{21}H_{20}ClNO_2$: C, 71.28; H, 5.70; N, 3.96; found: C, 71.32; H, 5.75; N, 3.90.

Example 31

Synthesis of (4-methoxyphenyl)(naphthalen-1-yl) methanone O-3-(piperidin-1-yl)propyl oxime (Compound 6k)

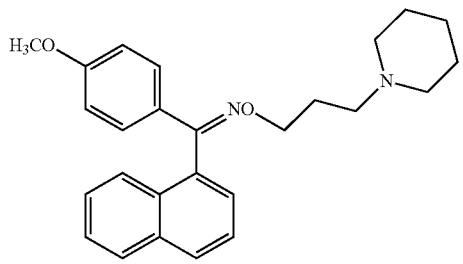

Into a 50 ml round bottom flask, (4-Methoxy-phenyl)-naphthalen-1-yl-methanone O-(3-chloro-propyl)-oxime (1 mmole, 353 mg), Piperidine (5 mmole, 0.49 ml) and dry methanol (10.0 ml) were taken. The reaction mixture was refluxed under anhydrous conditions for 6 hours. The reaction was followed by TLC monitoring. After completion of the reaction, methanol was evaporated under reduced pressure. The resulting mixture was poured onto water and extracted with ethyl acetate (3×50 ml), washed with water, dried over anhydrous Na₂SO₄ and concentrated. The crude product was purified by basic alumina column chromatography using distilled Hexane to yield the pure product (289 mg, 69.1%).

Oily Compound; ESI MS (m/z)=403 (M+H); $^1$H NMR (200MHz, CDCl₃): δ=7.93(d, J=8 Hz, 2H, ArH), 7.70(d, J=4 Hz, 1H, ArH), 7.64-7.45(m, 5H, ArH), 7.33-7.29(m, 1H, ArH), 6.84(d, J=4 Hz, 2H, ArH), 4.13-4.15(m, 2H, OCH₂), 3.8(s, 3H, OCH₃), 3.75(m, 2H, NCH₂), 3.34(m, 2H, NCH₂), 2.70-2.58(m, 2H, NCH₂), 2.10-1.71(m, 8H, CH₂). Analysis calculated for C₂₁H₂₀ClNO₂: C, 77.58; H, 7.51; N, 6.96; found: C, 77.55; H, 7.50; N, 6.89.

Example 32

Synthesis of (4-(methylthio)phenyl)(naphthalen-1-yl)methanone O-3-(piperidin-1-yl)propyl oxime oxalate (Compound 7a)

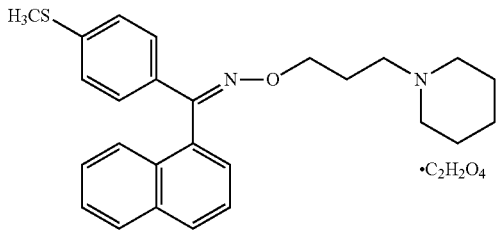

Into a 50 ml round bottom flask, 4-(methylthiophenyl) (naphthalen-1-yl)methanone O-3-chloropropyl oxime (1 mmole, 369 mg), piperidine (5 mmole, 0.49 ml) and dry methanol (10.0 ml) were taken. The reaction mixture was refluxed under anhydrous conditions for 6 hours. The reaction was followed by TLC monitoring. After completion of the reaction, methanol was evaporated under reduced pressure. The resulting mixture was poured onto water and extracted with ethyl acetate (3×50 ml), washed with water, dried over anhydrous Na₂SO₄ and concentrated. The crude product was purified by basic alumina column chromatography using distilled Hexane to yield the pure product (335 mg, 75.59%). The product obtained was oily so a salt of the compound was prepared.

Procedure for oxalate salt formation: Oxalic acid, 1 mmole/1 mmole of compound, (100.7 mg) and oily product (335 mg) were dissolved in dry methanol separately into two round bottom flasks. The acid and the compound were mixed and shaken thoroughly. The salt was precipitated using dry diethyl ether, filtered, washed with the same and collected. Yield: 395 mg, 90.65%.

M.P. (Oxalate Salt of compound)=137° C.; ESI MS (m/z)=419 (M+H); IR (KBr, Cm⁻¹): 3854, 3740, 3443, 2925, 2358, 1753, 1633, 1553, 1220, 760; $^1$H NMR (300MHz, CDCl₃): δ=7.93(d, J=8.2 Hz, 2H, ArH), 7.64-7.38(m, 6H, ArH), 7.30(m, 1H, ArH), 7.16(d, J=8.0 Hz, 2H, ArH), 4.13(m, 2H, OCH₂), 3.75(m, 2H, NCH₂), 3.34(m, 2H, NCH₂), 2.70-2.58(m, 2H, NCH₂), 2.45(s, 3H, SCH₃), 2.10-1.71(m, 8H, CH₂). Analysis calculated for C₂₆H₃₀N₂OS: C, 74.60; H, 7.22; N, 6.69; found: C, 74.58; H, 7.20; N, 6.67.

Example 33

Synthesis of (4-(methylthio)phenyl)(naphthalen-1-yl)methanone O-3-morpholinopropyl oxime (Compound 7b)

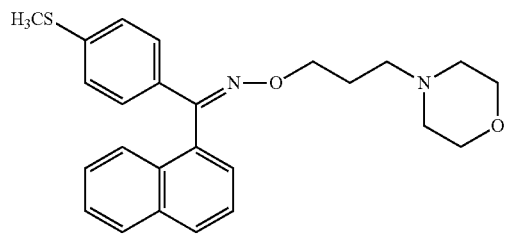

Into a 50 ml round bottom flask, 4-(methylthio)phenyl) (naphthalen-1-yl)methanone O-3-chloropropyl oxime (1 mmole, 369 mg), Morpholine (5 mmole, 0.44 ml) and dry methanol (10.0 ml) were taken. The reaction mixture was refluxed under anhydrous conditions for 6 hours. The reaction was followed by TLC monitoring. After completion of the reaction, methanol was evaporated under reduced pressure. The resulting mixture was poured onto water and extracted with ethyl acetate (3×50 ml), washed with water, dried over anhydrous Na₂SO₄ and concentrated. The crude product was purified by basic alumina column chromatography using distilled Hexane to yield the pure product (265 mg, 60%).

M.P.=89° C., ESI MS(m/z)=421(M+H); IR (KBr, Cm⁻¹): 3440.1, 2953.6, 2858.6, 2807.4, 2689.8, 1556.0, 1590.3, 1485.7, 1437.4, 1394.3, 1369.8, 1310.1, 1252.3, 1113.2, 1058.5, 585.8, 799.7, 777.7; (300MHz, CDCl₃): δ=7.93(d, J=7.9 Hz, 2H, ArH), 7.54-7.39(m, 6H, ArH), 7.30 (d, J=8.1 Hz, 1H, ArH), 7.15(d, J=8.0 Hz, 2H, ArH), 4.19(t, J=6.3 Hz, 2H, OCH₂), 3.70-3.60(m, 4H, OCH₂), 2.44(s, 3H, SCH₃), 2.30-2.15(m, 6H, NCH₂), 1.26(m, 2H, CH₂). Analysis calculated for C₂₅H₂₈N₂O₂S: C, 71.40; H, 6.71; N, 6.66. found: C, 71.38; H, 6.69; N, 6.64.

Example 34

Synthesis of (4-(methylthio)phenyl)(naphthalen-1-yl)methanone O-3-(4-methylpiperidin-1-yl)propyl oxime oxalate (Compound 7c)

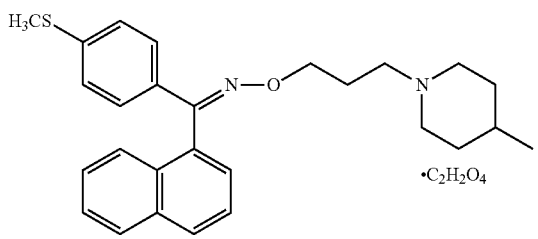

Into a 50 ml round bottom flask, 4-(methylthiophenyl) (naphthalen-1-yl)methanone O-3-chloropropyl oxime (1 mmole, 369 mg), 4-methylpiperidine (5 mmole, 0.59 ml) and dry methanol (10.0 ml) were taken. The reaction mixture was refluxed under anhydrous conditions for 6 hours. The reaction was followed by TLC monitoring. After completion of the reaction, methanol was evaporated under reduced pressure. The resulting mixture was poured onto water and extracted with ethyl acetate (3×50 ml), washed with water, dried over anhydrous Na$_2$SO$_4$ and concentrated. The crude product was purified by basic alumina column chromatography using distilled Hexane to yield the pure product (350 mg, 81.1%). The product obtained was oily so a salt of the compound was prepared.

Procedure for oxalate salt formation: Oxalic acid, 1 mmole/1 mmole of compound, (102.1 mg) and oily product (350 mg) were dissolved in dry methanol separately into two round bottom flasks. The acid and the compound were mixed and shaken thoroughly. The salt was precipitated using dry diethyl ether, filtered, washed with the same and collected. Yield: 400 mg, 71.7%.

M.P. (oxalate salt of compound): 145° C., ESI MS(m/z)=433 (M+H), IR Spectra: (KBr, Cm$^{-1}$): 3445.4, 2928.8, 1648.1, 1451.6, 1246.1, 779.6. $^1$H NMR (300MHz, CDCl$_3$): δ=7.93(d, J=8.0 Hz, 2H, ArH), 7.56-7.38(m, 6H, ArH), 7.30(d, J=8.1 Hz, 1H, ArH), 7.16(d, J=8.5 Hz, 2H, ArH), 4.13(m, 2H, OCH$_2$), 3.49-3.42(m, 2H, NCH$_2$), 2.63 (m, 2H, NCH$_2$), 2.45(s, 3H, SCH$_3$), 2.00(m, 2H, NCH$_2$), 1.63(m, 5H, CH$_2$ & CH), 1.24(m, 2H, CH$_2$), 0.96(d, J=5.6 Hz, 3H, CHCH$_3$). Analysis calculated for C$_{27}$H$_{32}$N$_2$OS (free base): C, 74.96; H, 7.46; N, 6.48; found: C, 74.92; H, 7.43; N, 6.47.

Example 35

Synthesis of (4-(methylthio)phenyl)(naphthalen-1-yl)methanone O-3-(butyl(methyl)amino)propyl oxime (Compound 7d)

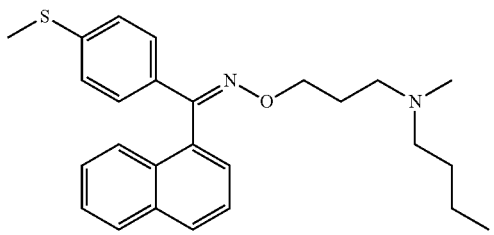 [SMILES: CCCCN(C)CCCO/N=C(/c1ccc(SC)cc1)c1cccc2ccccc12]

Into a 50 ml round bottom flask, (4-(methylthio)phenyl) (naphthalen-1-yl)methanone O-3-chloropropyl oxime (1 mmole, 369 mg), N-methylbutan-1-amine (5 mmole, 0.59 ml) and dry methanol (15.0 ml) were taken. The reaction mixture was refluxed under anhydrous conditions for 6 hours. The reaction was followed by TLC monitoring. After completion of the reaction, methanol was evaporated under reduced pressure. The resulting mixture was poured onto water and extracted with ethyl acetate (3×50 ml), washed with water, dried over anhydrous Na$_2$SO$_4$ and concentrated. The crude product was purified by basic alumina column chromatography using distilled Hexane to yield the pure product (287 mg, 68.3%).

Oily Compound; ESI MS (m/z)=421 (M+H); $^1$H NMR (300MHz, CDCl$_3$): δ=7.93(d, J=8 Hz, 2H, ArH), 7.62-7.39 (m, 6H, ArH), 7.31-7.26(m, 1H, ArH), 7.15-7.11(m, 2H, ArH), 4.19-4.10(m, 2H, OCH$_2$), 2.46(s, 3H, SCH$_3$), 2.44(t, J=6.7 Hz, 4H, NCH$_2$), 2.24(s, 3H, NCH$_2$), 1.34-1.22(m, 6H, CH$_2$), 0.91(t, J=6.9 Hz, 3H, CH$_3$). Analysis calculated for C$_{26}$H$_{32}$N$_2$OS: C, 74.24; H, 7.67; N, 6.66; found: C, 74.22; H, 7.65; N, 6.63.

Example 36

Synthesis of (4-methoxyphenyl)(naphthalen-1-yl) methanone O-3-(2-ethylhexylamino)propyl oxime (Compound 7e)

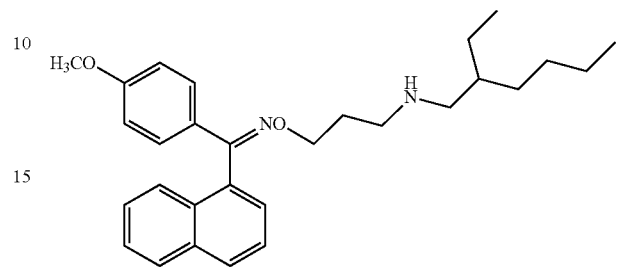

Into a 50 ml round bottom flask, (4-Methoxy-phenyl)-naphthalen-1-yl-methanone O-(3-chloro-propyl)-oxime (1 mmole, 353 mg), 2-ethylhexan-1-amine (5 mmole, 0.82 ml) and dry methanol (10.0 ml) were taken. The reaction mixture was refluxed under anhydrous conditions for 6 hours. The reaction was followed by TLC monitoring. After completion of the reaction, methanol was evaporated under reduced pressure. The resulting mixture was poured onto water and extracted with ethyl acetate (3×50 ml), washed with water, dried over anhydrous Na$_2$SO$_4$ and concentrated. The crude product was purified by basic alumina column chromatography using distilled Hexane to yield the pure product (321 mg, 71.9%).

Oily Compound; ESI MS (m/z)=447 (M+H); $^1$H NMR (300MHz, CDCl$_3$): δ=8.07(d, J=9 Hz, 1H, ArH), 7.94-7.91 (m, 1H, ArH), 7.67-7.61(m, 2H, ArH), 7.59-7.54(m, 3H, ArH), 7.48-7.45 (m, 1H, ArH), 7.41-7.39 (d, 1H, ArH), 7.25-7.22(d, 2H, ArH), 3.48-3.28(m, 1H, OCH$_2$), 3.25-3.23 (m, 1H, OCH$_2$), 2.47 (s, 3H, SCH$_3$), 1.93-1.87 (m, 2H, NCH$_2$), 1.50-1.48(m, 2H, NCH$_2$), 1.12-0.92(m, 5H, CH$_2$—CH$_2$, CH), 0.81-0.60(m, 12H, 3CH$_2$, 2CH$_3$); Analysis calculated for C$_{29}$H$_{38}$N$_2$O$_2$: C, 77.99; H, 8.58; N, 6.27; found: C, 78.03; H, 8.61; N, 6.30.

Example 37

Synthesis of (4-(methylthio)phenyl)(naphthalen-1-yl)methanone O-4-(piperidin-1-yl)butyl oxime (Compound 8a)

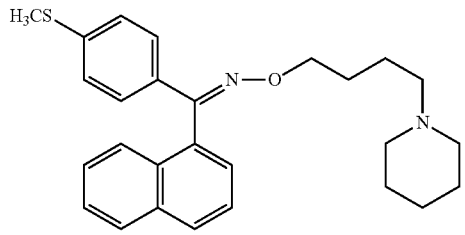

Into a 50 ml round bottom flask, 4-(methylthiophenyl) (naphthalen-1-yl)methanone O-4-chlorobutyl oxime (1 mmole, 383 mg), piperidine (5 mmole, 0.49 ml) and dry methanol (10.0 ml) were taken. The reaction mixture was refluxed under anhydrous conditions for 7 hours. The reaction was followed by TLC monitoring. After completion of the reaction, methanol was evaporated under reduced pressure. The resulting mixture was poured onto water and extracted with ethyl acetate (3×50 ml), washed with water, dried over anhydrous Na$_2$SO$_4$ and concentrated. The crude product was purified by basic alumina column chromatography using distilled Hexane to yield the pure product. Yield: 361 mg, 83.6%.

Oily Compound, ESI MS (m/z)=433 (M+H); IR Spectra: (Neat, Cm$^{-1}$): 3020.7, 2934.8, 1595.0, 1216.0, 761.4; $^1$H NMR (CDCl$_3$, 300MHz): δ=7.93 (d, J=8.04 Hz, 2H, ArH), 7.67 (d, J=8.6 Hz, 1H, ArH), 7.58-7.41(m, 5H, ArH), 7.39-7.28(m, 1H, ArH), 7.17(d, J=8.6 Hz, 2H, ArH), 4.17-4.13(t, J=6.8 Hz, 2H, OCH$_2$), 2.46(s, 3H, SCH$_3$), 2.24-2.16(m, 6H, NCH$_2$), 1.64-1.28(m, 10H, CH$_2$); Analysis calculated for C$_{27}$H$_{32}$N$_2$OS (free base)=C, 74.96; H, 7.46; N, 6.48; found: C, 74.92; H, 7.51; N, 6.50.

Example 38

Synthesis of (4-(methylthio)phenyl)(naphthalen-1-yl)methanone O-4-(pyrrolidin-1-yl)butyl oxime (Compound 8b)

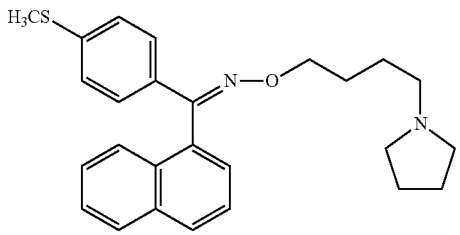

Into a 50 ml round bottom flask, 4-(methylthio)phenyl)(naphthalen-1-yl)methanone O-3-chloropropyl oxime (1 mmole, 369 mg), Pyrrolidine (5 mmole, 0.42 ml) and dry methanol (10.0 ml) were taken. The reaction mixture was refluxed under anhydrous conditions for 7 hours. The reaction was followed by TLC monitoring. After completion of the reaction, methanol was evaporated under reduced pressure. The resulting mixture was poured onto water and extracted with ethyl acetate (3×50 ml), washed with water, dried over anhydrous Na$_2$SO$_4$ and concentrated. The crude product was purified by basic alumina column chromatography using distilled Hexane to yield the pure product (289 mg, 69.1%).

Oily Compound; ESI MS(m/z)=419(M+H); IR (Neat, Cm$^{-1}$): 3379.8, 3020.8, 1635.5, 1514.8, 1216.4, 761.7; NMR (300MHz, CDCl$_3$): δ=7.93(d, J=8.1 Hz, 2H, ArH), 7.56-7.42(m, 6H, ArH), 7.33-7.28(m, 1H, ArH), 7.16(d, J=8.6 Hz, 2H, ArH), 4.18(t, J=6.5 Hz, 2H, OCH$_2$), 2.46(s, 3H, SCH$_3$), 2.37-2.31(m, 4H, NCH$_2$), 1.77-1.43(m, 8H, CH$_2$). Analysis calculated for C$_{26}$H$_{30}$N$_2$OS: C, 74.60; H, 7.22; N, 6.69; found: C, 74.55; H, 7.18; N, 6.67.

Example 39

Synthesis of (4-(methylthio)phenyl)(naphthalen-1-yl)methanone O-4-(phenethylamino)butyl oxime (Compound 8c)

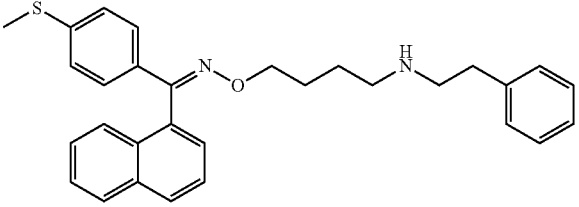 [SMILES: CSc1ccc(/C(=N/OCCCCNCCc2ccccc2)c2cccc3ccccc23)cc1]

Into a 50 ml round bottom flask, 4-(methylthio)phenyl)(naphthalen-1-yl)methanone O-4-chlorobutyl oxime (1 mmole, 383 mg), 2-phenylethanamine (5 mmole, 0.63 ml) and dry methanol (15.0 ml) were taken. The reaction mixture was refluxed under anhydrous conditions for 6 hours. The reaction was followed by TLC monitoring. After completion of the reaction, methanol was evaporated under reduced pressure. The resulting mixture was poured onto water and extracted with ethyl acetate (3×50 ml), washed with water, dried over anhydrous Na$_2$SO$_4$ and concentrated. The crude product was purified by basic alumina column chromatography using distilled Hexane to yield the pure product (329 mg, 72.5%).

Oily Compound; ESI MS (m/z)=455 (M+H); $^1$H NMR (300MHz, CDCl$_3$): δ=7.90-7.85(m, 2H, ArH), 7.63(d, J=9 Hz, 1H, ArH), 7.54-7.49(m, 2H, ArH), 7.45-7.36(m, 5H, ArH), 7.29(m, 1H, ArH), 7.23-7.14(m, 5H, ArH), 4.13(t, J=6 Hz, 2H, OCH$_2$), 2.50-2.45(m, 2H, NCH$_2$), 2.45(s, 3H, SCH$_3$), 1.60-1.55(m, 4H, NCH$_2$, ArCH$_2$), 0.91-0.85(m, 4H, CH$_2$—CH$_2$). Analysis calculated for C$_{29}$H$_{30}$N$_2$OS: C, 76.61; H, 6.65; N, 6.16; found: C, 76.56; H, 6.64; N, 6.15.

Example 40

Synthesis of (4-(methylthio)phenyl)(naphthalen-1-yl) methanone O-4-(benzyl(ethyl)amino)butyl oxime (Compound 8d)

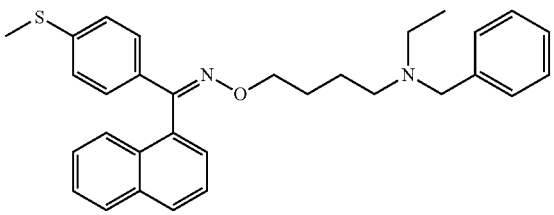 [SMILES: CCN(CCCCO/N=C(/c1ccc(SC)cc1)c1cccc2ccccc12)Cc1ccccc1]

Into a 50 ml round bottom flask, 4-(methylthio)phenyl)(naphthalen-1-yl)methanone O-4-chlorobutyl oxime (1 mmole, 383 mg), N-benzylethanamine (5 mmole) and dry methanol (15.0 ml) were taken. The reaction mixture was refluxed under anhydrous conditions for 7 hours. The reaction was followed by TLC monitoring. After completion of the reaction, methanol was evaporated under reduced pressure. The resulting mixture was poured onto water and extracted with ethyl acetate (3×50 ml), washed with water, dried over anhydrous $Na_2SO_4$ and concentrated. The crude product was purified by basic alumina column chromatography using distilled Hexane to yield the pure product (329 mg, 72.5%). Oily Compound; ESI MS (m/z)=483 (M+H); $^1$H NMR (300MHz, $CDCl_3$): δ=7.93-7.91(m, 3H, ArH), 7.64-7.14(m, 13H, ArH), 4.17(t, J=6 Hz, 2H, $OCH_2$), 3.82(s, 2H, $NCH_2$), 2.75(q, J=4.0 Hz, 2H, $NCH_2$), 2.54-2.47(m, 5H, $SCH_3$, $NCH_2$), 1.77-1.66(m, 4H, $CH_2$), 1.19-1.14(t, J=4.0 Hz, 3H, $CH_3$). Analysis calculated for $C_{31}H_{34}N_2OS$: C, 77.14; H, 7.10; N, 5.80; found: C, 77.17; H, 7.12; N, 5.85.

Primary Evaluation of Aryl Naphthyl Methanone Oxime Derivative Compounds in Leukemia Cell Lines K562 and HL-60

All the compounds synthesized were screened for cytotoxicity on leukemia cell lines K562, HL-60 and mouse fibroblast cell line NIH3T3 using (3-(4,5-dimethylthiazol-2-yl)-2,5-diphenyltetrazolium bromide (MTT) assay kit from Sigma according to manufacturer's instructions and trypan blue exclusion method. Activity of these compounds is given in Table-1. Cytotoxicity of five most active compounds (5a, 5d, 5j, 5m and 7c) was further checked in Kasumil and U937 cells. Compounds 5a, 5d, 5m and 7c exhibited higher efficacy than imatinib ($IC_{50}$ values are shown in Table 2) in K562.

TABLE 1

$IC_{50}$ (μM) values of compounds in K562, HL60 and NIH3T3 cell lines as tested using MTT assay after 48 h treatment. Results were calculated from three independent experiments performed in triplicate. Compounds with $IC_{50}$ more than 15 μM were considered inactive.

| S. No. | Compound | K562 | HL60 | NIH3T3 |
|---|---|---|---|---|
| 1 | 4a | >50 μM | >50 μM | >50 μM |
| 2 | 4b | >50 μM | >50 μM | >50 μM |
| 3 | 5a | 5.8 μM | >20 μM | 15 μM |
| 4 | 5b | 25 μM | 19 μM | 20 μM |
| 5 | 5c | >50 μM | >50 μM | >50 μM |
| 6 | 5d | 3.61 μM | 5.99 μM | >20 μM |
| 7 | 5e | 7 μM | 14 μM | 16 μM |
| 8 | 5f | >25 μM | >50 μM | 26 μM |
| 9 | 5g | >50 μM | >50 μM | >50 μM |
| 10 | 5h | >50 μM | >50 μM | >50 μM |
| 11 | 5i | >30 μM | >50 μM | 40 μM |
| 12 | 5j | 8.5 μM | 10 μM | 25 μM |
| 13 | 5k | >50 μM | >50 μM | >50 μM |
| 14 | 5l | >50 μM | >50 μM | >50 μM |
| 15 | 5m | 4.8 μM | 7.78 μM | >25 μM |
| 16 | 5p | >50 μM | 15 μM | >50 μM |
| 17 | 5q | >50 μM | >50 μM | >50 μM |
| 18 | 6a | >50 μM | >50 μM | >50 μM |
| 19 | 6b | >50 μM | >50 μM | >50 μM |
| 20 | 6c | >50 μM | >50 μM | >50 μM |
| 21 | 6d | >50 μM | >50 μM | >50 μM |
| 22 | 6e | >50 μM | >50 μM | >50 μM |
| 23 | 6f | >50 μM | >50 μM | >50 μM |
| 24 | 6g | 6.66 μM | >50 μM | 16 μM |
| 25 | 6h | 19 μM | >50 μM | 26 μM |
| 26 | 6i | >50 μM | >50 μM | >50 μM |
| 27 | 7a | >20 | >50 μM | >50 μM |
| 28 | 7b | >50 μM | >50 μM | >50 μM |
| 29 | 7c | 5.73 μM | >50 μM | 21 μM |
| 30 | 7d | >50 μM | 13 μM | >50 μM |
| 31 | 8a | 6.34 μM | 16 μM | 20 μM |
| 32 | 8b | >50 μM | >50 μM | >50 μM |
| 33 | 8c | >30 μM | >50 μM | >50 μM |
| 34 | 8d | 16.3 μM | >50 μM | >50 μM |

Evaluation of Hit Compounds in Multiple Leukemia Cell-Lines:

To consider a molecule as a candidate compound in cancer drug therapy, the test compound must have specific cytotoxicity towards the cancer cells without affecting normal cell growth. Therefore, all active compounds were assessed for toxicity in non-cancer cell-lines: mouse fibroblast cell line (NIH3T3) and monkey kidney epithelial cells (Vero). 5d and 5m exhibited much higher $IC_{50}$ values in the normal cells compared to leukemia cells. Therefore, based on safety index ($IC_{50}/CC_{50}$), 5d [Centans; based on IUPAC name prefixed with Central Drug Research Institute's signature (Cent)] was selected as a lead compound.

TABLE 2

$IC_{50}$ of Active compounds in Leukemia and normal cell lines. Results were calculated from three independent experiments performed in triplicates.

| Compound | K562 | HL60 | Kasumi 1 | U937 | Vero | NIH3T3 |
|---|---|---|---|---|---|---|
| 5a | 5.8 μM | >20 μM | 27 μM | >18 μM | >25 μM | 15 μM |
| 5d (Centans) | 3.61 μM | 5.99 μM | 6.78 μM | 8.12 μM | >25 μM | >20 μM |
| 5j | 8.5 μM | 10 μM | 20 μM | >24 μM | >25 μM | 25 μM |
| 5m | 4.8 μM | 7.78 μM | >10 μM | >15 μM | >25 μM | >25 μM |
| 7c | 5.73 μM | >50 μM | 19 μM | >25 μM | >25 μM | 21 μM |
| IMT | 7.53 μM | 9.63 μM | ND | ND | ND | ND |

As described in table 2, among all the compounds tested compound 5d (Centans) showed strong cytotoxicity against BCR-ABL-positive CML model K562, acute myeloblastic leukemia model HL60, Kasumil (Acute Myeloid Leukemia with t(8; 21) translocation) and U937 (monoblast), while it showed no toxicity against non-cancerous fibroblastic cell-lines Vero and NIH3T3. ND; not done.

Evaluation of the Efficacy of Lead Compound Centans in Comparison with Imatinib and Dasatinib:

The efficacy of Centans in comparison to marketed drugs imatinib and dasatinib were determined in K562 and HL-60 cells that were used as examples of CML and AML respectively. As shown in table 3, Centans exhibited a much lower IC50 in comparison to both imatinib and dasatinib, indicating its higher efficacy.

TABLE 3

$IC_{50}$ of Centans, imatinib and dasatinib in K562 and HL60 cell lines after 48 h of treatment. Following 48 h treatment of indicated cell lines with Centans, imatinib or dasatinib (10 point dose response) MTT assays were performed and IC-50 for the compounds were determined. Results were calculated from three independent experiments performed in triplicates.

|  | Cell-line | IC 50(μM) |
|---|---|---|
| Centans | HL 60 | 5.99 |
|  | K562 | 3.61 |

TABLE 3-continued $IC_{50}$ of Centans, imatinib and dasatinib in K562 and HL60 cell lines after 48 h of treatment. Following 48 h treatment of indicated cell lines with Centans, imatinib or dasatinib (10 point dose response) MTT assays were performed and IC-50 for the compounds were determined. Results were calculated from three independent experiments performed in triplicates.

|  | Cell-line | IC 50(μM) |
|---|---|---|
| Imatinib | HL 60 | 9.63 |
|  | K562 | 5.16 |
| Dasatinib | HL 60 | 6.85 |
|  | K562 | 6.8 |

Centans shows higher efficacy than imatinib and dasatinib in peripheral blood mononuclear cells (PBMC) isolated from CML patients.

Next PBMCs isolated from freshly diagnosed, imatinib sensitive, imatinib resistant CML (BCR-ABL+ve) patient samples or healthy controls were treated for 48h with Centans, imatinib and dasatinib and following treatment the efficacy of each drug in each group was determined by MTT assay. As shown in Table 4. Centans showed most robust cytotoxic effect in PBMCs from imatinib-resistant CML patients (72%) compared to imatinib (40%) and dasatinib (59%). Centans also showed higher cytotoxicity than imatinib or dasatinib in PBMCs from freshly diagnosed or imatinib sensitive patients, while all three drugs showed comparative activity on PBMCs from healthy controls.

TABLE 4

PBMCs isolated from indicated groups of BCR-ABL-positive CML patients or healthy individuals were treated with 1 μM Centans, imatinib or dasatinib for 48 h and the cytotoxicity was determined by MTT assay in triplicates. Data represents % cell death. Centans showed better efficacy than both imatinib and dasatinib in all the groups, but this efficacy was highest in imatinib-resistant patient samples ($p < 0.01$).

| Patient Type | Sample ID | Centans | P value Centans vs Imatinib | Imatinib | P value Centans vs Dasatinib | Dasatinib |
|---|---|---|---|---|---|---|
| Healthy control | C1 | 14.01 | 0.76978 | 10.51 | 0.30456 | 2.39 |
|  | C2 | 20.65 |  | 17.91 |  | 12.03 |
|  | C3 | 16.93 |  | 19.93 |  | 18.93 |
|  | Average | 17.19667 |  | 16.11667 |  | 11.11667 |
|  | SEM | 1.921435 |  | 2.863339 |  | 4.796476 |
| Freshly Diagnosed | P1 | 68.82 | 0.102813 | 61.58 | 0.017607 | 55.46 |
|  | P10 | 73.32 |  | 53.34 |  | 43.59 |
|  | P11 | 55.61 |  | 49.51 |  | 32.75 |
|  | P15 | 71.19 |  | 64.1 |  | 52.79 |
|  | Average | 67.235 |  | 57.1325 |  | 46.1475 |
|  | SEM | 3.982484 |  | 3.42554 |  | 5.138736 |
| Imatinib Resistant | P2 | 69.46 | 0.007977 | 32.81 | 0.0074 | 56.61 |
|  | P13 | 70.03 |  | 34.05 |  | 53.82 |
|  | P14 | 77.68 |  | 48.35 |  | 68.84 |
|  | P17 | 78.93 |  | 47.84 |  | 56.41 |
|  | P18 | 64.49 |  | 36.67 |  | 57.84 |
|  | Average | 72.118 |  | 39.944 |  | 58.704 |
|  | SEM | 3.030576 |  | 3.786158 |  | 2.926022 |
| Imatinib treated/ Responder | P3 | 50.92 | 0.32157 | 49.79 | 0.510364 | 73.22 |
|  | P12 | 62.41 |  | 48.39 |  | 43.65 |
|  | P16 | 76.59 |  | 62.39 |  | 47.26 |
|  | Average | 63.30667 |  | 53.52333 |  | 54.71 |
|  | SEM | 6.429235 |  | 3.855299 |  | 8.065716 |

Next, comparative cytotoxic efficacy of centans with imatinib and dasatinib was assessed in CML patient samples harbouring different BCR-ABL mutations by MTT assay. PBMCs isolated from patients harbouring indicated mutations in BCR-ABL were treated with 5 µM centans, imatinib or dasatinib for 48h, followed by MTT assay. As shown in Table 5. Centans showed much stronger cytotoxic activity in comparison to imatinib or dasatinib. Importantly centans showed appreciable cytotoxicity in patient sample harbouring multidrug resistant T315I BCR-ABL mutation.

TABLE 5

Centans induces cell death in PBMCs from patients with BCR-ABL mutations including multi-drug resistant T315I mutation with higher efficacy than imatinib and dasatinib.

| | % Cell Death | | |
| --- | --- | --- | --- |
| Mutation | centans | Imatinib | Dasatinib |
| T315I | 34.60 | 4.81 | 8.91 |
| H396R | 40.78 | 8.66 | 27.82 |
| Y253H | 42.93 | 19.36 | 32.96 |
| E255V | 48.18 | 23.10 | 44.40 |

Centans-Induced Cell-Death in K562 and HL-60 is Apoptotic in Nature.

To determine whether cell death caused by Centans is specifically associated with apoptosis: phosphatidylserine exposure (Annexine V/PI; Flow cytometry) was performed in K562 and HL-60 cell-lines. As apparent form FIG. 1, treatment with Centans caused a robust and dose-dependent increase in phosphatidylserine exposure, which reached 5 fold over vehicle with 5 µM ANS in K562 and about 3 fold in HL-60.

FIG. 1 Centans induces Apoptosis in K562 and HL-60 cells. (A and B) Centans increases phosphatidylserine exposure—K562 (A) and HL-60 (B) cells were treated with vehicle (DMSO) or Centans (dissolved in DMSO) at indicated concentrations for 24 h and phosphatidylserine exposure was assessed by flow cytometry using the FL1-H channel (Annexin-V) and FL2-H channel (PI). Representative dot plots and relative apoptotic cell in the graph are shown. C and D is the graphical representation of data pooled from three independent experiments. *P<0.05, P<0.01 *P<0.001 compared to vehicle treated control.

Centans Induces G0/G1 Growth Arrest in K562 and HL-60 Cells.

Figure 2:
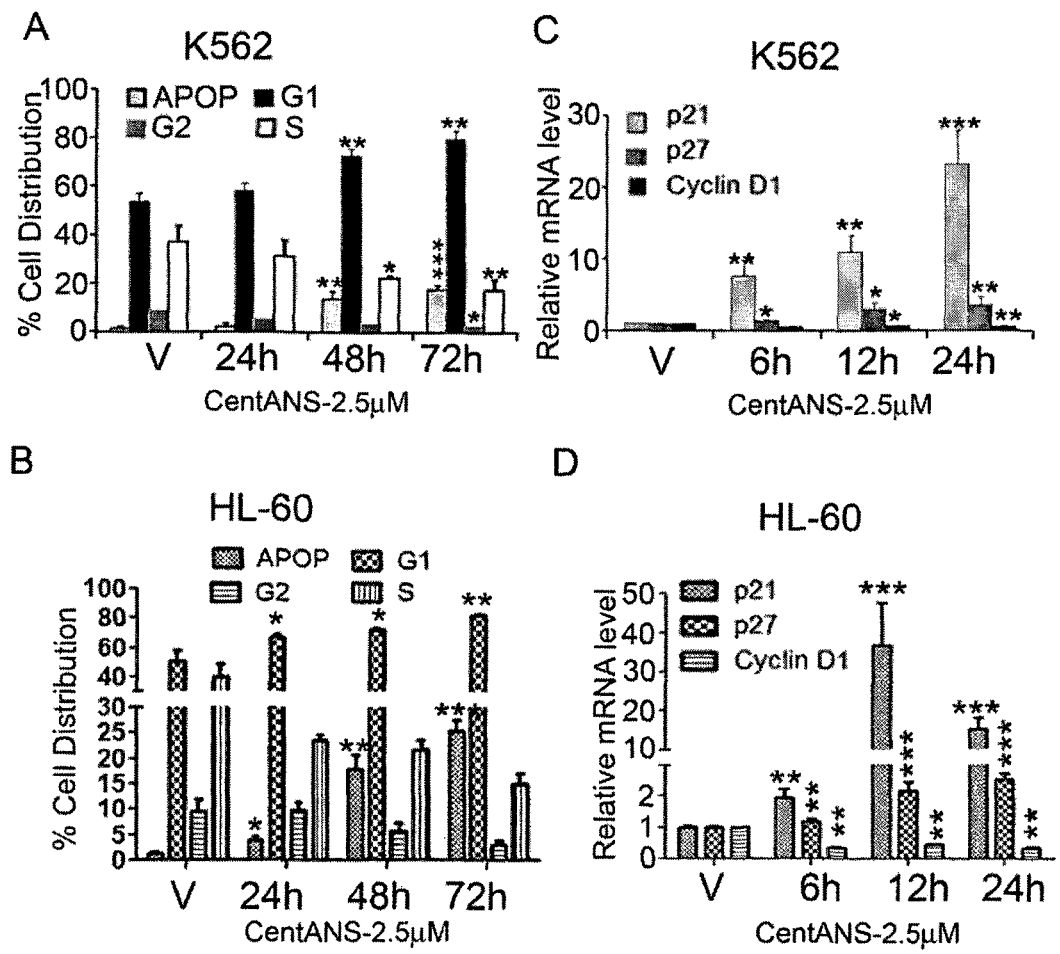
FIG. 2: CentANS induces G0/G1 growth arrest in K562 and HL-60 cells.

To evaluate the cytostatic effect of Centans, K562 and HL-60 cells were analysed for cell cycle progression in presence of Centans in and as shown in FIGS. 2 A and B, that the G1 and apoptotic sub-populations were significantly increased by Centans treatment. To further confirm this, mRNA levels of cell cycle regulatory proteins p21, p27 and cyclin D1 were measured by real time PCR and we found that Centans significantly enhanced mRNA levels of growth suppressant proteins p21 and p27 while it decreased the level of pro-proliferative Cyclin D1 mRNA in both K562 and HL-60 cells. (FIGS. 2 C and D).

FIG. 2 Centans induces G1 Growth arrest. (A and B) Cell cycle analysis—

Propidium iodide (PI) staining of K562 cells (A) and HL-60 cells (B) treated with vehicle (DMSO) or 0.5 µM Centans, followed by flow cytometry analysis to find % distribution of cells in different phases of the cell cycle. Data has been shown as percent of total cells from data pooled from three independent experiments. (C and D). mRNA expression of cell cycle regulatory factors—K562 (C) or HL-60 (D) cells were treated with Vehicle or Centans, followed by mRNA isolation and cDNA preparation and quantitative real-time PCR (p21, p27 and cyclin D1). Graphs represented pooled data from three independent experiments. *P<0.05, P<0.01,*P<0.001 compared to vehicle treated control.

Figure 3:
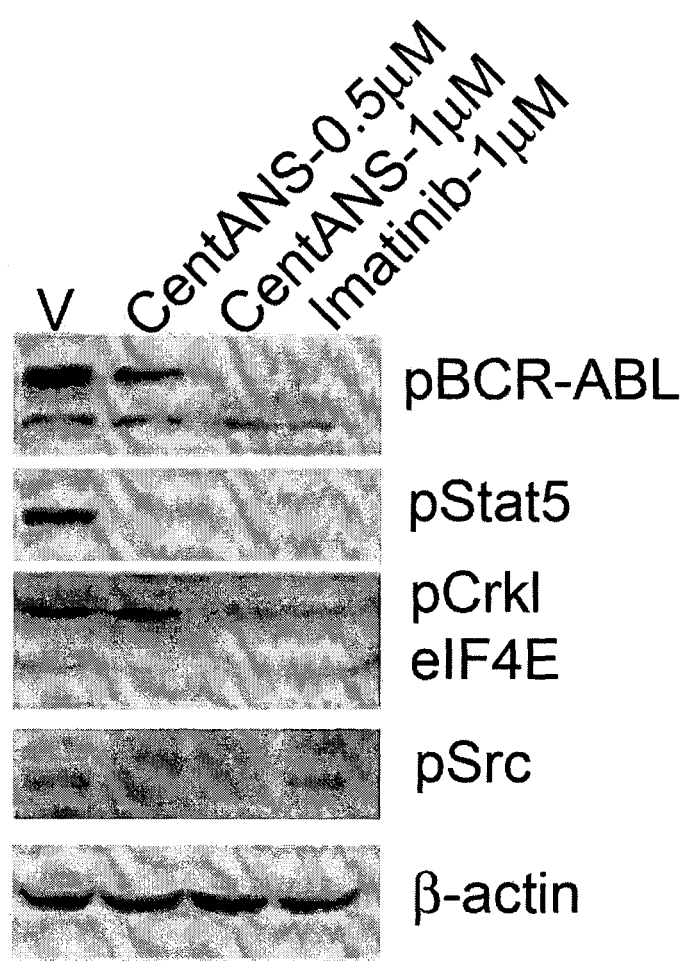
FIG. 3: Centans induces dephosphorylation of BCR-ABL and SRC protooncogene.

Centans Induces Dephosphorylation of BCR-ABL and SRC:

Kinase activity of Bcr-Abl is the major cause of CML, and since Centans causes growth arrest and apoptosis in Bcr-Abl positive K562 cells, phosphorylation status of Bcr-Abl which is representative of its kinase activity was measured by immunoblotting. As shown in FIG. 3 both imatinib and Centans dose dependently inhibited phosphorylation of BCR-ABL (pBCR-ABL) and its downstream substrates stat5 and Crkl, while eIF4E (used as a control gene unaffected by BCR-ABL signalling) remained unchanged.

Effect of Centans was also observed in terms of SRC kinase activation. SRC kinases activated by BCR-ABL remain fully active in imatinib-treated mouse leukemic cells, suggesting that imatinib does not inactivate all BCR-ABL activated signalling pathways. This SRC pathway is responsible for survival of leukemic cells that becomes imatinib resistant and for CML transition to lymphoid blast crisis. Effect of Centans and Imatinib was compared on its dephosphorylation by immunoblotting and we found that Centans dephosphorylating SRC-1 in a dose dependent manner, while imatinib failed to do so (FIG. 3).

FIG. 3. Centans inhibits BCR-ABL signalling and SRC phosphorylation. K562 Cells were treated with V (DMSO), 0.5 µM, 1 µM Centans or 1 µM Imatinib for 48h and protein lysate prepared from these cells were used to detect the phosphorylation status of BCR-ABL, STAT-5, CRKL and vSRC-1 by western blotting. ELF4E and β-actin were used as loading control.

Figure 4:
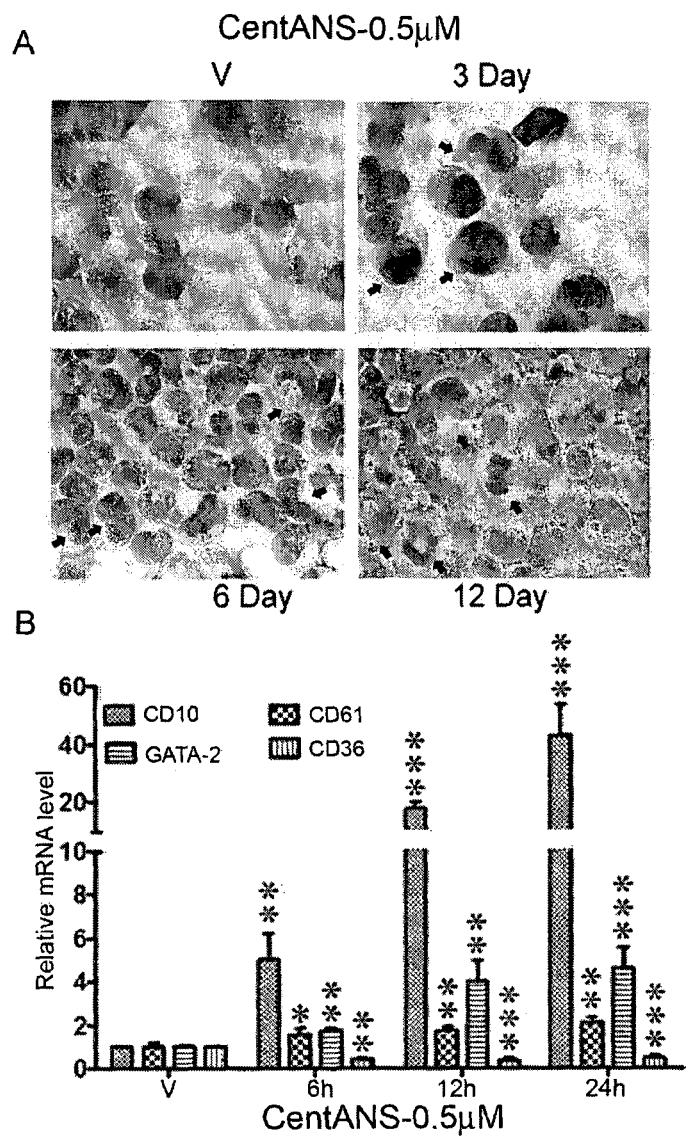
FIG. 4: Centans induces megakaryocytic differentiation in K562 Cells

Centans Causes Differentiation in K562 Cells:

In order to clarify whether the inhibitory effects of Centans on the growth and cell cycle of K562 cells was followed by differentiation, Centans treated cells was stained with Wright-Giemsa stain. FIG. 4.A. clearly indicates that Centans is capable of inducing differentiation in K562 cells in a dose-dependent manner. After 3 day of incubation with 0.5 µM of Centans, cells exhibited megakaryocytic morphology characterized by a sharp increase in nuclear-to-cytoplasm ratio, and multiple lobed nuclei, while the vehicle-treated cells displayed homogenous population of immature blast-like cell morphology (FIG. 4.A). This differentiation was much more pronounced at 12d, where mature megakaryocytes were visible (FIG. 4A). Confirmation of Centans-mediated megakaryocytic differentiation was attained through measurement of expression of relevant cell differentiation markers by quantitative real time PCR. mRNA expression levels of cluster of differentiation 10 (CD10) (transiently present during B-cell maturation at early-B and pre-B lymphoblastic stages and related to megakaryocytic differentiation), CD36 (erythroid differentiation lineage), GATA2 (Over expression of GATA-2 inhibits erythroid and promotes megakaryocyte differentiation) and CD61 (megakaryocytic differentiation marker) was measured. We found that the expression level of CD10, GATA2 and CD61 were increased while that of CD36 was decreased. These results further confirm that the differentiation induced by Centans is megakaryocytic (FIG. 4.B).

FIG. 4. CentANS induces Differentiation in K562 cells. (A) Giemsa Staining—K562 cells treated with CentANS (0.5 µM) for 3, 6 and 12 days and were cytospinned on Microscopy slides and stained with Giemsa and May Grunwald solutions, slides were micro-photographed and used to detect change in nuclear morphology. (B) Expression of differentiation Markers—K562 cells were treated with vehicle; V (DMSO) or centANS and mRNA from these cells were isolated and reverse transcribed. cDNA was used to measure the expression CD10, GATA2, CD61, (megakaryocytic lineage markers) and CD36 (Erythroid lineage marker) by Quantitative Real time PCR, GAPDH was used as control. Data represents mean±SEM from three independent experiments; *P<0.05, P<0.01, and *P<0.001 compared to control.

Centans Induces Granulocytic/Monocytic Differentiation in HL-60:

Differentiation potential of Centans on HL-60 cells was evaluated by the effect of this compound on Nuclear/cytosolic ratio and change in nuclear morphology, which are reliable markers of differentiation. For this, HL60 cell treated with Centans were cyto-spinned on microscope slides and stained with Wright-Giemsa and micro-photographed. As shown in FIG. 5A (upper panel), morphological features of differentiation, such as condensation of nuclei and protrusion of cytoplasm, were clearly evident among the treated cells. This was further confirmed by nitro blue tetrazolium (NBT) reduction assay in HL-60 cells (NBT reduction is a hallmark of monocyte activity). FIG. 5A (lower panel) depicts time-dependent reduction of NBT by Centans-treated cells.

Further confirm of granulocytic/monocytic differentiation of HL-60 cells by Centans, was obtained by QRT-PCR analysis of expression of lineage specific differentiation markers following Centans treatment. mRNA level of CD11b, a marker for granulocytic differentiation was significantly increased (FIG. 5B). Further, mRNA level of GCSFR, a key marker for terminal granulocytic differentiation increased upon Centans treatment (FIG. 5B). Centans also enhanced expression of c/EBP group of transcription factors that have been shown to be especially critical in granulocyte development (FIG. 5B).

Figure 5:
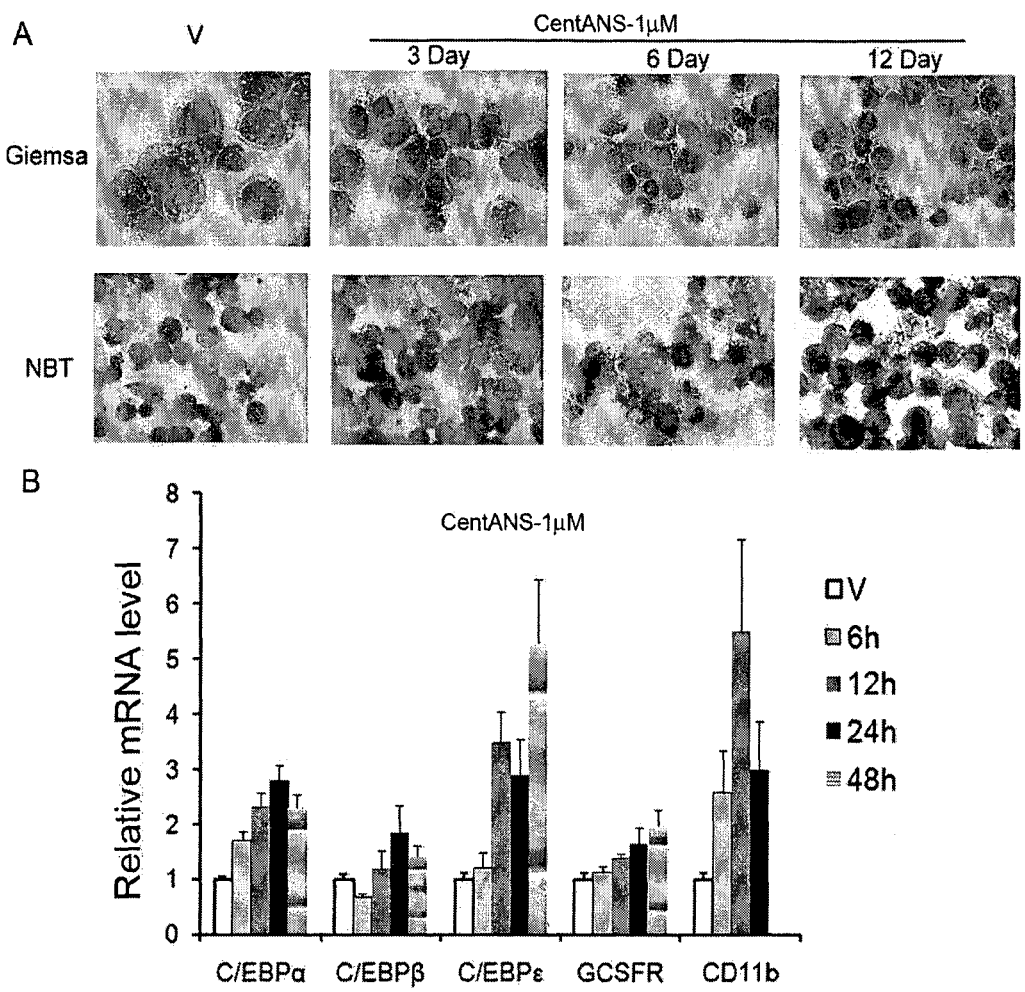
FIG. 5: Centans induces Granulocytic/monocytic differentiation in HL-60 cells.

FIG. 5. Centans induces granulocytic/monocytic differentiation in HL-60 model of AML. A. HL60 cells treated with Centans (1 μM) for 3, 6 and 12 days were cytospinned on Microscope slides and stained with Giemsa and May Grünwald solutions (upper panel) or NBT (lower panel), slides were microphotographed and used to detect change in nuclear morphology and NBT reduction. B. HL60 cells were treated with Vehicle (DMSO) or Centans as indicated in image, mRNA from these samples were isolated and reverse transcribed and these samples were used to measure the expression of CD11b GCSFR, and C/EBPα/β& ε by Quantitative real-time PCR, using GAPDH as normalizing control. Data presented as mean f SEM from three independent experiments; *P<0.05, P<0.01, and *P<0.001 compared to vehicle treated control.

Evaluation of Centans in Solid Tumor:

Efficacy of Centans and related series of compounds were evaluated in solid tumor cell-lines MCF-7 (estrogen receptor positive, non-metastatic breast tumor), MDA-MB-231 (estrogen receptor negative, metastatic breast tumor), DU-145 (prostrate tumor), Ishikawa (endometrial adenocarcinoma) cells by MTT assay following 24h treatment of indicated compounds. As depicted in table 6. Centans showed selective cytotoxicity in all the cancer cells tested but not in non-cancer cell-lines Vero and HEK-293. Efficacy of Centans was comparable to that of the positive control compound 4-hydroxy-tamoxifen (4-OHT).

TABLE 6

IC$_{50}$ of Centans and related compounds in cell line models of breast, prostate and endometrial cancers after 48 h of treatment. Following 48 h treatment of indicated cell lines with Centans, Centans analogs or 4-OHT (10 point dose response) MTT assays were performed and IC-50 for the compounds were determined. Results were calculated from three independent experiments performed in triplicates.

| Compound | MCF-7 | MDA-MB231 | DU-145 | Ishikawa |
|---|---|---|---|---|
| 4a | 18 | 20 | >50 | >50 |
| 5a | 13.5 | 8.8 | 10 | 10 |
| 5b | 6.6 | 5.01 | 9.5 | 6 |
| 5c | 14 | 12.78 | 15 | 9 |
| 5d (Centans) | 7.5 | 7.2 | 9 | 12 |
| 5f | >50 | >50 | >50 | >50 |
| 5m | 8 | 7.2 | 9.5 | 7 |
| 6a | 18 | >50 | >50 | >50 |
| 6b | 25 | >50 | >50 | >50 |
| 6c | 15 | >50 | >50 | >50 |
| 6d | 20 | >50 | >50 | >50 |
| 6e | 23 | >50 | >50 | >50 |
| 6i | 20.5 | >50 | >50 | >50 |
| 7a | 5 | 20 | 15 | 12 |
| 7b | >50 | >50 | >50 | >50 |
| 7c | 6.5 | 20 | 10 | >50 |
| 8a | 8 | 18 | 7.5 | 18 |
| 8b | >50 | >50 | >50 | >50 |
| OH-TAM | 8.8 | 8 | 10 | 20 |

Efficacy of centans in colon cancer cell-lines were also assessed using sulphorhodamine B assay and as shown in table 7, centans exhibited robust cytotoxicity in four different colon cancer cell lines compared to the marketted drug for colon cancer 5-fluoro uracil (5-FU).

TABLE 7

IC50 of Centans in colon cancer cell lines as determined by Sulphorhodamine B (SRB) assay.

| Cancer cell-line | SW620 | DLD1 | HCT116 | Colo205 |
|---|---|---|---|---|
| Centans | 8.78 μM | 15.6 μM | 7.7 μM | 4.2 μM |
| 5-FU | >50 μM | 16.38 μM | >50 μM | 38.06 μM |

Centans Induces Apoptosis in MCF-7 and MDA-MB-231 Cell-Lines.

To assess if the cell death induced by centans in MCF-7 and MDA-MB231 lines is apoptotic in nature, apoptosis was measured by flow cytometry using annexin V/PI staining kit from Sigma according to manufacturer's instructions. A concentration-dependent increase in apoptotic cell population was observed upon treatment with Centans and the effect was stronger in MDA-MB231 than MCF-7 cells (FIGS. 6A and B).

Figure 6:
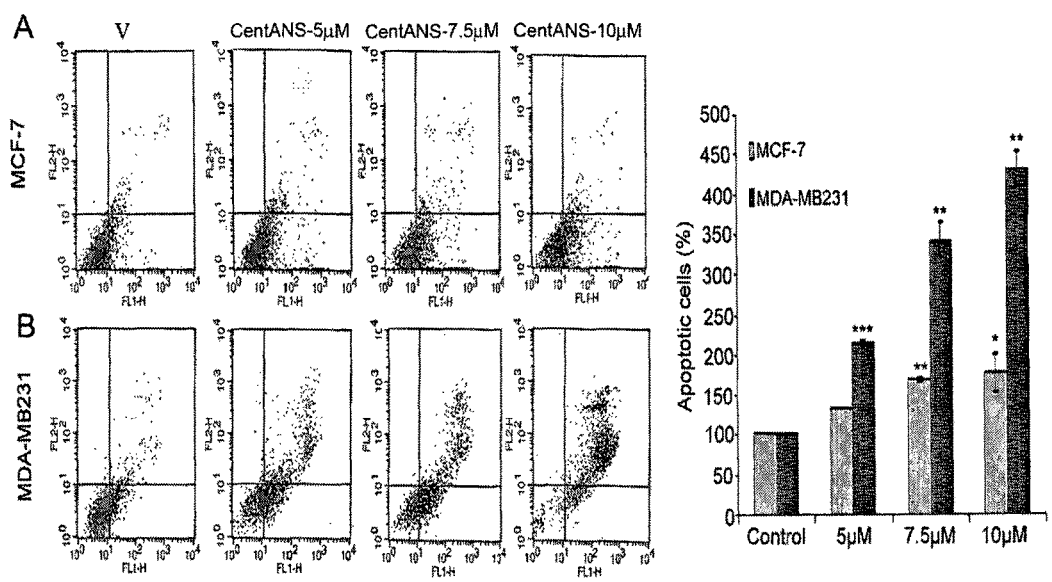
FIG. 6: Centans induces apoptotic cell death in breast cancer cells

FIG. 6 Apoptosis induction by Centans in breast cancer cells. Annexin V/PI staining of (A) MCF-7 and (B) MDA-MB231 cells were treated with vehicle (DMSO) or Centans at indicated concentrations for 24 h and DNA fragmentation was assessed by flow cytometry using the FL1-H channel (Annexin-V) and FL2-H channel (PI) of a Becton Dickinson FACS Calibur. Shown are representative dot plots. Quantification of flow cytometry data shown as percent of total cells (right panel). Data presented as mean±SEM from three independent experiments; *P<0.05, P<0.01, and *P<0.001 compared to control.

Centans Inhibits EGFR and Her2 Phosphorylation

Figure 7:
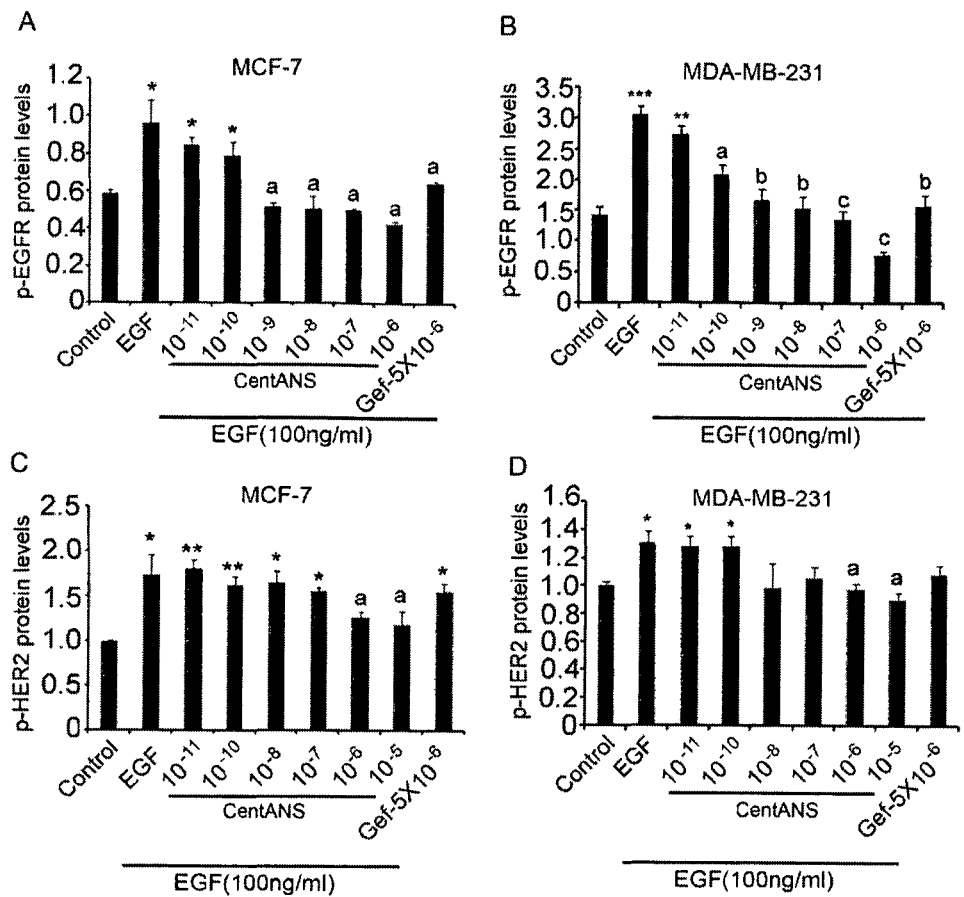
FIG. 7: Centans induces dephosphorylation of epidermal growth factor receptor (EGFR) and human epidermal growth factor receptor 2 (Her2).

Since EGFR and Her2 play major roles in breast cancer development and metastatis, the effect of Centans on regulation of these two factors was evaluated in MCF-7 and MDA-MB-231 cells by enzyme-linked immunosorbant assays (ELISA). As depicted in FIGS. 7. A and B, EGF dependent EGFR phosphorylation at $Tyr^{1068}$ was strongly attenuated by Centans in both MCF-7 and MDA-MB-231 cells and this effect was much stronger than that of Gefitinib (marketted EGFR inhibitor/anti-cancer drug). The calculated IC50 for Centans in terms of EGFR phosphorylation were 14.7 nM (MCF-7) and 12.75 nM (MDA-MB-231). Centans treatment also significantly reduced HER2 phosphorylation in a dose-dependent manner in both MCF-7 and MDA-MB-231 cells (FIGS. 7C and D).

FIG. 7. Inhibition of EGFR and Her2 phosphorylation by Centans in MCF-7 and MDA-MB231 cells. Serum starved (A,C) MCF-7 cells and (B,D) MDA-MB231 cells were pre-incubated for 1 h with the indicated concentrations of Centans prior to stimulation with EGF for 15 min and EGFR (A and B) or Her2 (C and D) phosphorylation were measured by ELISA. Gef=Gefitinib. All doses are in μM.

Centans Reduces Tumor Volume in Mouse Xenograft Model:

The effect of Centans on the growth of MCF-7 xenograft tumor was studied. Injection of MCF-7 cells in the peritoneal cavity of NIH-III strain of nude mice resulted in the appearance of palpable tumors that rapidly grew from 9 d to 25 d. Beyond 25 d, vehicle treated mice bearing tumors (control) show significant mortality (data not shown). Administration of Centans at 16 $mg \cdot kg^{-1} \cdot day^{-1}$ dose resulted in nearly 50% reduction in relative tumor volume compared to vehicle treated mice on days 21 and 25 following the inoculation of MCF-7 cells (FIG. 8A).

Histological assessment showed that tumors from vehicle-treated mice were primarily composed of tumor epithelial cells with small amounts of mouse-derived stroma and frequent blood vessels. Tumors from mice treated with Centans presented with large areas of stroma where deletion of epithelial cells had occurred as evident from few mitotic figures (FIG. 8B). In addition, a significant reduction in the levels of PCNA (marker of proliferation) was observed in tumors from Centans treated mice compared to control (FIG. 8C).

Figure 8:
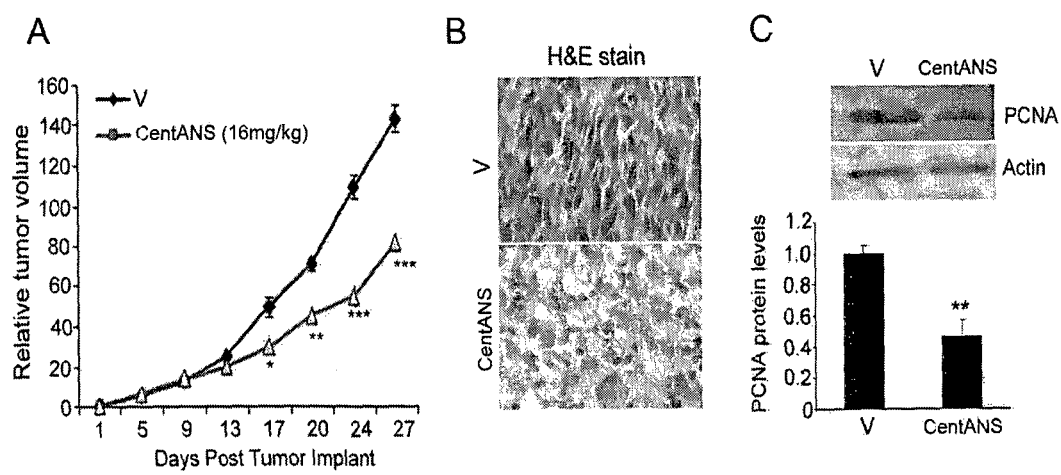
FIG. 8: Centans causes reduction of tumor volume in vivo.

FIG. 8 Regression of xenograft tumor by Centans in athymic nude mice. (A) Increase in relative tumor volume over time in various treatment groups indicated. N=10 mice/group; data represent mean±S.E.M. *P<0.05 and P<0.01 compared to vehicle (carboxymethyl cellulose). (B) Effect of Centans treatment on tumor morphology. Representative tumor sections from mice treated with vehicle or Centans (16 $mg \cdot kg^{-1} \cdot day^{-1}$) for 25 days. (C) Effect of Centans treatment on PCNA levels were analyzed by Western blotting from in tumors of vehicle or Centans treated mice. Data represent mean±S.E.M. P<0.01 compared to vehicle-treated control.

Centans Reduces CD133+Colon Cancer Stem Cells

Figure 9:
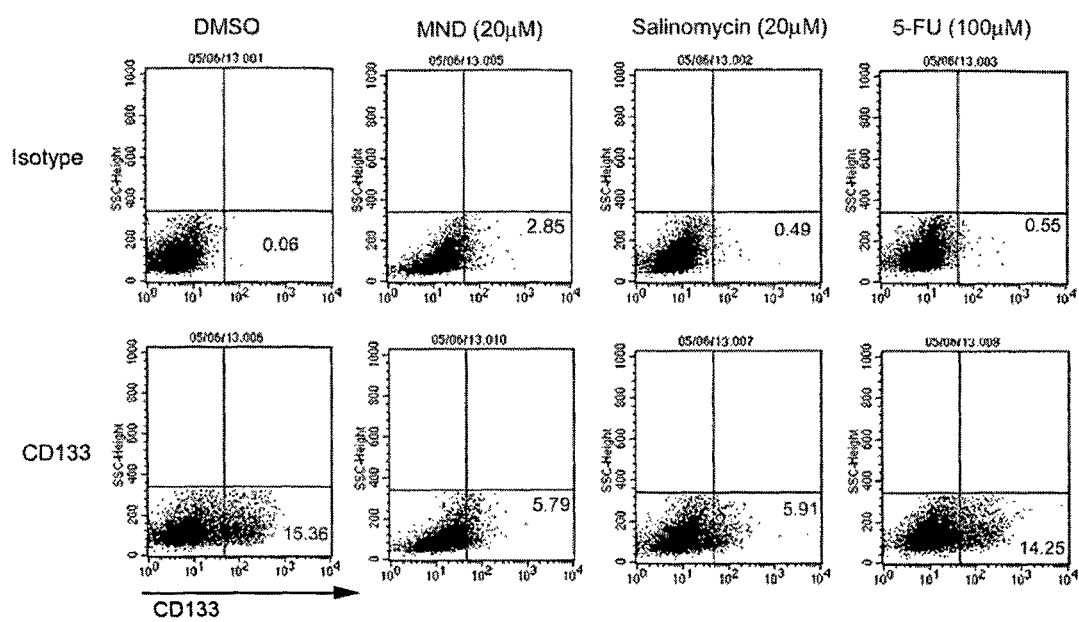
FIG. 9: Centans reduces CD133+ colon cancer stem cells.

Since centans showed cytotoxicity in drug resistant leukemic cells, the efficacy of centans in cancer stem cells (CD133+DLD1 colon cancer cells) was assessed. As shown in FIG. 9. In vehicle (DMSO) treated control cells 15.30% cells were found to be CD133+ (value represents % CD133+ cells minus % cells in isotype control) and 24h treatment with 20 uM centans reduced this population to 2.94% (5.79-2.85), while salinomycin the positive control at equivalent concentration reduced the CD133+ population to 5.42% (5.91-0.49) and 5-FU had no effect.

FIG. 9. Centans reduces CD133+ colon cancer stem cells with a higher efficacy than salinomycin. DLD1 colon cancer cells were treated with indicated compounds for 24h following which the CD133+ population was assessed by flow cytometry using CD133 antibody or relevant isotype control antibody (BD biosciences) in a Becton Dickinson FACS Calibur. Numbers in the dot plot represent % CD133+ cells.

Advantages of the Present Invention
1. The present compound shows better efficacy than existing drugs imatinib and dasatinib both in leukemia cell-lines and patient samples.
2. The present compound causes robust apoptosis in imatinib resistant cancer samples.
3. The present compound induces cell death in broader range of leukemic cells than imatinib or dasatinib.
4. The present compound induces differentiation in blast cells which is indicative of restoring normal blood cell functions.
5. The present compound is also efficacious in solid tumor forming cell-lines including, breast, prostate and endometrial cancers.

We claim:
1. A compound of formula I or a pharmaceutically acceptable salt thereof,

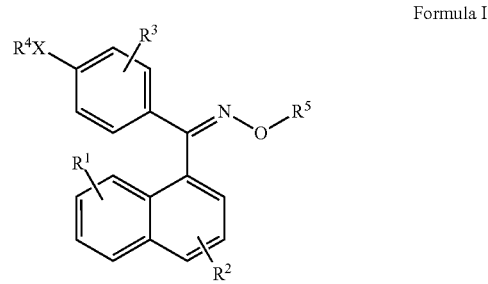

Formula I $R^1$=H, Halogen, alkyl, alkoxy, or nitro
$R^2$=H, Halogen, alkyl, alkoxy, hydroxy, or nitro
$R^3$=H, alkyl, alkoxy, nitro, or halogen
X=O, or S
$R^4$=hydrogen, alkyl group ($C_1$-$C_6$), alkylamino group ($C_1$-$C_6$), cyclic, or open chain amines
$R^5$=alkyl group ($C_1$-$C_6$), alkylepoxy, alkylhydroxyamino group ($C_1$-$C_6$), alkylamino group ($C_1$-$C_6$), or cyclic or open chain amines, ester and amide derivatives selected from the group consisting of

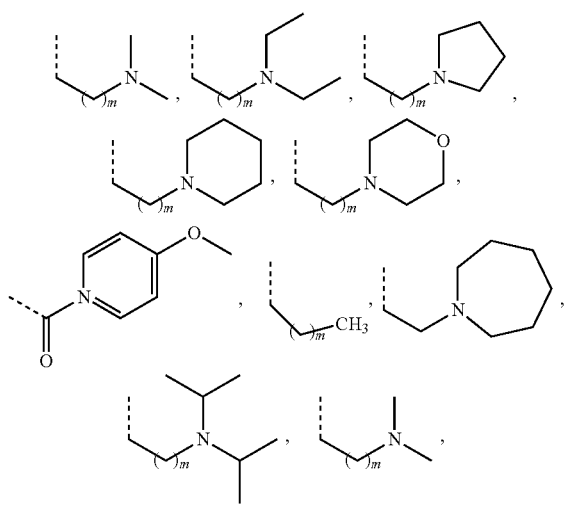

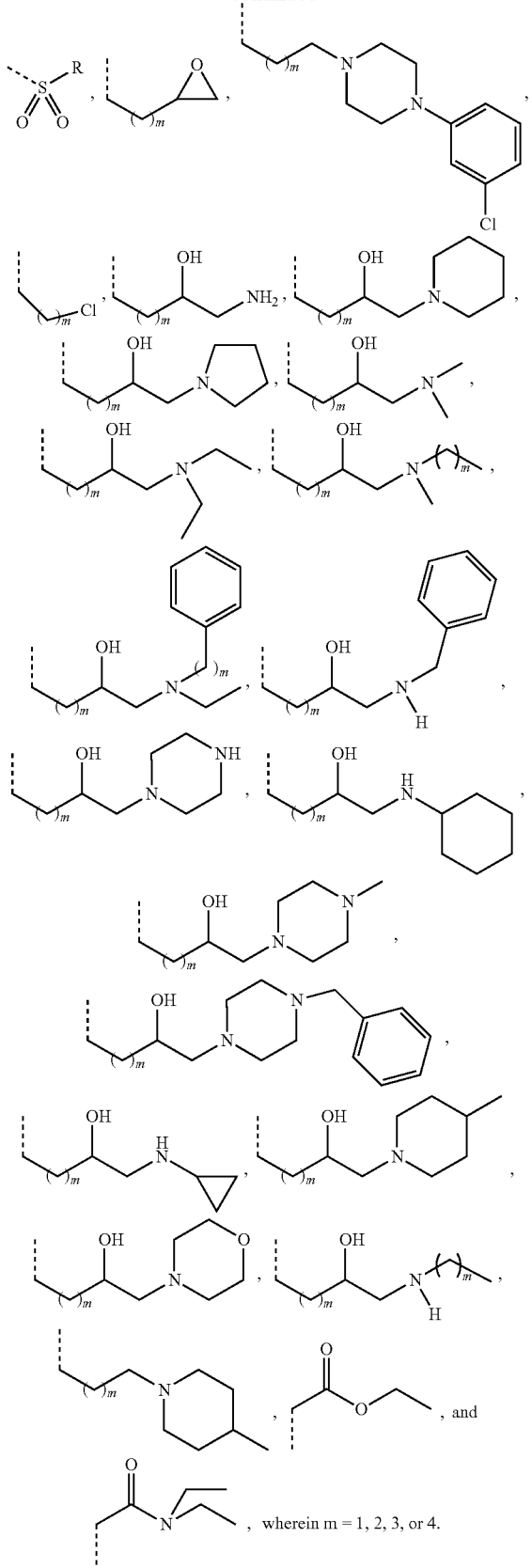

2. The compound of claim 1, wherein the compound is selected from the group consisting of:

(4-(methylthio)phenyl)(naphthalen-1-yl)methanone O-2-(piperidin-1-yl)ethyl oxime oxalate (5a),
(4-(methylthio)phenyl)(naphthalen-1-yl)methanone O-2-(pyrrolidin-1-yl)ethyl oxime oxalate (5b),
(4-(methylthio)phenyl)(naphthalen-1-yl)methanone O-2-(dimethylamino)ethyl oxime oxalate (5c),
(4-(methylthio)phenyl)(naphthalen-1-yl methanone O-2-(diethylamino)ethyl oxime oxalate (5d),
(4-(methylthio)phenyl)(naphthalen-1-yl)methanone O-2-(diisopropylamino)ethyl oxime (5e),
(4-(methylthio)phenyl)(naphthalen-1-yl)methanone O-2-morpholinoethyl oxime (5f),
(4-(methylthio)phenyl)(naphthalen-1-yl)methanone O-1-(dimethylamino)propan-2-yl oxime oxalate (5g),
(4-(methylthio)phenyl)(naphthalen-1-yl)methanone O-2-(azepan-1-yl)ethyl oxime oxalate (5h),
(4-(methylthio)phenyl)(naphthalen-1-yl)methanone O-2-(diethylamino)ethyl oxime citrate (5i),
(4-(methylthio)phenyl)(naphthalen-1-yl)methanone O-2-(diethylamino)ethyl oxime fumarate (5j),
(4-(methylthio)phenyl)(naphthalen-1-yl)methanone O-2-(diethylamino)ethyl oxime tartrate (5k),
(4-(methylthio)phenyl)(naphthalen-1-yl)methanone O-2-(diethylamino)ethyl oxime (5l),
(4-(methylthio)phenyl)(naphthalen-1-yl)methanone O-3-(dimethylamino)propyl oxime oxalate (5m),
(4-(methylthio)phenyl)(naphthalen-1-yl)methanone O-3-chloropropyl oxime (5n),
(4-(methylthio)phenyl)(naphthalen-1-yl)methanone O-4-chlorobutyl oxime (5o),
Ethyl 2-(4-(methylthio)phenyl)(naphthalen-1-yl)methyleneaminooxy)acetate (5p),
N,N-diethyl-2-(4-(methylthio)phenyl)(naphthalen-1-yl)methyleneaminooxy) acetamide (5q),
(4-methoxyphenyl)(naphthalen-1-yl)methanone O-2-(piperidin-1-yl)ethyl oxime oxalate (6a),
(4-methoxyphenyl)(naphthalen-1-yl)methanone O-2-(pyrrolidin-1-yl)ethyl oxime oxalate (6b),
(4-methoxyphenyl)(naphthalen-1-yl)methanone O-2-(dimethylamino)ethyl oxime oxalate (6c),
(4-methoxyphenyl)(naphthalen-1-yl)methanone O-2-(diethylamino)ethyl oxime oxalate (6d),
(4-methoxyphenyl)(naphthalen-1-yl)methanone O-2-(diisopropylamino)ethyl oxime oxalate (6e),
(4-methoxyphenyl)(naphthalen-1-yl)methanone O-1-(dimethylamino)propan-2-yl oxime oxalate (6f),
(4-methoxyphenyl)(naphthalen-1-yl)methanone O-2-(azepan-1-yl)ethyl oxime oxalate (6g),
(4-methoxyphenyl)(naphthalen-1-yl)methanone O-2-motpholinoethyl oxime (6h),
(4-methoxyphenyl)(naphthalen-1-yl)methanone O-3-(dimethylamino)propyl oxime oxalate (6i),
(4-methoxyphenyl)(naphthalen-1-yl)methanone O-3-chloropropyl oxime (6j),
(4-methoxyphenyl)(naphthalen-1-yl)methanone O-3-(piperidin-1-yl)propyl oxime (6k),
(4-(methylthio)phenyl)(naphthalen-1-yl)methanone O-3-(piperidin-1-yl)propyl oxime oxalate (7a),
(4-(methylthio)phenyl)(naphthalen-1-yl)methanone O-3-morpholinopropyl oxime (7b),
(4-(methylthio)phenyl)(naphthalen-1-yl)methanone O-3-(4-methylpiperidin-1-yl)propyl oxime oxalate (7c),
(4-(methylthio)phenyl) (naphthalen-1-yl)methanone O-3-(butyl(methyl)amino) propyl oxime (7d),
(4-methoxyphenyl)(naphthalen-1-yl)methanone O-3-(2-ethylhexylamino)propyl oxime (7e), (4-(methylthio)phenyl)(naphthalen-1-yl)methanone O-4-(piperidin-1-yl)butyl oxime (8a),
(4-(methylthio)phenyl)(naphthalen-1-yl)methanone O-4-(pyrrolidin-1-yl)butyl oxime (8b),
(4-(methylthio)phenyl)(naphthalen-1-yl)methanone O-4-(phenethylamino)butyl oxime (8c), and
(4-(methylthio)phenyl)(naphthalen-1-yl)methanone O-4-(benzyl(ethyl)amino) butyl oxime (8d).

3. The compound of claim 1, wherein the structural formula of the compound is:

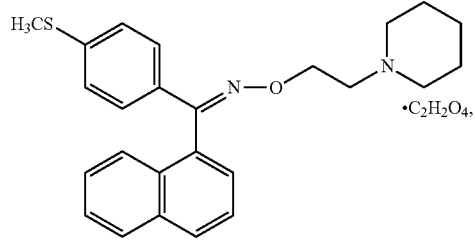
5a

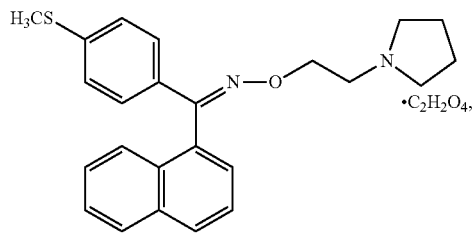
5b

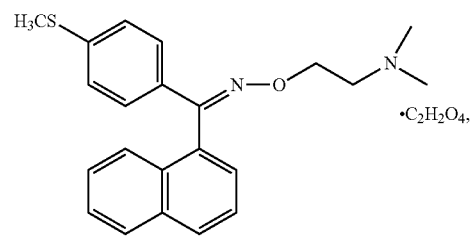
5c

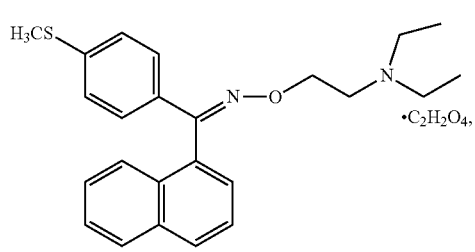
5d

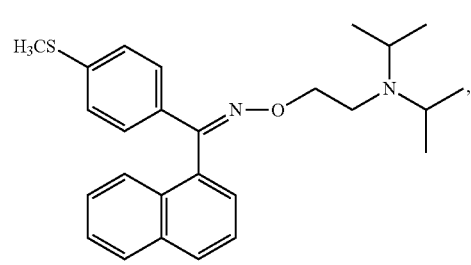
5e

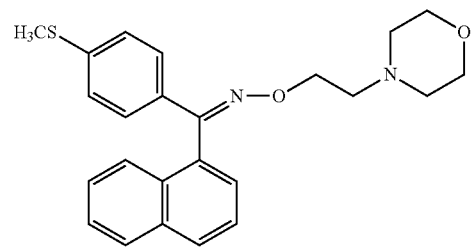
5f

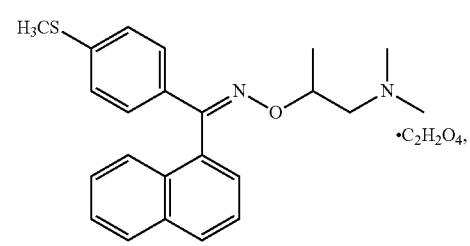
5g

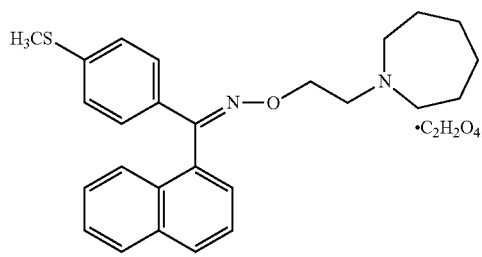
5h

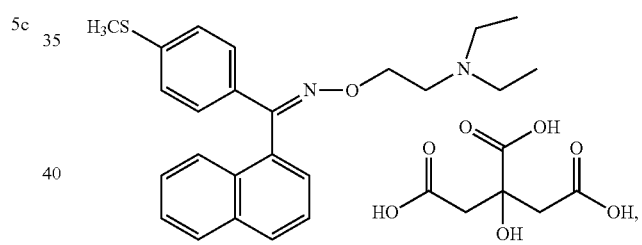
5i

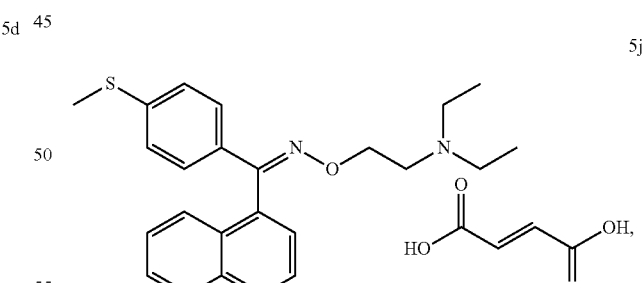
5j

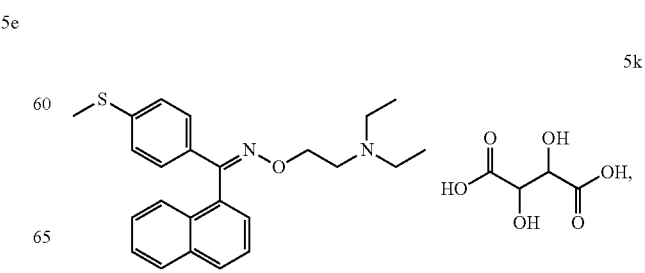
5k

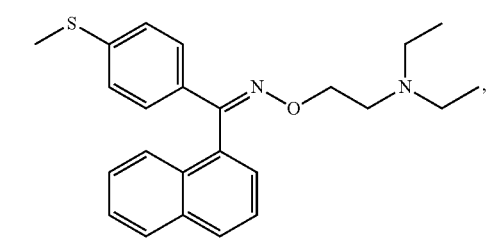 5l
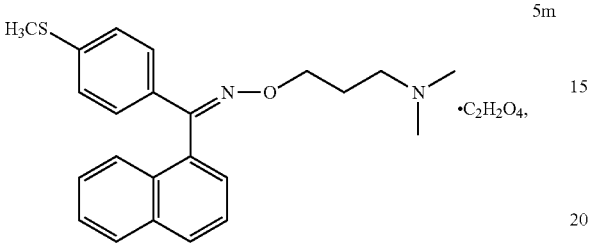 5m
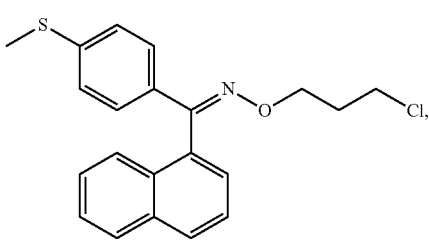 5n
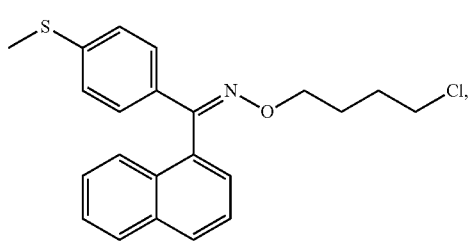 5o
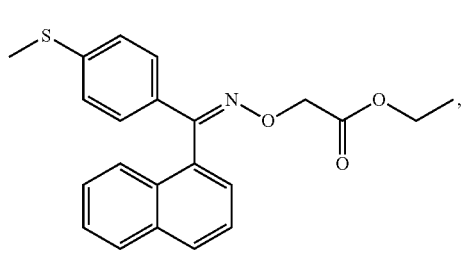 5p
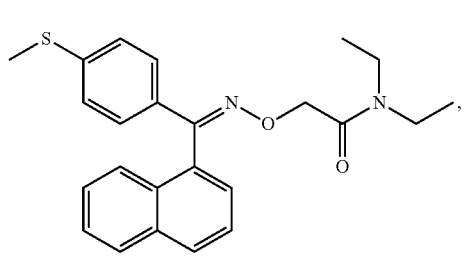 5q
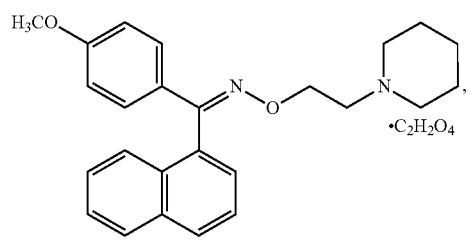 6a
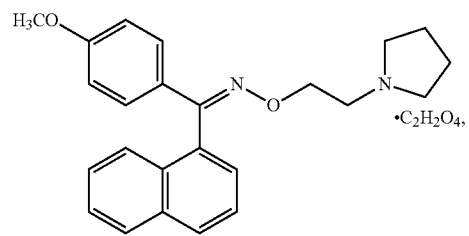 6b
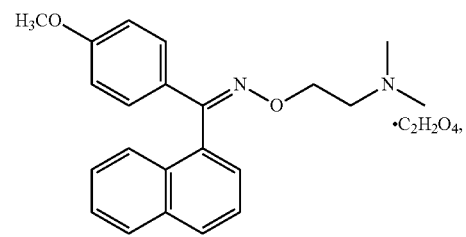 6c
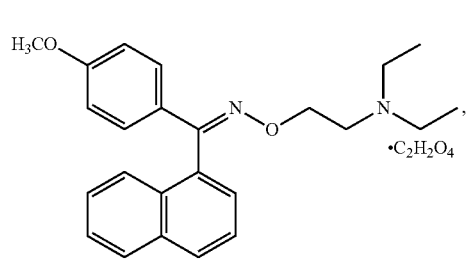 6d
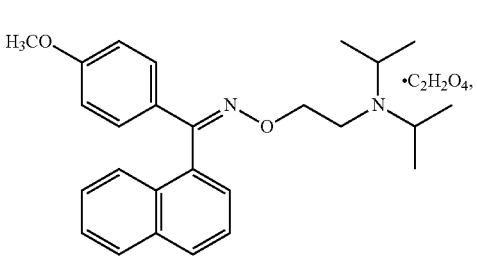 6e
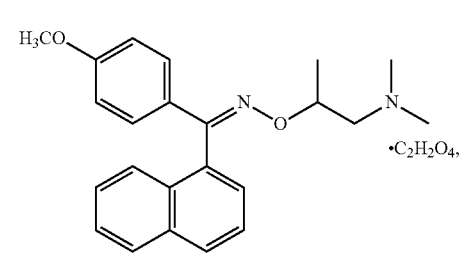 6f

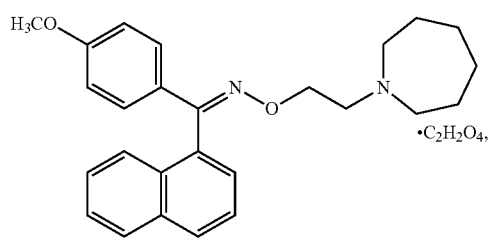
6g
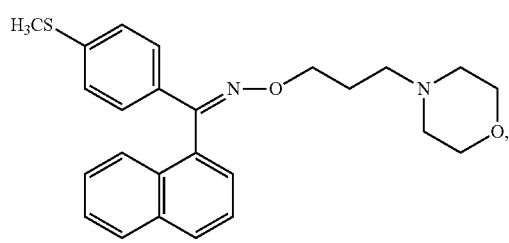
7b
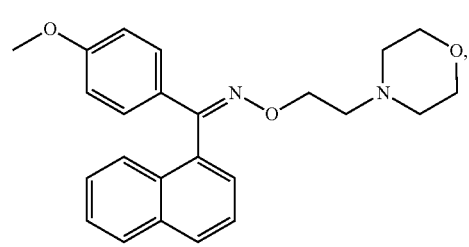
6h
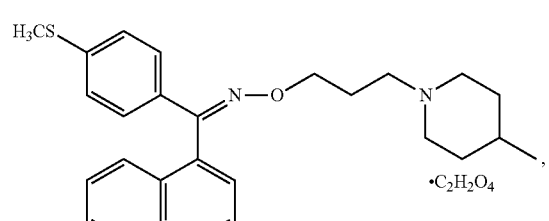
7c
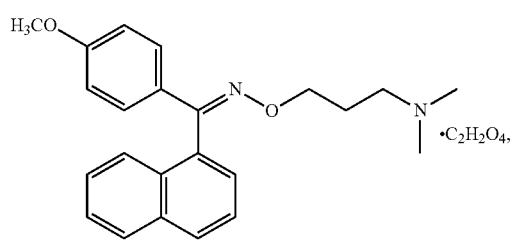
6i
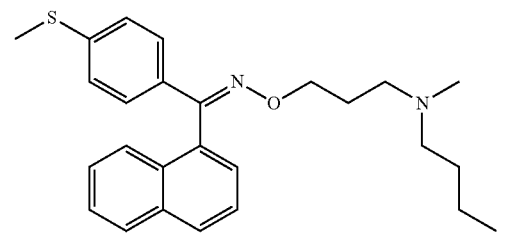
7d
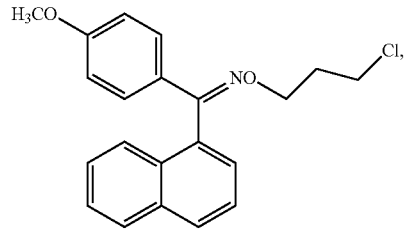
6j
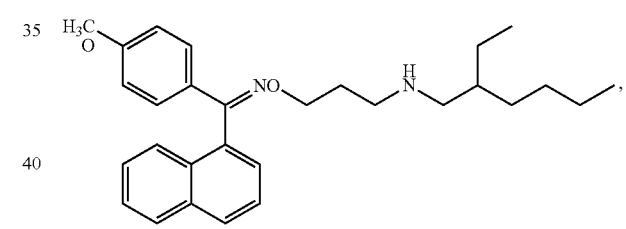
7e
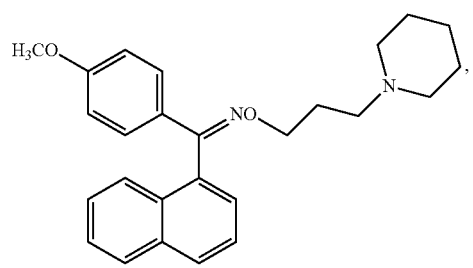
6k
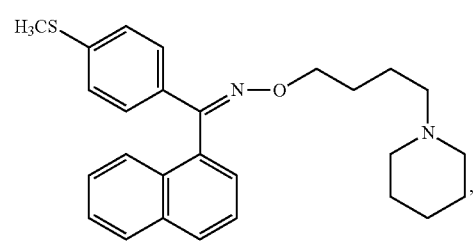
8a
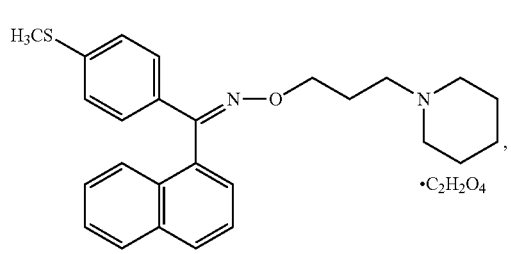
7a
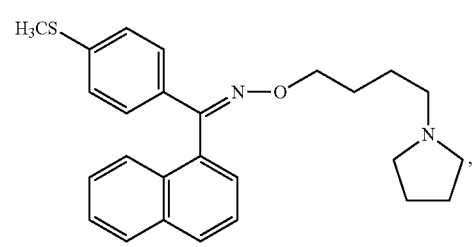
8b -continued 8c

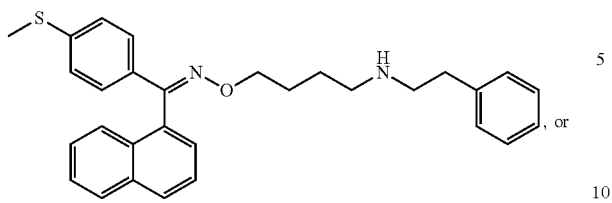

, or

8d

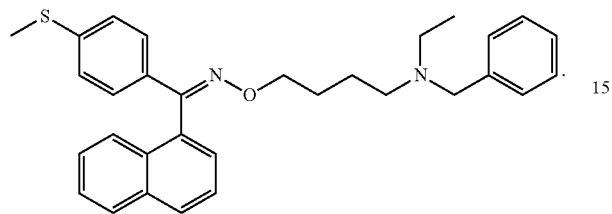

4. The compound of claim 1, wherein the pharmaceutically acceptable salt is selected from the group consisting of hydrochlorides, citrates, oxalates, fumarates, malates and tartrates.

5. A pharmaceutical composition comprising the compound of claim 1.

6. The pharmaceutical composition of claim 5, further comprising a pharmaceutically acceptable carrier or diluent.

* * * * *